(12) United States Patent
Davio et al.

(10) Patent No.: US 9,278,132 B2
(45) Date of Patent: Mar. 8, 2016

(54) OPHTHALMIC PHARMACEUTICAL COMPOSITIONS AND METHODS OF MAKING AND USING SAME

(71) Applicant: Bausch & Lomb Incorporated, Rochester, NY (US)

(72) Inventors: Stephen R. Davio, Fairport, NY (US); Paramita Sarkar, Webster, NY (US); Zora T. Marlowe, Rochester, NY (US); Brian J. Glass, Henrietta, NY (US); Tammy J. Kleiber, Rochester, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 13/739,018

(22) Filed: Jan. 11, 2013

(65) Prior Publication Data

US 2013/0210912 A1    Aug. 15, 2013

Related U.S. Application Data

(60) Provisional application No. 61/597,879, filed on Feb. 13, 2012.

(51) Int. Cl.

| | |
|---|---|
| *A61K 47/32* | (2006.01) |
| *A61K 47/36* | (2006.01) |
| *A61K 9/00* | (2006.01) |
| *A61K 9/107* | (2006.01) |
| *A61K 47/38* | (2006.01) |
| *A61K 47/14* | (2006.01) |

(52) U.S. Cl.
CPC ............... *A61K 47/36* (2013.01); *A61K 9/0048* (2013.01); *A61K 9/107* (2013.01); *A61K 47/14* (2013.01); *A61K 47/32* (2013.01); *A61K 47/38* (2013.01)

(58) Field of Classification Search
CPC ....... A61K 47/32; A61K 47/36; A61K 47/38; A61K 47/14
See application file for complete search history.

(56) References Cited

U.S. PATENT DOCUMENTS

| | | | |
|---|---|---|---|
| 4,409,205 A | 10/1983 | Shively | |
| 5,209,927 A | 5/1993 | Gressel et al. | |
| 5,294,607 A | 3/1994 | Glonek et al. | |
| 6,114,319 A * | 9/2000 | Kimura et al. | 514/177 |
| 2011/0319487 A1 | 12/2011 | Mercier | |

FOREIGN PATENT DOCUMENTS

| | | |
|---|---|---|
| CN | 1437947 A | 8/2003 |
| CN | 1456157 A | 11/2003 |
| EP | 1985298 A1 | 10/2008 |
| WO | 2010/141648 A2 | 12/2010 |
| WO | 2013/052760 A1 | 4/2013 |

OTHER PUBLICATIONS

Badolato et al., "Evaluation of long term stability of model emulsions by multisample analytical centrifugation," Progress in Colloid Polymer Science (2008), vol. 134, pp. 66-73.
Chiu et al., "Using analytical centrifugation to characterize the dispersibility and particle size distributions of organic/inorganic composite coatings," Journal of Polymer Research (2011), vol. 18, pp. 1587-1596.
Detloff et al., "Particle size distribution by space or time dependent extinction profiles obtained by analytical centrifugation (concentrated systems)," Powder Technology (2007), vol. 174, pp. 50-55.
Martindale, The complete drug reference (2005), 34th ed., pp. 1411-1416.
Remington, "The Science and Practice of Pharmacy," 21st ed., p. 291.
Remington, "The Science and Practice of Pharmacy," 21st ed., Chapter 22.
Castor Oil (n.d.). In Wikipedia. Retrieved Jul. 18, 2014, from http://en.wikipedia.org/wiki/Castor_oil.
Product Data Sheet for Myritol® 318 published by Cognis/Care Chemicals, Revision No. 3-08.2000.
Product Data Sheet for Myritol® 312 published by Cognis/Care Chemicals, Revision No. 4-07.2001.
Brochure entitled, "Excipients for Pharmaceuticals" published by Sasol. Text dated Jul. 2010 available at www.sasoltechdata.com/.../Excipients_Pharmaceuticals.pdf.

* cited by examiner

*Primary Examiner* — Zohreh Fay
(74) *Attorney, Agent, or Firm* — Toan P. Vo

(57) ABSTRACT

A stable ophthalmic pharmaceutical composition for relief, treatment, control, alleviation, or prevention of a pathological ocular condition of the eye comprises: (a) a first polymer, a viscosity of which changes with a change in a concentration of an electrolyte, such as a salt, when added to said first polymer; (b) a second polymer that is different from the first polymer and can modify the viscosity of the first polymer; and (c) an oil. In some embodiments, the composition further comprises a non-ionic surfactant. The composition can form a stable oil-in-water emulsion on storage, but separate into an oil phase and a water phase when applied in the eye. The emulsion can comprises an ophthalmic active pharmaceutical ingredient dissolved in the oil or water phase. The emulsion can provide enhanced stability to said active pharmaceutical ingredient.

8 Claims, 52 Drawing Sheets

OPHTHALMIC PHARMACEUTICAL COMPOSITIONS AND METHODS OF MAKING AND USING SAME

CROSS REFERENCE

This application claims the benefit of Provisional Patent Application No. 61/597,879 filed Feb. 13, 2012 which is incorporated by reference herein.

BACKGROUND

The present invention relates to ophthalmic pharmaceutical compositions and methods of making and using such compositions. The present invention also relates to enhanced delivery of ophthalmic pharmaceutical ingredients in ophthalmic compositions and methods of making and using such compositions. Some embodiments of the present invention relate to compositions and methods for reducing, ameliorating, treating, or preventing discomfort of dry eye condition.

Prior-art ophthalmic compositions often suffer from inefficient delivery of beneficial ingredients, including ophthalmic pharmaceutical active ingredients, to the eye. Disadvantages of these compositions include short duration of the composition on the eye due to continuous drainage or evaporation.

Dry eye, also known as keratoconjunctivitis sicca or dyslacrima, is a common ophthalmological disorder affecting millions of people. A patient with dry eye may experience burning, a feeling of dryness, and persistent irritation. In severe cases, dry eye can seriously impair a person's vision and hence handicap the sufferer in activities such as driving. Certain diseases such as Sjogren's disease manifest dry eye symptoms. Also, as people age, the lacrimal glands in the eye may produce less moisture, resulting in eyes that become dry, inflamed, itchy, and gritty.

Although it appears that dry eye may result from a variety of unrelated pathogenic causes, all presentations of the condition share a common feature, namely the breakdown of the precorneal tear film, which breakdown commonly results in dehydration of the exposed outer ocular surface and hence the symptoms described above.

A number of approaches exist for the treatment of dry eye. One common approach has been to supplement the ocular tear film using artificial tears instilled throughout the day. Examples of the tear substitute approach include the use of buffered, isotonic saline solutions and aqueous solutions containing water-soluble polymers that render the solutions more viscous and thus less easily shed by the eye by the washing action of the tear fluid. See, for example, U.S. Pat. No. 5,209,927 to Gressel et al.; U.S. Pat. No. 5,294,607 to Glonek et al.; and U.S. Pat. No. 4,409,205 to Shively;

Although these approaches have met with some success in some cases, significant challenges in the treatment of dry eye nevertheless remain. Problems include the fact that the use of tear substitutes, while temporarily effective, generally requires repeated application over the course of a patient's waking hours, not uncommonly ten or more times over the course of a day to keep the ocular surface lubricated or moist. Such an approach is inconvenient to a patient. Although increasing the viscosity of the dry-eye product may extend the product's duration in the eye, increase in viscosity is effective at extending duration only to a limited extent. Viscous ophthalmic drops are sometimes undesirable because they feel sticky in the eye. Further, increases in the duration of the product would be highly desirable.

Therefore, in view of the shortcomings of prior-art compositions, there is a continued need to provide improved ophthalmic pharmaceutical compositions for enhanced delivery of active pharmaceutical ingredients ("APIs") to the eye. For example, it is desirable to provide improved ophthalmic compositions for the reduction, amelioration, treatment, or prevention of the discomfort resulting from the dry eye condition. It is also desirable to provide such compositions that are gentle to the ocular surface.

SUMMARY

In general, the present invention provides an ophthalmic pharmaceutical composition that is capable of providing enhanced delivery of an ophthalmic pharmaceutical ingredient to the eye. In some embodiments, such an ophthalmic pharmaceutical ingredient is an ophthalmic active pharmaceutical ingredient ("API").

In one aspect, the present invention provides an ophthalmic pharmaceutical composition that is capable of reducing, ameliorating, treating, or preventing a pathological condition of the eye.

In still another, the present invention provides an ophthalmic pharmaceutical composition that is capable of reducing, ameliorating, treating, or preventing impairment of vision resulting from a pathological condition of the eye.

In another aspect, such a pathological condition of the eye is the dry eye condition. Thus, in one aspect, the present invention provides a composition that is capable of reducing, ameliorating, treating, or preventing impairment of vision resulting from a condition of dry eye.

In another aspect, a composition of the present invention has lower risk of introducing unwanted exogenous side effects, such as an unwanted sensation. Alternatively, the composition is gentle to the ocular surface.

In still another aspect, a composition of the present invention comprises: (a) a first polymer, a viscosity of which changes when a salt is added to said first polymer; (b) a second polymer that is different from the first polymer; and (c) an oil.

In still another aspect, a composition of the present invention comprises: (a) a first polymer, a viscosity of which changes when an electrolyte, such as a salt, is added to said first polymer or a composition comprising said first polymer; (b) a second polymer that is different from the first polymer; and (c) an oil.

In yet another aspect, a composition of the present invention comprises: (a) a first polymer, a viscosity of which changes in response to a change in concentration of an electrolyte, such as a salt, when added to said first polymer or a composition comprising said first polymer; (b) a second polymer that is different from the first polymer; and (c) an oil.

In yet another aspect, a composition of the present invention comprises: (a) a first polymer, a viscosity of which changes with a change in concentration of an electrolyte, such as a salt, when added to said first polymer; (b) a second polymer that is different from the first polymer and that can modify the viscosity of the first polymer; and (c) an oil selected from triglycerides.

In a further aspect, a composition of the present invention comprises: (a) a first polymer, a viscosity of which changes with a change in a concentration of an electrolyte, such as a salt, when added to said first polymer; (b) a second polymer that is different from the first polymer; (c) an oil; and (d) a non-ionic surfactant.

In still another aspect, a composition of the present invention comprises an emulsion which comprises: (a) a first polymer, a viscosity of which changes with a change in a concentration of an electrolyte, such as a salt, when added to said first polymer; (b) a second polymer that is different from the first polymer; and (c) an oil.

In yet another aspect, a composition of the present invention comprises: (a) a first polymer, a viscosity of which changes with a change in concentration of an electrolyte, such as a salt, when added to said first polymer; (b) a second polymer that is different from the first polymer and that can modify the viscosity of the first polymer; (c) an oil; and (d) an active pharmaceutical ingredient dissolved in said oil.

In yet another aspect, a composition of the present invention comprises: (a) a first polymer, a viscosity of which changes with a change in concentration of an electrolyte, such as a salt, when added to said first polymer; (b) a second polymer that is different from the first polymer and that can modify the viscosity of the first polymer; (c) an oil selected from triglycerides; and (d) an active pharmaceutical ingredient dissolved in said oil.

In yet another aspect, a composition of the present invention comprises an emulsion which comprises: (a) a first polymer, a viscosity of which changes with changes in a concentration of an electrolyte, such as a salt, when added to said first polymer; (b) a second polymer that is different from the first polymer; and (c) an oil; wherein the composition has a viscosity in the range from about 100 to 1500 centipoises ("cp" or mPa·s), as measured by a method disclosed herein below.

In a further aspect, a composition of the present invention comprises an emulsion which comprises: (a) a first polymer, a viscosity of which changes with a change in a concentration of an electrolyte, such as a salt, when added to said first polymer; (b) a second polymer that is different from the first polymer; and (c) an oil; wherein the emulsion comprises an oil phase-in-aqueous phase emulsion.

In a further aspect, the present invention also provides a method of reducing, ameliorating, treating, or preventing a pathological condition of an eye; wherein the method comprises administering to an eye of a subject suffering from such a condition any one of the compositions herein disclosed.

In one embodiment, the present invention also provides a method of reducing, ameliorating, treating, or preventing a condition of dry eye; wherein the method comprises administering to an eye of a subject suffering from such a condition any one of the compositions herein disclosed.

Other features and advantages of the present invention will become apparent from the following detailed description and claims.

DETAILED DESCRIPTION

Figure 1:
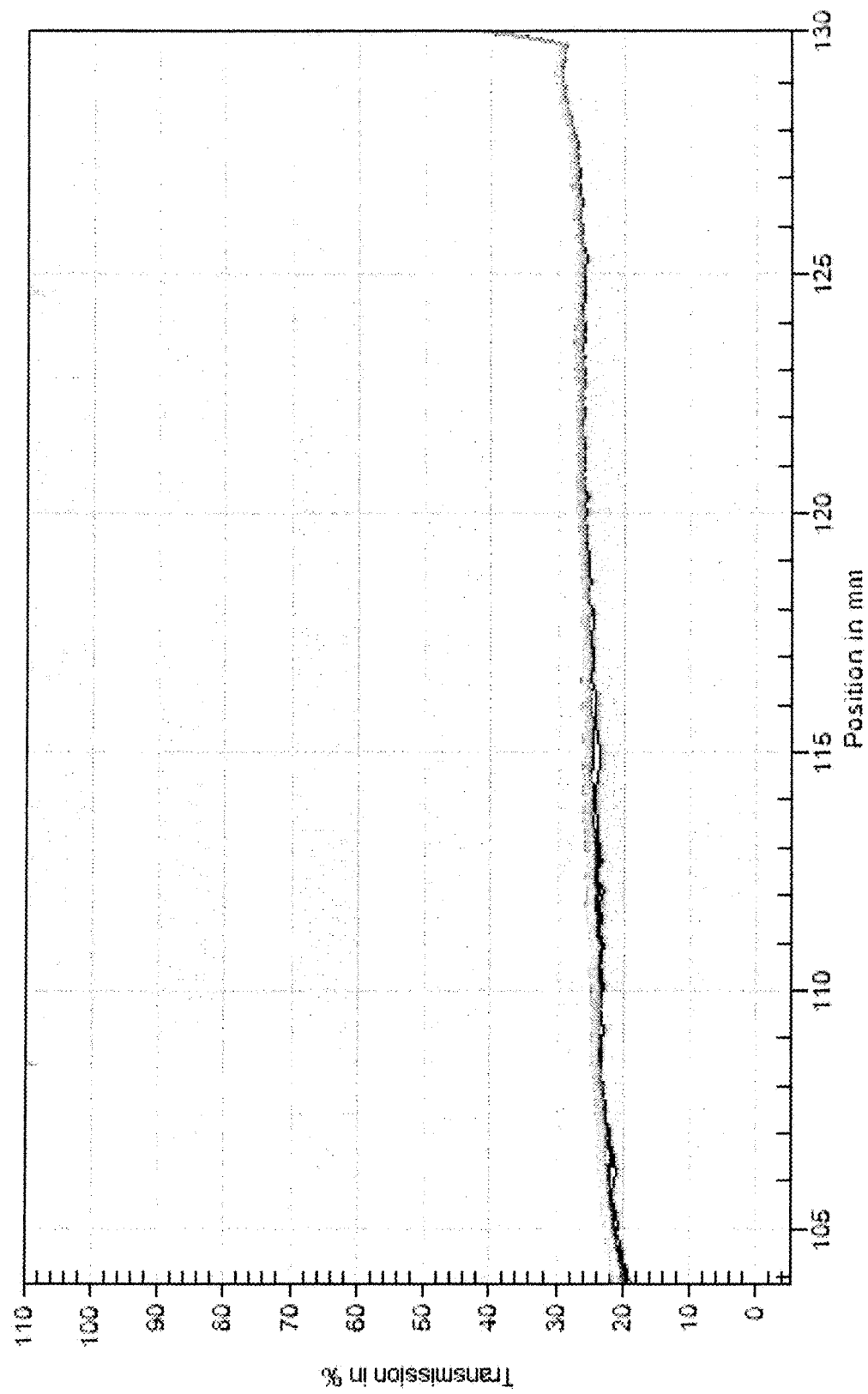
FIG. 1 shows Lumisizer™ light transmission measurement through neat Formulation F1.

In general, the present invention provides an ophthalmic pharmaceutical composition that is capable of providing enhanced delivery of an ophthalmic pharmaceutical ingredient to the eye. In some embodiments, such an ophthalmic pharmaceutical ingredient is an ophthalmic active pharmaceutical ingredient ("API").

In one aspect, the present invention provides a composition that is capable of reducing, ameliorating, treating, or preventing impairment of vision resulting from a pathological condition of an eye.

In another aspect, the present invention provides a composition that is capable of reducing, ameliorating, or treating impairment of vision resulting from a pathological condition of an eye.

In still another aspect, the composition has lower risk of introducing unwanted exogenous side effects, such as an unwanted irritating, burning, or stinging sensation. Alternatively, the composition is gentle to the ocular surface.

In still another aspect, a composition of the present invention comprises: (a) a first polymer, a viscosity of which changes with a change in a concentration of an electrolyte, such as a salt, when added to said first polymer; (b) a second polymer that is different from the first polymer; and (c) an oil. In one embodiment, the viscosity of the first polymer decreases with an increase in a concentration of the salt.

In still another aspect, a composition of the present invention comprises: (a) a first polymer, a viscosity of which changes in response to a change in a concentration of an electrolyte, such as a salt, when added to said first polymer or a composition comprising said first polymer; (b) a second polymer that is different from the first polymer; and (c) an oil. In one embodiment, the viscosity of the first polymer decreases with an increase in a concentration of said electrolyte.

In yet another aspect, a composition of the present invention comprises, consists of, or consists essentially of: (a) a first polymer, a viscosity of which changes in response to a change in a concentration of an electrolyte, such as a salt, when added to said first polymer or a composition comprising said first polymer; (b) a second polymer that is different from the first polymer; (c) an oil; and (d) water. In one embodiment, the viscosity of the first polymer decreases with an increase in a concentration of the salt.

In yet another aspect, a composition of the present invention comprises: (a) a first polymer, a viscosity of which changes with a change in concentration of an electrolyte, such as a salt, when added to said first polymer; (b) a second polymer that is different from the first polymer and that can modify the viscosity of the first polymer; and (c) an oil selected from triglycerides.

In yet another aspect, a composition of the present invention comprises: (a) a first polymer, a viscosity of which changes with a change in a concentration of an electrolyte, such as a salt, when added to said first polymer or a composition comprising said first polymer; (b) a second polymer that is different from the first polymer and that can modify the viscosity of the first polymer; and (c) an oil selected from triglycerides. In one embodiment, the viscosity of the first polymer decreases with an increase in a concentration of the salt.

In still another aspect, a composition of the present invention comprises: (a) a first polymer, a viscosity of which changes in response to a change in a concentration of an electrolyte, such as a salt, when added to said first polymer or a composition comprising said first polymer; (b) a second polymer that is different from the first polymer and that can modify the viscosity of the first polymer; and (c) an oil selected from medium-chain triglycerides.

In a further aspect, a composition of the present invention comprises: (a) a first polymer, a viscosity of which changes with a change in a concentration of an electrolyte, such as a salt, when added to said first polymer; (b) a second polymer that is different from the first polymer; (c) an oil; and (d) a non-ionic surfactant. In one embodiment, the viscosity of the first polymer decreases with an increase in a concentration of the salt. In another embodiment, the composition further comprises water.

In yet another aspect, a composition of the present invention comprises, consists of, or consists essentially of: (a) a first polymer, a viscosity of which changes with a change in a concentration of an electrolyte, such as a salt, when added to said first polymer; (b) a second polymer that is different from the first polymer; (c) an oil; (d) a non-ionic surfactant; and (e) water. In one embodiment, the viscosity of the first polymer decreases with an increase in a concentration of the salt.

In a further aspect, a composition of the present invention comprises: (a) a first polymer, a viscosity of which changes with a change in a concentration of an electrolyte, such as a salt, when added to said first polymer or a composition comprising said first polymer; (b) a second polymer that is different from the first polymer; (c) an oil; and (d) a non-ionic surfactant.

In still another aspect, a composition of the present invention comprises an emulsion which comprises: (a) a first polymer, a viscosity of which changes with a change in a concentration of an electrolyte, such as a salt, when added to said first polymer; (b) a second polymer that is different from the first polymer; and (c) an oil. In one embodiment, the viscosity of the first polymer decreases with an increase in a concentration of said electrolyte.

In still another aspect, a composition of the present invention comprises an emulsion which comprises: (a) a first polymer, a viscosity of which changes with a change in a concentration of an electrolyte, such as a salt, when added to said first polymer or a composition comprising said first polymer; (b) a second polymer that is different from the first polymer; and (c) an oil.

In a further aspect, a composition of the present invention comprises an emulsion which comprises: (a) a first polymer, a viscosity of which changes in response to a change in a concentration of an electrolyte, such as a salt, when added to said first polymer or a composition comprising said first polymer; (b) a second polymer that is different from the first polymer; and (c) an oil selected from the group consisting of medium-chain triglycerides. In one embodiment, the viscosity of the first polymer decreases with an increase in a concentration of said electrolyte, such as said salt.

In yet another aspect, a composition of the present invention comprises an emulsion which comprises: (a) a first polymer, a viscosity of which changes with a change in a concentration of an electrolyte, such as a salt, when added to said first polymer or a composition comprising said first polymer; (b) a second polymer that is different from the first polymer; (c) an oil selected from the group consisting of medium-chain triglycerides; and (d) a non-ionic surfactant. In one embodiment, the viscosity of the first polymer decreases with an increase in a concentration of said electrolyte, such as said salt.

In yet another aspect, a composition of the present invention comprises an emulsion which comprises: (a) a first polymer, a viscosity of which changes with a change in a concentration of an electrolyte, such as a salt; (b) a second polymer that is different from the first polymer and that can modify a viscosity of said first polymer; and (c) an oil; wherein the composition has a viscosity in the range from about 100 to 1500 centipoises ("cp" or mPa·s), as measured by a method disclosed herein below.

Unless otherwise specified, the viscosity values or measurements disclosed herein were or are obtained with a Brookfield LVDV III Ultra viscometer at 37° C., using a CP-52 spindle, a 0.5 mL sample, at a shear rate program from 1 to 48 $sec^{-1}$, for undiluted samples; and at 37° C., using a CP-40 spindle, a 0.5 mL sample, at a shear rate program from 3.75 to 570 $sec^{-1}$, for diluted samples, such as with Hank's Balanced Salt Solution ("HBSS").

In a further aspect, a composition of the present invention comprises an emulsion which comprises: (a) a first polymer, a viscosity of which changes in response to a change in concentration of an electrolyte, such as a salt, added to said first polymer; (b) a second polymer that is different from the first polymer and that can modify a viscosity of said first polymer; and (c) an oil; wherein the emulsion comprises an oil phase-in-aqueous phase emulsion.

In a further aspect, a composition of the present invention comprises an emulsion which comprises, consists of, or consists essentially of: (a) a first polymer, a viscosity of which changes in response to a change in concentration of an electrolyte, such as a salt, added to said first polymer; (b) a second polymer that is different from the first polymer and that can modify a viscosity of said first polymer; (c) an oil; and (d) water; wherein the emulsion comprises an oil phase-in-aqueous phase emulsion.

In yet another aspect, a composition of the present invention comprises an emulsion which comprises, consists of, or consists essentially of: (a) a first polymer, a viscosity of which changes in response to a change in concentration of an electrolyte, such as a salt, added to said first polymer or a composition comprising said first polymer; (b) a second polymer that is different from the first polymer and that comprises a polyanionic polysaccharide; (c) an oil; and (d) water; wherein the emulsion comprises an oil phase-in-aqueous phase emulsion.

In still another aspect, a composition of the present invention comprises an emulsion which comprises, consists of, or consists essentially of: (a) a first polymer, a viscosity of which changes in response to a change in concentration of an electrolyte, such as a salt, added to said first polymer; (b) a second polymer that is different from the first polymer and that comprises a polyanionic polysaccharide; (c) an oil; and (d) water; wherein the emulsion comprises an oil phase-in-aqueous phase emulsion, and the emulsion is stable on storage but breaks up into separate aqueous and oil phases when diluted with tear resident in the eye. The term "stable on storage" means that there is no visible separation of phases when the composition is undisturbed at room temperature for at least one week. The term "polysaccharide," as used herein, includes natural or synthetic polymer comprising monomeric units of sugars and derivatives thereof (such as carboxycellulose, carboxyethyl cellulose, carboxymethyl cellulose, alginic acid, hyaluronic acid, xanthan gum, glucosaminoglycan, pectin, or salts thereof). For example, a composition of the present invention comprises an emulsion that is stable on storage, but separates into a water film and an outer oil film when the composition is administered on the ocular surface and is diluted with tear resident in the eye. In one embodiment, a composition of the present invention comprises an emulsion that is stable on storage, but separates into a water film and an outer oil film when the composition is administered on the ocular surface, is diluted with resident tear, and is optionally subject to blinking. A composition of the present invention, thus, can advantageously retard or inhibit rapid evaporation of the tear film, which is among the causes of dry eye. Moreover, a composition of the present invention can also provide extended lubrication of the corneal surface.

In still another aspect, a composition of the present invention comprises an emulsion which comprises, consists of, or consists essentially of: (a) a first polymer, a viscosity of which changes in response to a change in concentration of an electrolyte, such as a salt, added to said first polymer; (b) a second polymer that is different from the first polymer and that comprises a polyanionic polysaccharide; (c) an oil; (d) a non-ionic surfactant; and (e) water; wherein the emulsion comprises an oil phase-in-aqueous phase emulsion, and the emulsion is stable on storage but breaks up into separate aqueous and oil phases under shear stress.

In yet another aspect, a composition of the present invention has a pH in a range from about 5 to about 7.5. In one embodiment, the composition has a pH in the range from about 5.5 to about 7.5. In another embodiment, the composition has a pH in the range from about 6 to about 7.5 (or alternatively, from about 6 to about 7, or from about 5.5 to about 7, or from about 5.5 to about 6.5, or from about 5 to about 6.8, or from about 5.5 to about 6.8, or from about 5 to about 6.5, or from about 5 to about 6, or from about 5 to about 7, or from about 5 to about 5.5, or from about 6 to about 6.5).

In a further aspect, the first polymer comprises a polymer or copolymer of carboxyvinyl monomers. Non-limiting examples of the first polymer are polyacrylic acid, copolymer of acrylic acid, uncrosslinked or lightly crosslinked, such as those popularly known as carbomers (also known as Carbopol®, such as Carbopol® 71G, 971, 974, 980, 981, 5984, 934, 934P, 940, 941, 1342, and Ultrez 10), Pemulen® (such as Pemulen® TR-1 and TR-2), and Polycarbophil® (such as Noveon® AA-1).

In embodiments of the present invention, the first polymer is any polymer named above and is present in an amount from about 0.01 to about 2 percent by weight of the total composition. Alternatively, said first polymer is present in an amount from about 0.01 to about 1 percent by weight (or from about 0.01 to about 0.5, or from about 0.01 to about 0.3, or from about 0.01 to about 0.2, or from about 0.1 to about 1, or from about 0.1 to about 0.5, or from about 0.1 to about 0.3 percent by weight, or from about 0.1 to about 0.2) of the total composition.

In a further aspect, the second polymer comprises a polyanionic polymer or copolymer comprising units of monomeric sugars having an anionic group, and combinations thereof. Non-limiting examples of the second polymer are alginic acid, hyaluronic acid from different sources (including plant and animal sources, and products of fermentation), carboxymethylcellulose, carboxyethylcellulose, glucosaminoglycan, pectin, xanthan gum, and salts thereof.

In embodiments of the present invention, the second polymer is any second polymer named above and is present in an amount from about 0.01 to about 2 percent by weight of the total composition. Alternatively, said second polymer is present in an amount from about 0.01 to about 1 percent by weight (or from about 0.01 to about 0.5, or from about 0.01 to about 0.3, or from about 0.01 to about 0.2, or from about 0.1 to about 1, or from about 0.1 to about 0.5, or from about 0.1 to about 0.3 percent by weight, or from about 0.1 to about 0.2) of the total composition.

In one embodiment, said second polymer is alginate that comprises alternating homopolymeric blocks, each comprising or consisting of monomeric units of mannuronic acid (or a salt thereof) ("M") or guluronic acid (or a salt thereof) ("G"). In another embodiment, said alginate comprises alternating single units of M and G.

In another embodiment, said second polymer comprises a polysaccharide that comprises or is glucuronoxylomannan or variant thereof extracted from mushrooms, including glucuronoxylomannan extracted from the mushroom *Tremella* species, such as *Tremella fuciformis*. A variant of glucuronoxylomannan means a polysaccharide comprising additional monosaccharide units other than the mannose backbone chain and glucuronic acid and xylose units in its side chains. Such glucuroxylomannan is disclosed in U.S. Provisional Patent Application Ser. No. 61/509,283 (filed Jul. 19, 2011), which is incorporated herein by reference in its entirety.

In certain embodiments, said second polymer has a molecular weight in a range from about 50 kDa to about 5000 kDa. Alternatively, said second polymer has a molecular weight in a range from about 50 kDa to about 2000 kDa (or from about 50 kDa to about 1000 kDa, or from about 50 kDa to about 700 kDa, from about 50 kDa to about 500 kDa, or from about 50 kDa to about 100 kDa, or from about 100 kDa to about 2000 kDa, or from about 100 kDa to about 1000 kDa, or from about 100 kDa to about 500 kDa, or from about 500 kDa to about 2000 kDa, or from about 500 kDa to about 1000 kDa). Suitable second polymer include alginates known under the trade name Protanal, available from FMC BioPolymer, Philadelphia, Pa.

In one embodiment, the molecular weight of the second polymer is about 200-300 kDa.

The proportion of G monomeric units in an alginate molecule suitable for a composition of the present invention can be in the range from about 10 to about 90 percent of the total number of monomeric units of the alginate molecule. Alternatively, such proportion can be in the range from about 20 to about 75 (or from about 30 to about 60, or from about 25 to about 50, or from about 20 to about 50, or from about 10 to about 30) percent of the total number of monomeric units of the alginate molecule. In one embodiment, the such proportion is about 35-45 percent.

In another aspect, the oil included in a composition of the present invention is selected from the group consisting of medium-chain triglycerides (such as those having side chains having 6-12 carbons), long-chain triglycerides (such as those having side chains having 14-18 carbons), vegetable oil, peanut oil, olive oil, coconut oil, sesame oil, cottonseed oil, corn oil, sunflower oil, fish-liver oil, arachis oil, liquid paraffin, and mixtures thereof. Non-limiting examples of medium-chain triglycerides include Myritol® 312, Myritol® 318, and Myritol® 331, available from Cognis Ltd., Tokyo, Japan. Other medium-chain triglycerides are known under the names of Acomed®, Captex®, Neobee® M5F, Miglyol® 810, Miglyol® 812, Mazol®, Sefsol® 860.

In embodiments of the present invention, the oil is present in an amount from about 0.01 to about 3 percent by weight of the total composition. Alternatively, said second polymer is present in an amount from about 0.01 to about 2 percent by weight (or from about 0.01 to about 1, or from about 0.01 to about 0.5, or from about 0.01 to about 0.3, or from about 0.01 to about 0.2, or from about 0.1 to about 1, or from about 0.1 to about 0.5, or from about 0.1 to about 0.3 percent by weight, or from about 0.1 to about 0.2) of the total composition.

In another aspect, certain compositions of the present invention can further comprise a non-ionic surfactant in addition to the first polymer and the second polymer. Such a non-ionic surfactant is selected from the group consisting of Octoxynol (also known as Macrogol tetramethylbutylphenyl ether or octylphenoxy polyethoxyethanol, such as Octoxynol 1, 3, 5, 8, 9, 10, 12, 13, 16, 30, 40, 70, or other Octoxynols that comprise different numbers of repeating units of oxyethylene in the side chain), polysorbates (such as polysorbate 80 (polyoxyethylene sorbitan monooleate), polysorbate 60 (polyoxyethylene sorbitan monostearate), polysorbate 20 (polyoxyethylene sorbitan monolaurate), commonly known by their trade names of Tween® 80, Tween® 60, Tween® 20), poloxamers (synthetic block polymers of ethylene oxide and propylene oxide, such as those commonly known by their trade names of Pluronic®; e.g., Pluronic® F127 or Pluronic® F108)), or poloxamines (synthetic block polymers of ethylene oxide and propylene oxide attached to ethylene diamine, such as those commonly known by their trade names of Tetronic®; e.g., Tetronic® 1508 or Tetronic® 908, etc., other nonionic surfactants such as Brij®, Myrj®, and long chain fatty alcohols (i.e., oleyl alcohol, stearyl alcohol, myristyl alcohol, docosohexanoyl alcohol, etc.) with carbon chains having about 12 or more carbon atoms (e.g., such as from about 12 to about 24 carbon atoms). Such compounds are delineated in Martindale, $34^{th}$ ed., pp. 1411-1416 (Martindale, "The Complete Drug Reference," S. C. Sweetman (Ed.), Pharmaceutical Press, London, 2005) and in Remington, "The Science and Practice of Pharmacy," $21^{st}$ Ed., p. 291 and the contents of chapter 22, Lippincott Williams & Wilkins, New York, 2006); the contents of these sections are incorporated herein by reference. The concentration of a non-ionic surfactant, when present, in a composition of the present invention can be in the range from about 0.001 to about 5 weight percent (or alternatively, from about 0.01 to about 4, or from about 0.01 to about 3, or from about 0.01 to about 2, or from about 0.01 to about 1, or from about 0.01 to about 0.5 weight percent). In one embodiment, the non-ionic surfactant is Octoxynol 40. In another embodiment, the non-ionic surfactant is polysorbate 80.

In still another aspect, any composition of the present invention herein disclosed can further comprise a polyol.

Polyols suitable for use in a composition of the present invention include those having 2 to 18 (or, alternatively, 2 to 12, or 2 to 10, or 2 to 6, or 2 to 4) carbon atoms. In one embodiment, the polyol contains 2 to 6 carbon atoms. In another embodiment, the polyol contains 2 to 6 carbon atoms. Non-limiting examples of suitable polyols include glycerin, ethylene glycol, propylene glycol, sorbitol, mannitol, xylitol, monosaccharides, disaccharides, trisaccharides, and combinations thereof. In one embodiment, the polyol is selected from the group consisting of glycerin, ethylene glycol, propylene glycol, sorbitol, mannitol, xylitol, monosaccharides, and combinations thereof. In another embodiment, the polyol is selected from the group consisting of disaccharides. In one preferred embodiment, the polyol is a combination of glycerin and propylene glycol.

The concentration of a polyol included in a composition of the present invention is in a range from about 0.01 to about 5 percent by weight of the total composition. Alternatively, the concentration of a polyol is in a range from about 0.01 to about 3 percent (or from about 0.01 to about 2, or from about 0.01 to about 1, or from about 0.01 to about 0.5, or from about 0.05 to about 1, or from about 0.05 to about 0.6, or from about 0.1 to about 0.5, or from about 0.1 to about 1, or from about 0.1 to about 0.6, or from about 0.1 to about 0.5, or from about 0.1 to about 0.3, or from about 0.2 to about 1 percent, or from about 0.2 to about 0.6 percent) by weight of the total composition.

A composition of the present invention may contain one or more additional ingredients that are commonly present in ophthalmic solutions, for example, tonicity-adjusting agents, buffers, antioxidants, viscosity-adjusting agents, stabilizers, chelating agents, preservatives, and the like, which aid in making ophthalmic compositions more comfortable or safe to the user.

In one aspect, a composition of the present invention is free of preservatives.

In another aspect a composition of the present invention is free of alexidine, chlorhexidine, parabens, benzalkonium chloride, polymeric quaternary ammonium compounds, and derivatives thereof.

In another aspect a composition of the present invention is free of nitrogen-containing preservatives, such as alexidine, chlorhexidine, benzalkonium chloride, polymeric quaternary ammonium compounds, and derivatives thereof.

A composition of the present invention can be adjusted with tonicity-adjusting agents to approximate the tonicity of normal lacrimal fluids that is equivalent to a 0.9 percent (by weight) solution of sodium chloride or a 2.8 percent (by weight) of glycerin solution. The compositions of the present invention desirably have osmolality in a range from about 200 mOsm/kg to about 400 mOsm/ka. Alternatively, the osmolality is in the range from about 220 to about 360 mOsm/kg (or from about 220 to about 320 mOsm/kg, or from about 240 to about 300 mOsm/kg, or from about 240 to about 280 mOsm/kg, or from about 220 to about 280 mOsm/kg, or from about 220 to about 260 mOsm/kg).

In another aspect, a composition of the present invention can comprise a buffering agent or system. Suitable buffers for use in compositions of the present invention include Good's buffers. Non-limiting examples of buffering agents include MES (2-(N-morpholino)ethanesulfonic acid hemisodium salt) having pKa of 6.1 at 25° C. and pH in the range of about 5.5-6.7; HEPES (N-{2-hydroxyethyl}peperazine-N'-{2-ethanesulfonic acid}) having $pK_a$ of 7.5 at 25° C. and pH in the range of about 6.8-8.2; BES (N,N-bis{2-hydroxyethyl}2-aminoethanesulfonic acid) having $pK_a$ of 7.1 at 25° C. and pH in the range of about 6.4-7.8; MOPS (3-{N-morpholino}propanesulfonic acid) having $pK_a$ of 7.2 at 25° C. and pH in the range of about 6.5-7.9; BIS-TRIS (bis(2-hydroxyethyl)amino-tris(hydroxymethyl)methane) having $pK_a$ of 6.5 at 25° C. and pH in the range of about 5.8-7.2; citrate buffer (pH in the range of about 5.5-7.2); maleate buffer (pH in the range of about 5.5-7.2); succinate buffer (pH in the range of about 5.5-6.5); and malate buffer (pH in the range of about 4-6). Other pharmaceutically acceptable buffers that provide pH in the range of 5 to 7.5 also can be used.

A composition of the present invention can have a viscosity in the range from about 2 to about 2,000 centipoises ("cP") or mPa·s (or alternatively, from about 2 to about 1,500, or from about 2 to about 1,000, or from about 5 to about 2,000, or from about 2 to about 1,500, or from about 2 to about 1,000, or from about 10 to about 2,000, or from about 10 to about 1,500, or from about 10 to about 1,000, or from about 50 to about 2,000, or from about 50 to about 1,500, or from about 50 to about 1,000, or from about 100 to about 2,000, or from about 100 to about 1,500, or from about 100 to about 1,000 cP or mPa·s). Viscosity is measured or determined by the method disclosed hereinabove.

The use of viscosity enhancing agents to provide the compositions of the invention with viscosities greater than the viscosity of simple aqueous solutions may be desirable, in certain embodiments, to further increase the retention time of a composition in the eye. Such viscosity enhancing agents include, for example, polyvinyl alcohol, polyvinyl pyrrolidone, methyl cellulose, hydroxypropylmethyl cellulose, hydroxyethyl cellulose, carboxymethyl cellulose, or hydroxypropyl cellulose. Such agents are typically employed at a level of from 0.01 to 10 percent (alternatively, 0.1 to 5 percent, or 0.1 to 2 percent, or 0.1 to 1 percent, or 0.1 to 0.5 percent) by weight.

In some embodiments, it may be desirable to include an anti-oxidant in a composition of the present invention. Suitable anti-oxidants include, but are not limited to, ascorbic acid and its esters, sodium bisulfite, butylated hydroxytoluene, butylated hydroxyanisole, tocopherols, and combinations thereof. Antioxidants can be included in a composition of the present invention in an amount in the range from about 0.005 to about 0.5 percent by weight (or alternatively, from about 0.005 to about 0.1 percent, or from about 0.005 to about 0.05 percent, from about 0.005 to about 0.02 percent, or from about 0.005 to about 0.01 percent, by weight).

In one aspect, a composition of the present invention comprises an emulsion which comprises, consists of, or consists essentially of: (a) a first polymer, a viscosity of which changes in response to a change in concentration of an electrolyte, such as a salt, added to said first polymer; (b) a second polymer that is different from the first polymer and that comprises a polyanionic polysaccharide; (c) an oil; (d) a non-ionic surfactant; (e) a buffer; and (f) water; wherein the emulsion comprises an oil phase-in-aqueous phase emulsion, and the emulsion is stable on storage but breaks up into separate aqueous and oil phases when diluted with tear resident in an eye. Further, the composition can break up into separate aqueous and oil phases when diluted with tear resident in the eye and subject to shear stress. In one embodiment, the first polymer comprises a non-crosslinked or crosslinked polymer or copolymer of acrylic acid, and the second polymer comprises a polyanionic polysaccharide.

In another aspect, a composition of the present invention comprises an emulsion which comprises, consists of, or consists essentially of: (a) a first polymer, a viscosity of which changes in response to a change in concentration of an electrolyte, such as a salt, added to said first polymer; (b) a second polymer that is different from the first polymer and that comprises a polyanionic polysaccharide; (c) an oil; (d) a non-ionic surfactant; (e) a buffer; (f) a preservative; and (g) water; wherein the emulsion comprises an oil phase-in-aqueous phase emulsion, and the emulsion is stable on storage but breaks up into separate aqueous and oil phases under shear stress. In one embodiment, the first polymer comprises a non-crosslinked or crosslinked polymer or copolymer of acrylic acid, and the second polymer comprises a polyanionic polysaccharide.

In still another aspect, a composition of the present invention comprises an emulsion which comprises, consists of, or consists essentially of: (a) a first polymer, a viscosity of which changes in response to a change in concentration of an electrolyte, such as a salt, added to said first polymer; (b) a second polymer that is different from the first polymer and that comprises a polyanionic polysaccharide; (c) an oil; (d) a non-ionic surfactant; (e) a buffer; (f) a preservative; (g) a viscosity-adjusting agent; and (h) water; wherein the emulsion comprises an oil phase-in-aqueous phase emulsion, and the emulsion is stable on storage but breaks up into separate aqueous and oil phases under shear stress. In one embodiment, the first polymer comprises a non-crosslinked or crosslinked polymer or copolymer of acrylic acid, and the second polymer comprises a polyanionic polysaccharide.

The present invention also provides a method of ameliorating, reducing, treating, or preventing a condition of dry eye. The method comprises administering to an affected eye any one of the compositions herein disclosed.

In one embodiment, the method comprises administering to an affected eye a composition that comprises: (a) a first polymer, a viscosity of which changes with a change in a concentration of an electrolyte, such as a salt, when added to said first polymer or a composition comprising said first polymer; (b) a second polymer that is different from the first polymer; and (c) an oil.

In another embodiment, the method comprises administering to an affected eye a composition that comprises: (a) a first polymer, a viscosity of which changes with a change in a concentration of a concentration of an electrolyte, such as a salt, when added to said first polymer; (b) a second polymer that is different from the first polymer and that can modify the viscosity of the first polymer; and (c) an oil selected from triglycerides.

In yet another embodiment, the method comprises administering to an affected eye a composition that comprises: (a) a first polymer, a viscosity of which changes with a change in a concentration of a concentration of an electrolyte, such as a salt, when added to said first polymer or a composition comprising said first polymer; (b) a second polymer that is different from the first polymer and that can modify the viscosity of the first polymer; and (c) an oil selected from triglycerides.

In a further embodiment, the method comprises administering to an affected eye a composition that comprises: (a) a first polymer, a viscosity of which changes with a change in a concentration of an electrolyte, such as a salt, when added to said first polymer; (b) a second polymer that is different from the first polymer; (c) an oil; and (d) a non-ionic surfactant.

In a further embodiment, the method comprises administering to an affected eye a composition that comprises: (a) a first polymer, a viscosity of which changes with a change in a concentration of an electrolyte, such as a salt, when added to said first polymer or a composition comprising said first polymer; (b) a second polymer that is different from the first polymer; (c) an oil; and (d) a non-ionic surfactant.

In still another embodiment, the method comprises administering to an affected eye a composition that comprises an emulsion which comprises: (a) a first polymer, a viscosity of which changes with a change in a concentration of a concentration of an electrolyte, such as a salt, when added to said first polymer; (b) a second polymer that is different from the first polymer; and (c) an oil.

In still another embodiment, the method comprises administering to an affected eye a composition that comprises an emulsion which comprises: (a) a first polymer, a viscosity of which changes with a change in a concentration of a concentration of an electrolyte, such as a salt, when added to said first polymer or a composition comprising said first polymer; (b) a second polymer that is different from the first polymer; and (c) an oil selected from the group consisting of medium-chain triglycerides.

In still another embodiment, the method comprises administering to an affected eye a composition that comprises an emulsion which comprises: (a) a first polymer, a viscosity of which changes with a change in a concentration of concentration of an electrolyte, such as a salt, when added to said first polymer or a composition comprising said first polymer; (b) a second polymer that is different from the first polymer; (c) an oil selected from the group consisting of medium-chain triglycerides; (d) a non-ionic surfactant; and (e) water. In one embodiment, the viscosity of the viscosity decreases with an increase in the concentration of the salt.

In still another embodiment, the method comprises administering to an affected eye a composition that comprises an emulsion which comprises: (a) a first polymer, a viscosity of which changes with a change in a concentration of a concentration of an electrolyte, such as a salt, when added to said first polymer or a composition comprising said first polymer; (b) a second polymer that is different from the first polymer; (c) an oil selected from the group consisting of medium-chain triglycerides; (d) a non-ionic surfactant; and (e) water; wherein the composition has a pH in a range from about 5 to about 7.5. In one embodiment, the composition has a pH in the range from about 5.5 to about 7.5. In another embodiment, the composition has a pH in the range from about 6 to about 7.5 (or alternatively, from about 6 to about 7, or from about 5.5 to about 7, or from about 5.5 to about 6.5). In one embodiment, the viscosity of the viscosity decreases with an increase in the concentration of the salt.

In still another embodiment, the method comprises administering to an affected eye a composition that comprises an emulsion which comprises: (a) a first polymer, a viscosity of which changes with a change in a concentration of a concentration of an electrolyte, such as a salt, when added to said first polymer or a composition comprising said first polymer; (b) a second polymer that is different from the first polymer; (c) an oil selected from the group consisting of medium-chain triglycerides; (d) a non-ionic surfactant; and (e) a polyols; wherein the composition has a pH in a range from about 5 to about 7.5. In one embodiment, the viscosity of the viscosity decreases with an increase in the concentration of the salt.

In one aspect, the various ingredients of the composition are present in amounts disclosed herein.

In another aspect, the composition can be applied in one or more drops to an ocular surface once per day, twice per day, or three or more times per day, as needed.

In still another aspect, the method provides relief to an ocular discomfort resulting from a dry eye condition.

In a further aspect, the present invention provides a method for producing a composition for ameliorating, reducing, treating, or preventing a condition of dry eye. The method comprises combining: (a) a first polymer, a viscosity of which changes with a change in a concentration of an electrolyte, such as a salt, when added to said first polymer or a composition comprising said first polymer; (b) a second polymer that is different from the first polymer; and (c) an oil, to produce said composition.

In a still another aspect, the present invention provides a method for producing a composition for ameliorating, reducing, treating, or preventing a condition of dry eye. The method comprises combining: (a) a first polymer, a viscosity of which changes with a change in a concentration of an electrolyte, such as a salt, when added to said first polymer or a composition comprising said first polymer; (b) a second polymer that is different from the first polymer; (c) an oil; and (d) a non-ionic surfactant, to produce said composition.

In a yet another aspect, the present invention provides a method for producing a composition for ameliorating, reducing, treating, or preventing a condition of dry eye. The method comprises combining: (a) a first polymer, a viscosity of which changes with a change in a concentration of an electrolyte, such as a salt, when added to said first polymer or a composition comprising said first polymer; (b) a second polymer that is different from the first polymer; (c) an oil; and (d) a non-ionic surfactant, to produce said composition; wherein a pH of the mixture has a value in a range from about 5 to about 7.5 (or alternatively, from about 5 to 7, or from about 5.5 to 7, or from about 5 to 6, or from about 5.5. to 6.5).

In still another aspect, the step of combining further includes adding a polyol into said mixture. Suitable polyols and their concentrations are disclosed hereinabove.

In yet another aspect, the method further comprises: (b) adjusting the pH value of the mixture to bring it into said pH range.

In a further aspect, the method further comprises: (c) subjecting the mixture to a sterilization procedure. In one embodiment, the sterilization procedure can comprise exposing the mixture to $\alpha$, $\beta$, or $\gamma$ radiation; autoclaving the mixture; or heating the mixture to a temperature in arrange from about 100 to about 125° C., for 10 minutes or longer, but less than a time that would result in a degradation of the alginate.

A composition of the present invention may be packaged in unit-dose (for single use) or multi-dose (for multiple use) containers.

Tables 1-3 show exemplary compositions of the present invention. Some compositions within the scope of the preferred compositions were prepared and tested.

TABLE 1

Some Compositions of the Present Invention for Treating or Alleviating Dry Eye Condition

| Ingredient | Concentration (percent by weight, unless otherwise indicated) | | | |
| --- | --- | --- | --- | --- |
| | Range 1 | Range 2 | Range 3 | Preferred Embodiment |
| Carbomer 980 NF | 0.05-0.5 | 0.05-0.4 | 0.1-0.3 | 0.2 |
| Sodium hyaluronate | 0.01-0.5 | 0.05-0.4 | 0.07-0.2 | 0.15 |
| Myritol 318 (medium-chain triglyceride) | 0.05-1 | 0.1-0.8 | 0.2-0.7 | 0.5 |
| Propylene glycol | 0.05-1 | 0.1-0.8 | 0.3-0.7 | 0.55 |
| Glycerin | 0.05-1 | 0.1-0.8 | 0.3-0.7 | 0.55 |
| $C_{12}$ amine oxide (ppm) (preservative) | 0-150 | 0-100 | 0-70 | 0 |
| Octoxynol 40 | 0-0.1 | 0-0.08 | 0-0.06 | 0 |
| Boric acid | 0.01-1 | 0.1-0.8 | 0.2-0.6 | 0.45 |
| Sodium borate heptahydrate | 0.01-1 | 0.05-0.5 | 0.1-0.25 | 0.15 |
| Sodium chlorite (ppm) | 0-500 | 0-300 | 0-250 | 0 |
| Hydrogen peroxide (ppm) | 0-500 | 0-300 | 0-250 | 0 |
| Sorbic acid | 0-1 | 0-0.8 | 0-0.3 | 0 |
| Purified water | q.s. to 100 | q.s. to 100 | q.s. to 100 | q.s. to 100 |
| Emulsion stability | Stable | Stable | Stable | Stable |
| pH | 5-8 | 5.5-7.5 | 6-7.5 | 7-7.3 |
| Osmolality (mOsm/kg) | 200-350 | 210-320 | 220-280 | 230-240 |
| Viscosity (cP)[1] | 100-1500 | 300-1000 | 500-900 | 760-775 |

Note:
[1] measured with CPE-52 spindle at shear rate of 15 sec$^{-1}$

TABLE 2

Some Compositions of the Present Invention for Treating or Alleviating Dry Eye Condition

| Ingredient | Concentration (percent by weight, unless otherwise indicated) | | | |
| --- | --- | --- | --- | --- |
| | Range 1 | Range 2 | Range 3 | Preferred Concentration |
| Carbomer 980 NF | 0.05-0.5 | 0.05-0.4 | 0.1-0.3 | 0.1 |
| Glucuronoxylomannan extracted from the *Tremella fuciformis* | 0.01-0.5 | 0.05-0.4 | 0.07-0.2 | 0.1 |
| Myritol 318 (medium-chain triglyceride) | 0.05-1 | 0.1-0.8 | 0.2-0.7 | 0.5 |
| Propylene glycol | 0.05-1 | 0.1-0.8 | 0.3-0.7 | 0.55 |
| Glycerin | 0.05-1 | 0.1-0.8 | 0.3-0.7 | 0.55 |
| $C_{12}$ amine oxide (preservative) | 0-150 | 0-100 | 0-70 | 50 |
| Octoxynol 40 | 0-0.1 | 0-0.08 | 0-0.06 | 0.01 |
| Boric acid | 0.01-1 | 0.1-0.8 | 0.2-0.6 | 0.45 |
| Sodium borate heptahydrate | 0.01-1 | 0.05-0.5 | 0.1-0.25 | 0.15 |
| Sodium chlorite (ppm) | 0-500 | 0-300 | 0-250 | 200 |
| Hydrogen peroxide (ppm) | 0-500 | 0-300 | 0-250 | 0 |
| Sorbic acid | 0-1 | 0-0.8 | 0-0.3 | 0 |
| Purified water | q.s. to 100 | q.s. to 100 | q.s. to 100 | q.s. to 100 |
| Emulsion stability | Stable | Stable | Stable | Stable |
| pH | 5-8 | 5.5-7.5 | 6-7.5 | 7-7.3 |
| Osmolality (mOsm/kg) | 200-350 | 210-320 | 220-280 | 230-240 |
| Viscosity (cP)[1] | 50-1500 | 80-1000 | 90-600 | 90-120 |

Note:
[1] measured with CPE-52 spindel at shear rate of 15 sec$^{-1}$

TABLE 3

Some Compositions of the Present Invention for Treating or Alleviating Dry Eye Condition

| Ingredient | Range 1 | Range 2 | Range 3 | Preferred Concentration |
|---|---|---|---|---|
| Carbomer 980 NF | 0.05-0.5 | 0.05-0.4 | 0.1-0.3 | 0.1 |
| Sodium alginate (AIC F-200) | 0.01-0.5 | 0.05-0.4 | 0.07-0.3 | 0.2 |
| Myritol 318 (medium-chain triglyceride) | 0.05-1 | 0.1-0.8 | 0.2-0.7 | 0.5 |
| Propylene glycol | 0.05-1 | 0.1-0.8 | 0.3-0.7 | 0.55 |
| Glycerin | 0.05-1 | 0.1-0.8 | 0.3-0.7 | 0.55 |
| $C_{12}$ amine oxide (ppm) (preservative) | 0-150 | 0-100 | 0-70 | 50 |
| Octoxynol 40 | 0-0.1 | 0-0.08 | 0-0.06 | 0.01 |
| Boric acid | 0.01-1 | 0.1-0.8 | 0.2-0.6 | 0.45 |
| Sodium borate heptahydrate | 0.01-1 | 0.05-0.5 | 0.1-0.25 | 0.15 |
| Sodium chlorite (ppm) | 0-500 | 0-300 | 0-250 | 0 |
| Hydrogen peroxide (ppm) | 0-500 | 0-300 | 0-250 | 0 |
| Sorbic acid | 0-1 | 0-0.8 | 0-0.3 | 0.2 |
| Purified water | q.s. to 100 | q.s. to 100 | q.s. to 100 | q.s. to 100 |
| Emulsion stability | Stable | Stable | Stable | Stable |
| pH | 5-8 | 5.5-7.5 | 6-7.5 | 6-6.53 |
| Osmolality (mOsm/kg) | 200-350 | 210-320 | 220-280 | 250-270 |
| Viscosity (cP)[1] | 5-1000 | 10-600 | 10-300 | 10-30 |

Note:
[1] measured with CPE-52 spindel at shear rate of 15 sec$^{-1}$

Table 4 shows some other exemplary compositions within the scope of the present invention that have not been experimentally prepared. These compositions also are expected to have utility in providing relief to a dry eye condition.

TABLE 4

Some Additional Compositions for Treating or Alleviating Dry Eye Condition

| Type of Ingredient | Example 1 Ingredient | (wt. %) | Example 2 Ingredient | (wt. %) |
|---|---|---|---|---|
| First Polymer | Carbomer 971P NF | 0.2 | Carbomer 940 NF | 0.1 |
| Second Polymer | Protanal LF 240D[1] | 0.3 | Sodium hyaluronate | 0.1 |
| Oil | Myritol® 312 | 0.6 | Coconut oil | 0.5 |
| Buffer | MES | 1 | Succinate | 1.5 |
| Viscosity-modifying agent | None | 0 | Carboxymethyl-cellulose | 0.05 |
| Polyol | Glycerin | 0.6 | Glycerin | 1 |
| Additional polyol | Propylene glycol | 0.6 | none | 0 |
| Preservative | Sodium chlorite | 100 ppm | Poly-quaternium-1 | 10 ppm |
| Surfactant | Polysorbate 80 | 0.05 | None | 0 |
| pH adjuster | HCl or NaOH | q.s. for pH adjustment to 6.5-7.5 | HCl or NaOH | q.s. for pH adjustment to 6.5-7.5 |
| Purified water | q.s. 100 | q.s. 100 | q.s. 100 | q.s. 100 |
| Viscosity (cP) | — | 600-900 | — | 600-900 |

Note:
[1] sodium alginate from FMC BioPolymer, G/M ratio of 30-35/65-70, viscosity of 7-150 mPa·s.

TABLE 5

Some Additional Compositions of the Present Invention for Treating or Alleviating Dry Eye Condition

| Ingredient | Example 3 | Example 4 | Example 5 | Example 6 |
|---|---|---|---|---|
| Carbomer 980 NF | 0.1 | 0.1 | 0.1 | 0.05 |
| Sodium alginate | 0 | 0.25 | 0 | 0.25 |
| Sodium hyaluronate | 0.1 | 0 | 0 | 0 |
| Glucuronoxylomannan extracted from the mushroom Tremella fuciformis | 0 | 0 | 0.1 | 0.25 |
| Myritol 318 (medium-chain triglyceride) | 0.5 | 0.5 | 0.5 | 0 |
| Propylene glycol $C_8/C_{10}$ fatty acid diester | 0 | 0 | 0 | 0.5 |
| Propylene glycol | 0.74 | 0.55 | 0.55 | 0.55 |
| Glycerin | 0.3 | 0.55 | 0.55 | 0.55 |
| $C_{12}$ amine oxide (ppm) (preservative) | 166 | 166 | 166 | 0 |
| Octoxynol 40 | 0.0143 | 0.0143 | 0.0143 | 0 |
| Cremophor EL (surfactant) | 0 | 0 | 0 | 0.015 |
| Boric acid | 0.45 | 0.2 | 0.45 | 0.2 |
| Sodium borate | 0.15 | 0.08 | 0.15 | 0.07 |
| Purified water | q.s. to 100 | q.s. to 100 | q.s. to 100 | q.s. to 100 |
| pH | 5.5-7.5 | 5.5-7.5 | 5.5-7.5 | 5.5-7.5 |

TABLE 6

Some Additional Compositions of the Present Invention for Treating or Alleviating Dry Eye Condition

| INGREDIENTS | Example 7 Notebook Number 3089-ZTM-158 | Example 8 3089-ZTM-159-1 | Example 9 3089-ZTM-159-2 | Example 10 3089-ZTM-159-3 | Example 11 3089-ZTM-160-1 | Example 12 3089-ZTM-160-2 |
|---|---|---|---|---|---|---|
| Carbomer 980 NF | 0.1 | 0.1 | 0.1 | 0.1 | 0.1 | 0.1 |
| Triglycerides, medium chain | 1.0 | 0.0 | 0.0 | 0.0 | 0.0 | 0.0 |
| Light Mineral Oil NF | 0.0 | 1.0 | 0.0 | 0.0 | 0.0 | 0.0 |
| Squalane | 0.0 | 0.0 | 1.0 | 0.0 | 0.0 | 0.0 |
| Olive Oil, NF | 0.0 | 0.0 | 0.0 | 0.0 | 1.0 | 0.0 |
| PEG 75 Lanolin | 0.0 | 0.0 | 0.0 | 1.0 | 0.0 | 0.0 |

TABLE 6-continued

Some Additional Compositions of the Present Invention for Treating or Alleviating Dry Eye Condition

| | Example | | | | | |
|---|---|---|---|---|---|---|
| | 7 | 8 | 9 | 10 | 11 | 12 |
| | Notebook Number | | | | | |
| INGREDIENTS | 3089-ZTM-158 | 3089-ZTM-159-1 | 3089-ZTM-159-2 | 3089-ZTM-159-3 | 3089-ZTM-160-1 | 3089-ZTM-160-2 |
| | Concentration (wt %) | | | | | |
| PG Diester $C_8/C_{10}$ | 0.0 | 0.0 | 0.0 | 0.0 | 0.0 | 1.0 |
| Sorbitol | 4.0 | 4.0 | 4.0 | 4.0 | 4.0 | 4.0 |
| Na Alginate | 0.2 | 0.2 | 0.2 | 0.2 | 0.2 | 0.2 |
| Lauramine oxide, ppm | 100 | 100 | 100 | 100 | 100 | 100 |
| Sodium Phosphate, dibasic anhydrous | 0.04 | 0.04 | 0.04 | 0.04 | 0.04 | 0.04 |
| Purified water | q.s. to 100 | q.s. to 100 | q.s. to 100 | q.s. to 100 | q.s. to 100 | q.s. to 100 |

TABLE 7

Some Additional Compositions for Treating or Alleviating Dry Eye Condition

| | Example | | | |
|---|---|---|---|---|
| Type of Ingredient | 13 | | 14 | |
| | Ingredient | (wt. %) | Ingredient | (wt. %) |
| First Polymer | Carbomer 71G NF | 0.2 | Carbomer 940 NF | 0.1 |
| Second Polymer | Protanal LF 240D [1] | 0.2 | Sodium hyaluronate | 0.2 |
| Oil | Myritol® 331 | 0.6 | Peanut oil | 0.5 |
| Buffer | citrate | 1 | Succinate | 1 |
| Viscosity-modifying agent | Hydroxypropylmethyl cellulose | 0.07 | Carboxymethylcellulose | 0.05 |
| Polyol | Glycerin | 0.6 | Glycerin | 0 |
| Additional polyol | Propylene glycol | 0.6 | none | 0.7 |
| Preservative | Sodium chlorite | 100 ppm | Polyquaternium-1 | 10 ppm |
| Surfactant | Polysorbate 20 | 0.05 | Octoxynol-70 | 0.01 |
| pH adjuster | HCl or NaOH | q.s. for pH adjustment to 6.5-7.5 | HCl or NaOH | q.s. for pH adjustment to 6.5-7.5 |
| Purified water | q.s. 100 | q.s. 100 | q.s. 100 | q.s. 100 |
| Viscosity (cP) | — | 600-900 | — | 600-900 |

Note:
[1] sodium alginate from FMC BioPolymer, G/M ratio of 35-45/55-65, viscosity of 7-150 mPa·s.

A composition of the present invention may be produced by a method described below. Some basic steps or procedures used in the method are known in the art.

In an appropriate mixing vessel equipped with temperature control and mixing equipment, add a volume purified water equivalent to 85-90 percent of the total batch weight. With continued agitation, slowly add the polymers.

With continued agitation, add the remaining ingredients except the lipid. Mix well.

Add sodium hydroxide or hydrochloric acid for pH adjustment.

Slowly add the lipid while vigorously stirring to ensure homogeneity and reduction of oil droplet size.

Add purified water to obtain the final batch weight. Mix well.

The composition is heat sterilized.

A composition of the present invention may also be produced by an alternative method described immediately below.

In an appropriate mixing vessel equipped with temperature control and mixing equipment, add a volume of purified water equivalent to about 40% of the desired total batch weight.

With continued agitation, dissolve in an appropriate vessel the batch quantities of the following ingredients: polymer (other than a carbomer or carboxyvinyl polymers), osmolytes, surfactant, and optionally other desirable additives. This is called the first mixture.

Sterile filter or heat sterilize the first mixture.

Aseptically transfer the desired quantity of the oil (sterile filtered or heat sterilized) to the first mixture. Homogenize at 50-60° C. the mixture to form an emulsion.

In an appropriate mixing vessel equipped with temperature control and mixing equipment, add a volume of purified water equivalent to about 40% of the desired total batch weight.

With continued agitation, slowly add the desired batch quantities of a carbomer (or a polyacrylic acid). and mix well to hydrate the carbomer or polyacrylic acid.

With continued agitation, slowly add to the vessel the desired batch quantities of the remaining ingredients such as buffer, chelating agent, etc.

Heat sterilize the mixture using procedures known in the art, such as pharmaceutical art.

Allow solution to cool to (≦45° C.), and combine the emulsion solution with carbomer phase.

While mixing, adjust the pH to the desired value with NaOH (or HCl solution).

Bring the batch to the desired weight (100% w/w) with purified water

In one embodiment, a composition for reducing, ameliorating, treating, or preventing a condition of dry eye, the composition consists or consists essentially of: (a) a carboxyvinyl polymer at a concentration from about 0.1 to about 0.5 percent by weight of the total composition; (b) a polysaccharide at a concentration from about 0.05 to about 0.5 percent by weight of the total composition; (c) a medium-chain triglyceride at a concentration from about 0.2 to about 0.5 percent by weight of the total composition; (d) a non-ionic surfactant at a concentration from about 0.01 to about 0.5 percent by weight of the total composition; and (e) a polyols selected from the group consisting of glycerin, propylene glycol, and mixture thereof, at a concentration from about 0.1 to about 1 percent by weight of the total composition; and (d) water; wherein the composition is a stable emulsion in storage and has a pH from about 5.5 to about 7.5.

In another embodiment, a composition for reducing, ameliorating, treating, or preventing a condition of dry eye, the composition consists or consists essentially of: (a) a carboxyvinyl polymer at a concentration from about 0.1 to about 0.5 percent by weight of the total composition; (b) a polysaccharide at a concentration from about 0.05 to about 0.5 percent by weight of the total composition; (c) a medium-chain triglyceride at a concentration from about 0.2 to about 0.5 percent by weight of the total composition; (d) a non-ionic surfactant at a concentration from about 0.01 to about 0.5 percent by weight of the total composition; and (e) a polyols selected from the group consisting of glycerin, propylene glycol, and mixture thereof, at a concentration from about 0.1 to about 1 percent by weight of the total composition; and (d) boric acid and borate buffer; wherein the composition is a stable emulsion in storage and has a pH from about 7 to about 7.5.

In still another embodiment, a composition for reducing, ameliorating, treating, or preventing a condition of dry eye, the composition consists or consists essentially of: (a) a carboxyvinyl polymer selected from the group consisting of carbomers, polycarbophil, and mixtures thereof, at a concentration from about 0.1 to about 0.5 percent by weight of the total composition; (b) a polysaccharide selected from the group consisting of sodium alginate, sodium hyaluronate, glucuronoxylomannan, and mixtures thereof, at a concentration from about 0.05 to about 0.5 percent by weight of the total composition; (c) a medium-chain triglyceride at a concentration from about 0.2 to about 0.5 percent by weight of the total composition; (d) a non-ionic surfactant selected from the group consisting of Octoxynols and polysorbates at a concentration from about 0.01 to about 0.5 percent by weight of the total composition; and (e) a polyols selected from the group consisting of glycerin, propylene glycol, and mixture thereof, at a concentration from about 0.1 to about 1 percent by weight of the total composition; and (f) boric acid and borate buffer; wherein the composition is a stable emulsion in storage and has a pH from about 7 to about 7.5.

In still another embodiment, a composition for reducing, ameliorating, treating, or preventing a condition of dry eye, the composition consists or consists essentially of: (a) a carboxyvinyl polymer selected from the group consisting of carbomers, polycarbophil, and mixtures thereof, at a concentration from about 0.1 to about 0.5 percent by weight of the total composition; (b) a polysaccharide selected from the group consisting of sodium alginate, sodium hyaluronate, glucuronoxylomannan, and mixtures thereof, at a concentration from about 0.05 to about 0.5 percent by weight of the total composition; (c) a medium-chain triglyceride at a concentration from about 0.2 to about 0.5 percent by weight of the total composition; (d) a non-ionic surfactant selected from the group consisting of Octoxynols and polysorbates at a concentration from about 0.01 to about 0.5 percent by weight of the total composition; (e) a polyols selected from the group consisting of glycerin, propylene glycol, and mixture thereof, at a concentration from about 0.1 to about 1 percent by weight of the total composition; (f) boric acid and borate buffer; and (g) a material selected from the group consisting of chelating agents, preservatives, anti-oxidants, and mixtures thereof; wherein the composition is a stable emulsion in storage and has a pH from about 7 to about 7.5.

Compositions of the present invention are in contrast to prior-art emulsion eye drops, which tend to remain as stable emulsions when placed on the eye. Compositions of the present invention are stable oil-in-water emulsions on storage, but break up into separate oil and water phases upon being instilled on the ocular surface and subject to natural eye blinks. While Applicants do not wish to be bound by any one particular theory, Applicants believe that the thus-generated separate oil phase forms an oil layer over the water layer of the tear film and serves to reduce the evaporation rate from the surface of the eye. The oil can also serve to augment a pathological condition of low lipid concentration in the tear film of certain dry eye patients, such as those suffering from the condition of dysfunctional meibomian gland. Other ingredients of a composition of the present invention also become available during the composition with the natural tear and can provide additional protection or benefits and aid in the restoration of a deficient tear film.

A technique was developed using a dispersion analyzer, known as a Lumisizer™, to assess the stability of lipid emulsion formulations when subjected to shear stress. Formulations were tested neat and in the presence of simulated tear fluid.

A technique was developed using a dispersion analyzer, known as a Lumisizer™, in an effort to gain a better understanding of the stability of lipid emulsion formulations. Formulations were tested (neat) and in the presence of simulated tear fluid.

Lumisizer™ (L. U. M. GmbH, Berlin, Germany) is a multisample analytical centrifuge that measures space and time-resolved light extinction profiles of samples that can provide information about the ease of breaking the stability of an emulsion or dispersion under shear stress. See; e.g., H-T. Chiu et al., *J. Polym. Res.*, Vol. 18, 1587 (2011); G. G. Badolato et al., *Progr. Colloid Polym. Sci.*, Vol. 134, 66 (2008); T. Detloff et al., *Powder Techn.*, Vol. 174, 50 (2007). This centrifuge enables simultaneous measurement of the intensity of transmitted light as a function of time and position over the entire sample length, as the sample is subject to centrifugal force. A stable emulsion under centrifugal force exhibits substantially constant intensity of transmitted light through the emulsion at a fixed location. On the other hand, an emulsion that is less stable under stress, such as under centrifugal force, exhibits a rapid increase in the intensity of transmitted light, as the two phases (oil and water phases) separate.

In the following study, a Lumisizer™ Model 6100-121 (12 samples capability) with SepView 6.0 software was used. Various emulsions were prepared having the compositions shown in Table 8. Each composition was added to a polycarbonate centrifuge cell having an optical path length of 2 mm. The temperature was kept constant at 37° C. Data on light transmission through a sample were acquired at 15 points along the length of each cell at 60-second interval, as the rotational speed was increased in the range of 200-1000 rpm (at increments of 100 rpm) and a final rotational speed of 2000 rpm.

TABLE 8

Polymer combinations with lipid and surfactant (two surfactant concentrations) (Notebook Number 3214TK154 and 3265-ZTM-49)

| | Formulation | | | | | | | |
|---|---|---|---|---|---|---|---|---|
| Ingredient | F1 | F2 | F3 | F4 | F5 | F6 | F7 | F8 |
| | Concentration (weight %) | | | | | | | |
| Carbomer 980 | 0.1 | 0.1 | 0.1 | 0.1 | 0.1 | 0.1 | 0 | 0 |
| Na HA | 0.1 | 0.1 | 0 | 0 | 0 | 0 | 0 | 0 |
| Na Alginate | 0 | 0 | 0.1 | 0.1 | 0 | 0 | 0 | 0 |
| TFP [(1)] | 0 | 0 | 0 | 0 | 0.1 | 0.1 | 0.3 | 0.3 |
| PEG 8000 | 0 | 0 | 0 | 0 | 0 | 0 | 1.0 | 1.0 |
| Med chain triglyceride | 0.5 | 0.5 | 0.5 | 0.5 | 0.5 | 0.5 | 0.5 | 0.5 |

TABLE 8-continued

Polymer combinations with lipid and surfactant (two surfactant concentrations) (Notebook Number 3214TK154 and 3265-ZTM-49)

| Octoxynol-40 | 0.01 | 0.98 | 0.01 | 0.98 | 0.01 | 0.98 | 0.01 | 0.98 |
|---|---|---|---|---|---|---|---|---|
| Lauramine Oxide | 0.005 | 0.02 | 0.005 | 0.02 | 0.005 | 0.02 | 0.005 | 0.02 |
| NaOH for pH adjustment | None | None | None | None | None | None | None | None |
| Water | q.s. to 100% | q.s. to 100% | q.s. to 100% | q.s. to 100% | q.s. to 100% | q.s. to 100% | q.s. to 100% | q.s. to 100% |
| Viscosity [2] (cP) | 786 | 712 | 378 | 321 | 1042 | 858 | 264 | 241 |

| | Formulation |||||||||
|---|---|---|---|---|---|---|---|---|
| Ingredient | F9 | F10 | F11 | F12 | F13 | F14 | F15 | F16 |
| | Concentration (weight %) |||||||||
| Carbomer 980 | 0.1 | 0.1 | 0.1 | 0.1 | 0.1 | 0.1 | 0 | 0 |
| Na HA | 0.1 | 0.1 | 0 | 0 | 0 | 0 | 0 | 0 |
| Na Alginate | 0 | 0 | 0.1 | 0.1 | 0 | 0 | 0 | 0 |
| TFP [1] | 0 | 0 | 0 | 0 | 0.1 | 0.1 | 0.3 | 0.3 |
| PEG 8000 | 0 | 0 | 0 | 0 | 0 | 0 | 1.0 | 1.0 |
| Med chain triglyceride | 0.5 | 0.5 | 0.5 | 0.5 | 0.5 | 0.5 | 0.5 | 0.5 |
| Tween 80 | 0.015 | 1.0 | 0.015 | 1.0 | 0.015 | 1.0 | 0.015 | 1.0 |
| NaOH for pH adjustment | None | None | None | None | None | None | None | None |
| Water | q.s. to 100% | q.s. to 100% | q.s. to 100% | q.s. to 100% | q.s. to 100% | q.s. to 100% | q.s. to 100% | q.s. to 100% |
| Viscosity (cP) | 787 | 632 | 373 | 289 | 981 | 780 | 259 | 231 |

| | Formulation |||||||||
|---|---|---|---|---|---|---|---|---|
| Ingredient | F17 | F18 | F19 | F20 | F21 | F22 | F23 | F24 |
| | Concentration (weight %) |||||||||
| Carbomer 980 | 0.1 | 0.1 | 0.1 | 0.1 | 0.1 | 0.1 | 0.2 | 0 |
| Na HA | 0.1 | 0.1 | 0 | 0 | 0 | 0 | 0.15 | 0 |
| Na Alginate | 0 | 0 | 0.1 | 0.1 | 0 | 0 | 0 | 0 |
| TFP [1] | 0 | 0 | 0 | 0 | 0.1 | 0.1 | 0.3 | 0.3 |
| PEG 8000 | 0 | 0 | 0 | 0 | 0 | 0 | 1.0 | 1.0 |
| Med chain triglyceride | 0.5 | 0.5 | 0.5 | 0.5 | 0.5 | 0.5 | 0.5 | 0.5 |
| Cremophor EL | 0.015 | 1.0 | 0.015 | 1.0 | 0.015 | 1.0 | 0.015 | 1.0 |
| NaOH for pH adjustment | None | None | None | None | None | None | None | None |
| Water | q.s. to 100% | q.s. to 100% | q.s. to 100% | q.s. to 100% | q.s. to 100% | q.s. to 100% | q.s. to 100% | q.s. to 100% |
| Viscosity [2] (cP) | 771 | 610 | 373 | 298 | 965 | 804 | 251 | 236 |

Notes:
[1] TFP is glucuronoxylomannan extracted from the mushroom species *Tremella fuciformis*.
[2] measured at 15 sec$^{-1}$ FIGS. 1-48 show light transmission data through the samples of compositions of Table 8. An emulsion is stable when the intensity of transmitted light through a sample thereof remains substantially constant under increasing rotational speed. On the other hand, an emulsion is unstable (and separates into a water layer and an oil layer) when the intensity of transmitted light through a sample thereof increases under increasing rotational speed.

Figure 2:
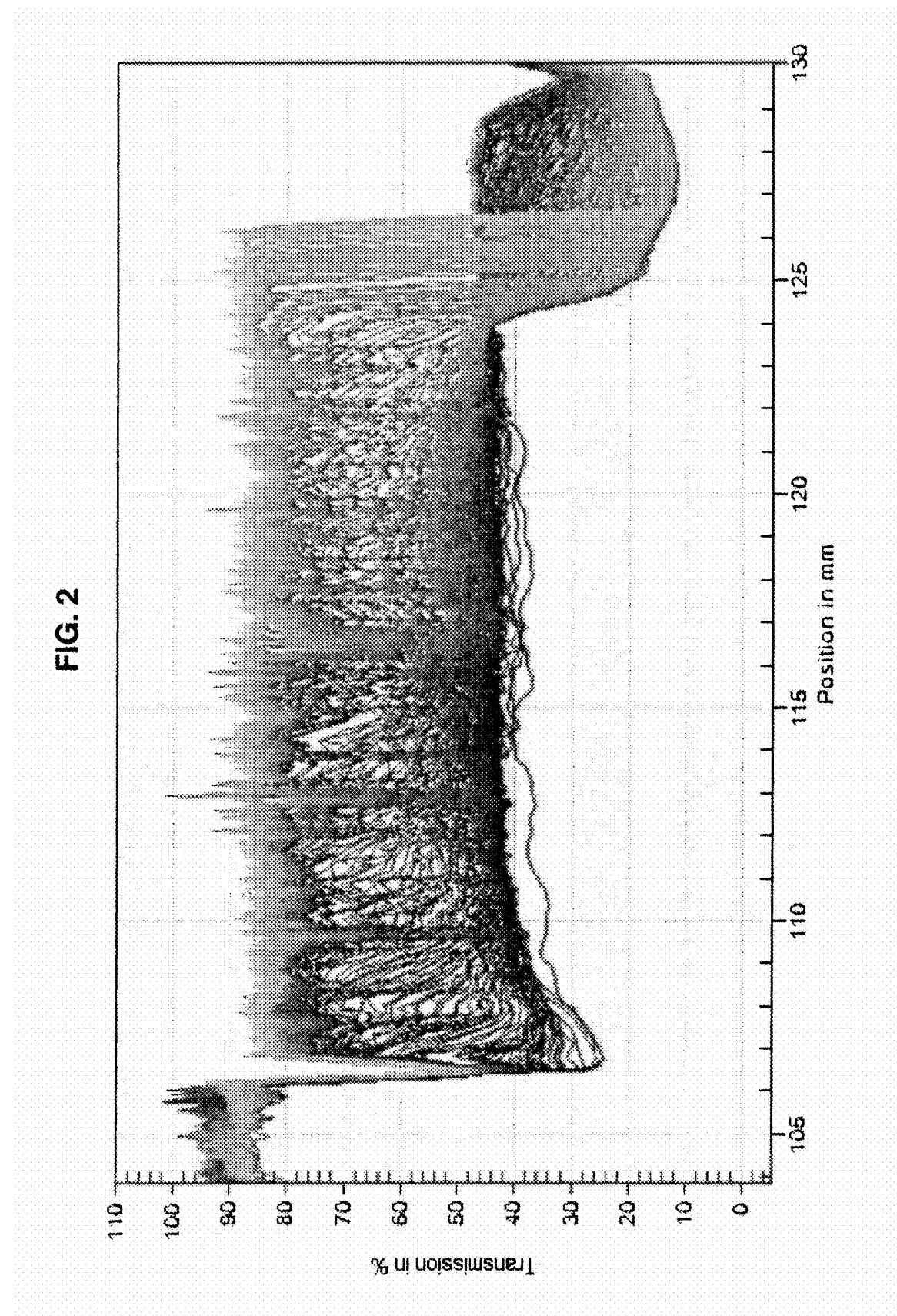
FIG. 2 shows Lumisizer™ light transmission measurement through a 1:1 mixture of Formulation F1 and HBSS (Hank balance salt solution).
Figure 3:
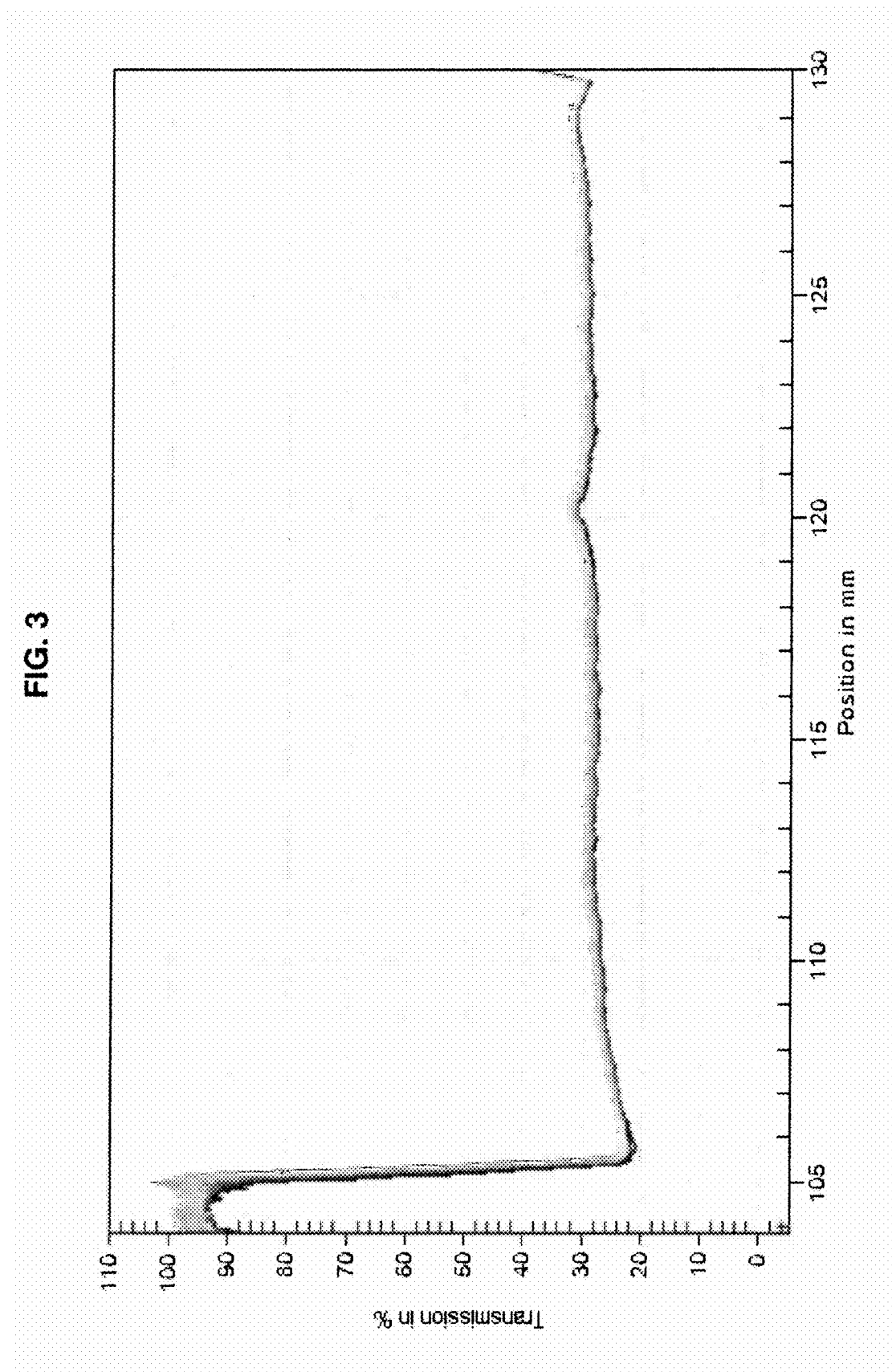
FIG. 3 shows Lumisizer™ light transmission measurement through neat Formulation F3.
Figure 4:
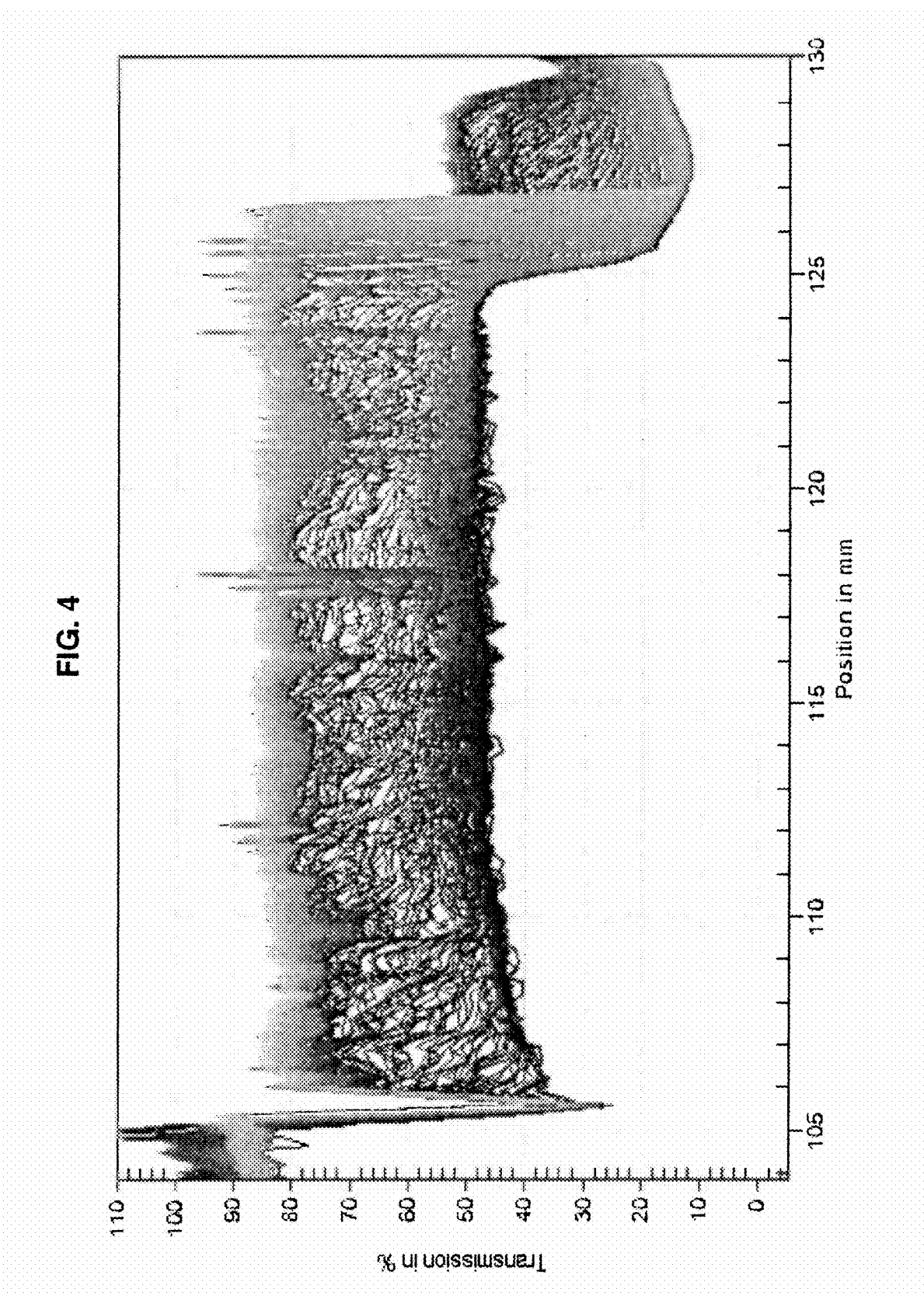
FIG. 4 shows Lumisizer™ light transmission measurement through a 1:1 mixture of Formulation F1 and HBSS.
Figure 5:
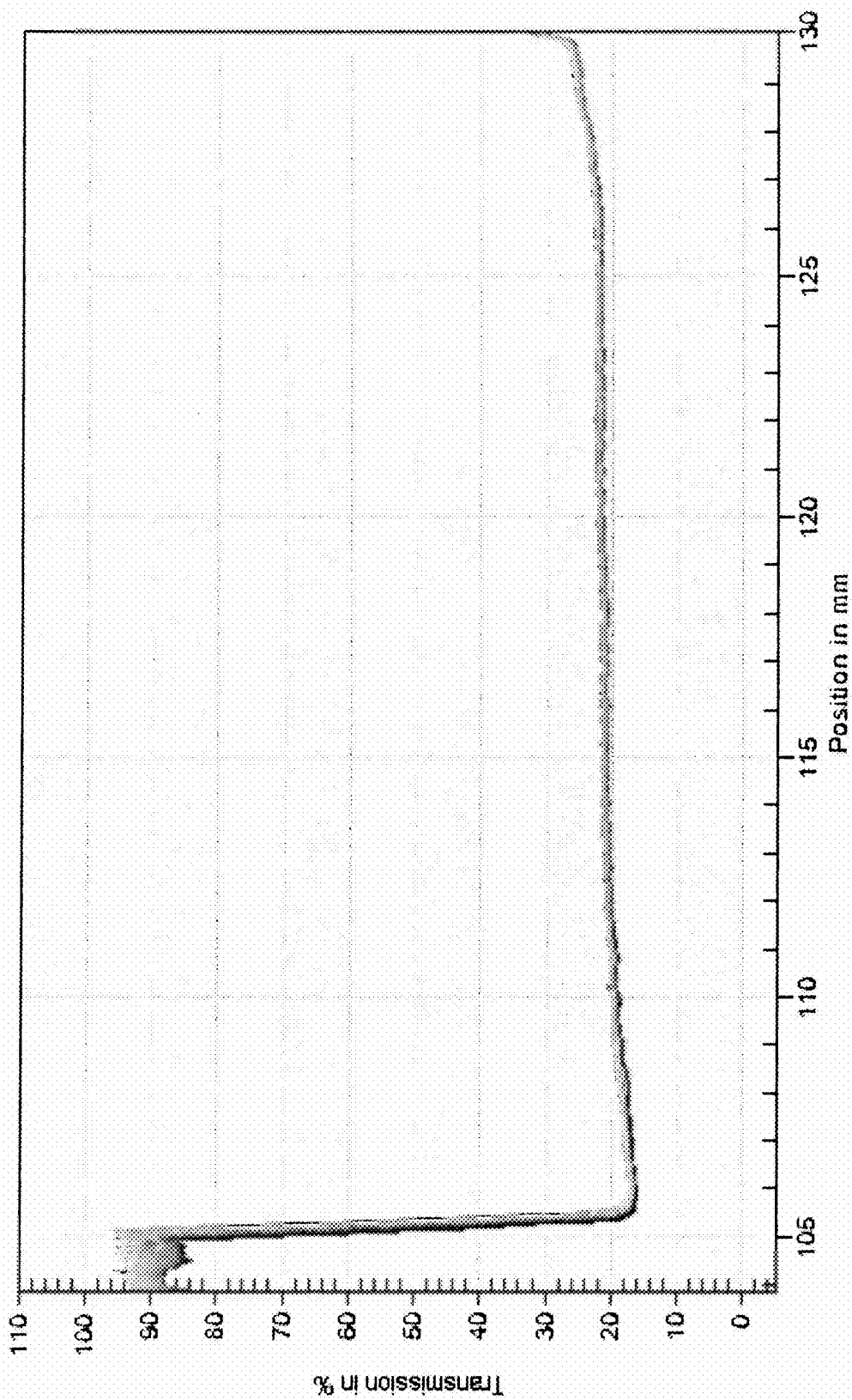
FIG. 5 shows Lumisizer™ light transmission measurement through neat Formulation F5.
Figure 6:
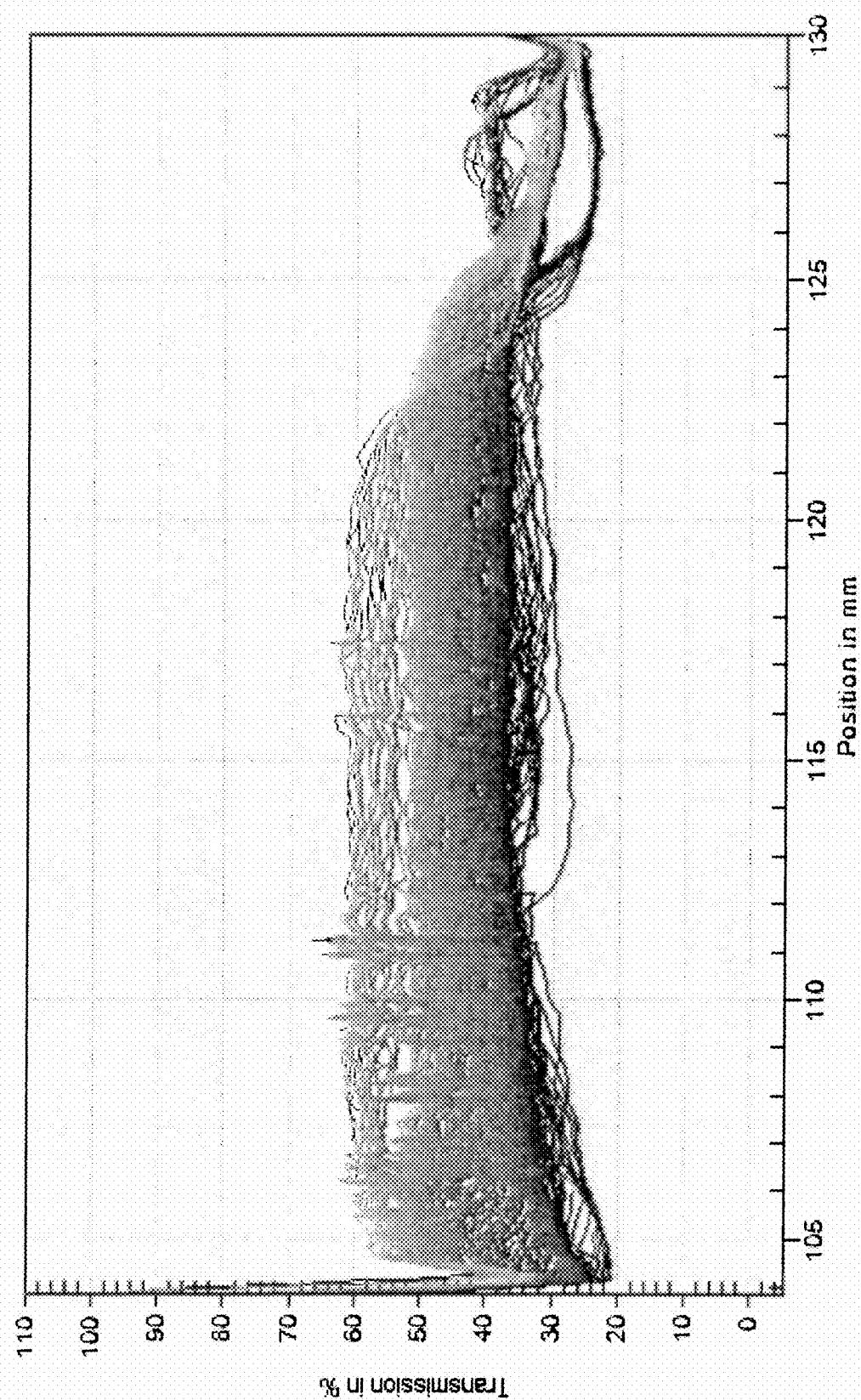
FIG. 6 shows Lumisizer™ light transmission measurement through a 1:1 mixture of Formulation F5 and HBSS.
Figure 7:
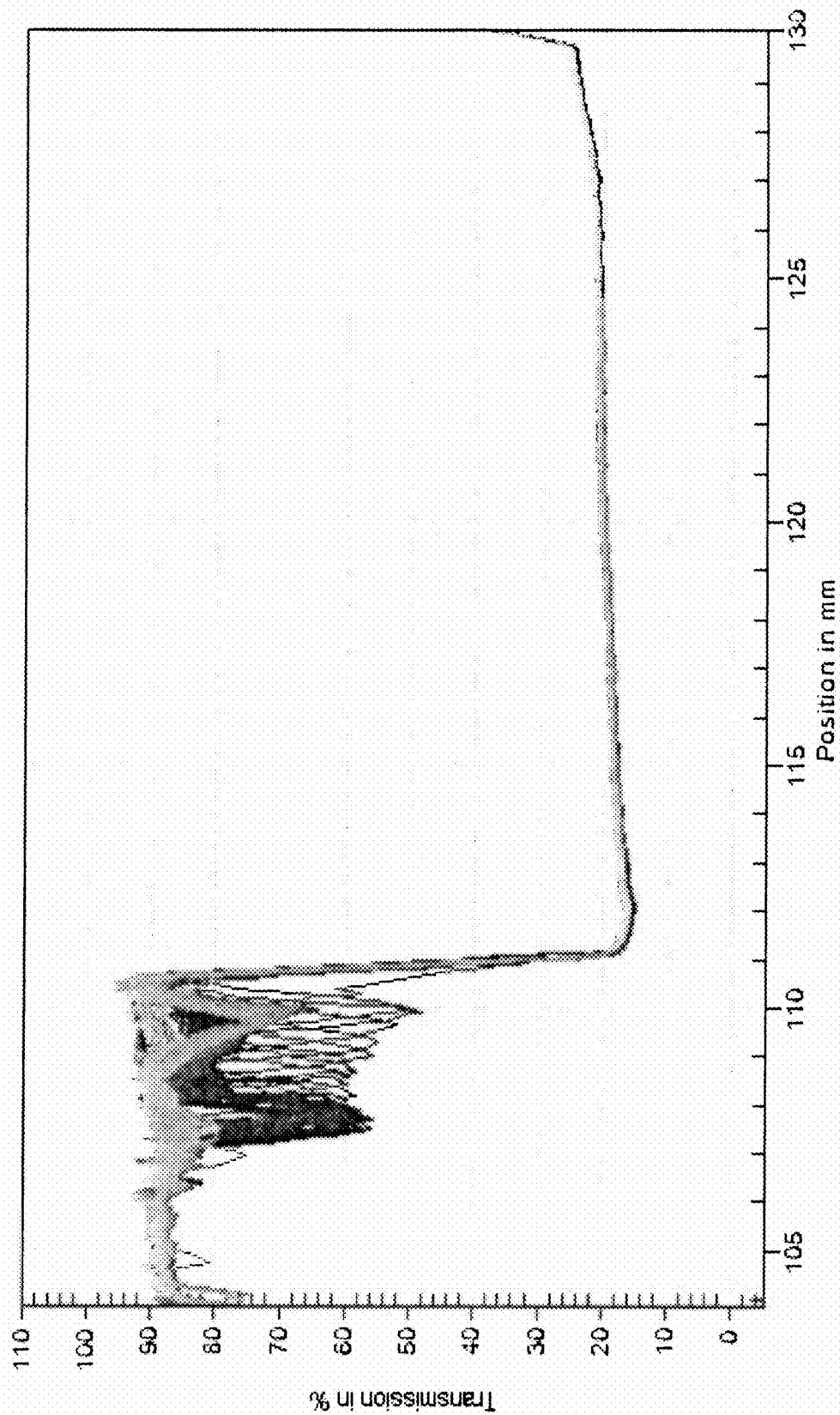
FIG. 7 shows Lumisizer™ light transmission measurement through neat Formulation F7.
Figure 8:
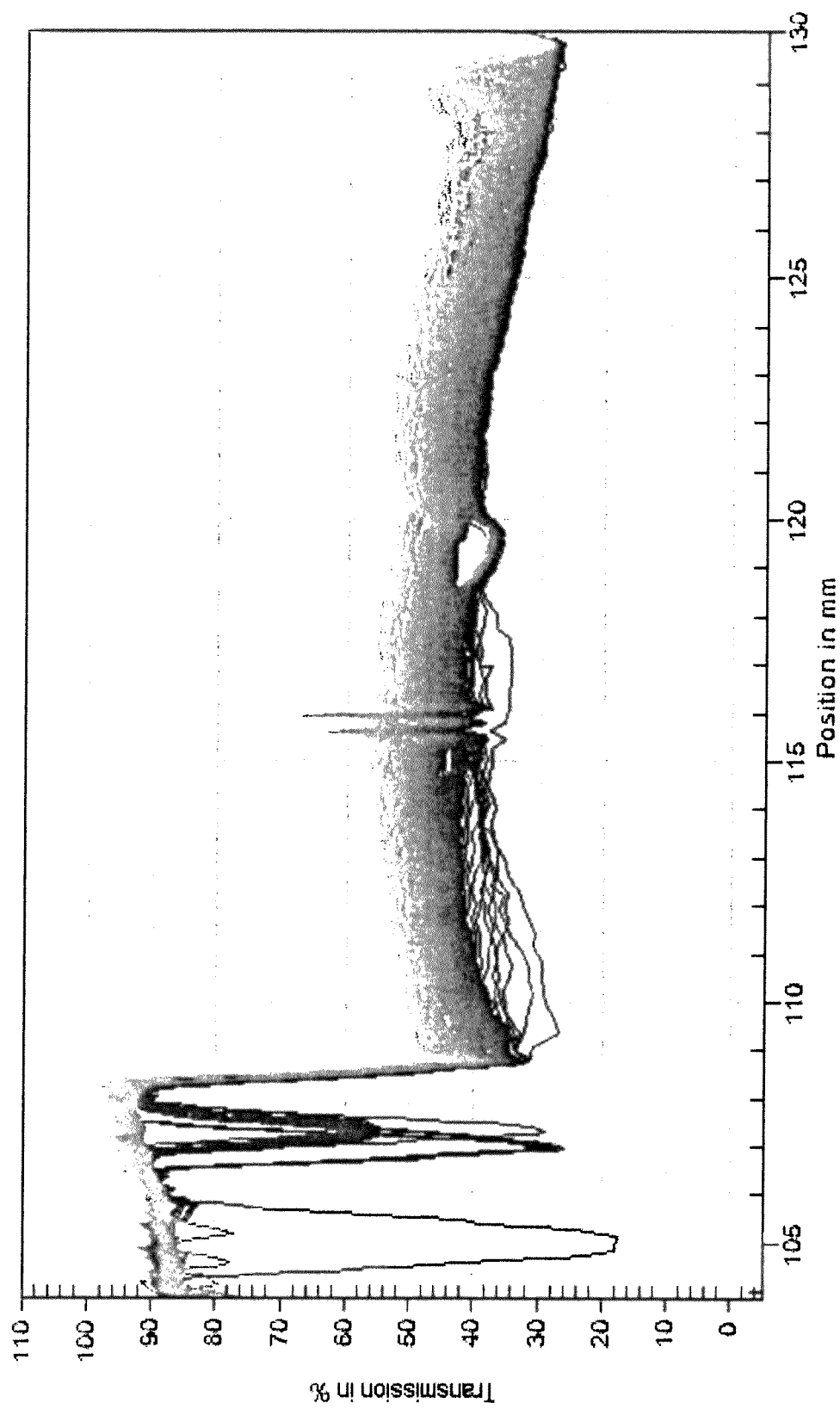
FIG. 8 shows Lumisizer™ light transmission measurement through a 1:1 mixture of Formulation F7 and HBSS.
Figure 9:
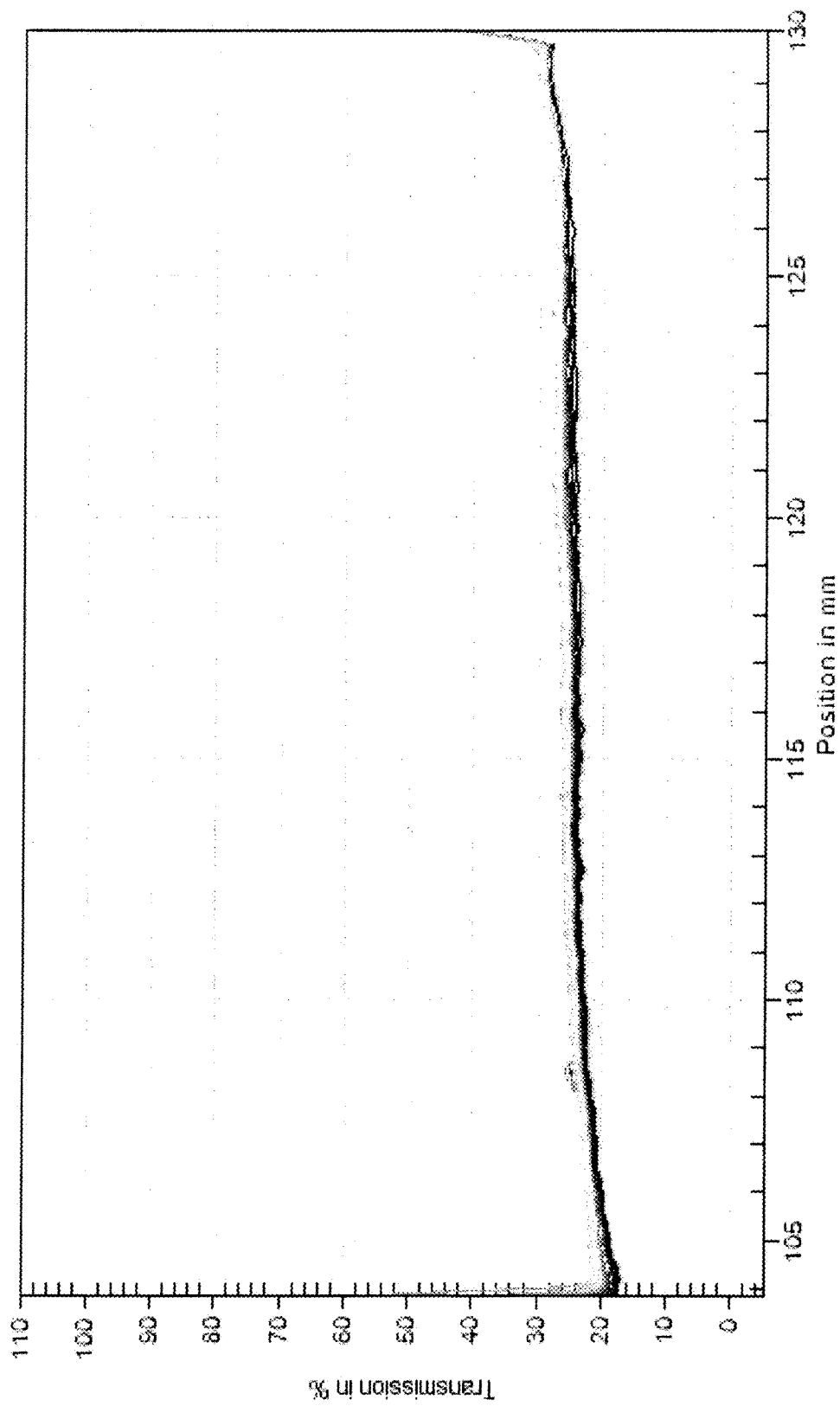
FIG. 9 shows Lumisizer™ light transmission measurement through neat Formulation F9.
Figure 10:
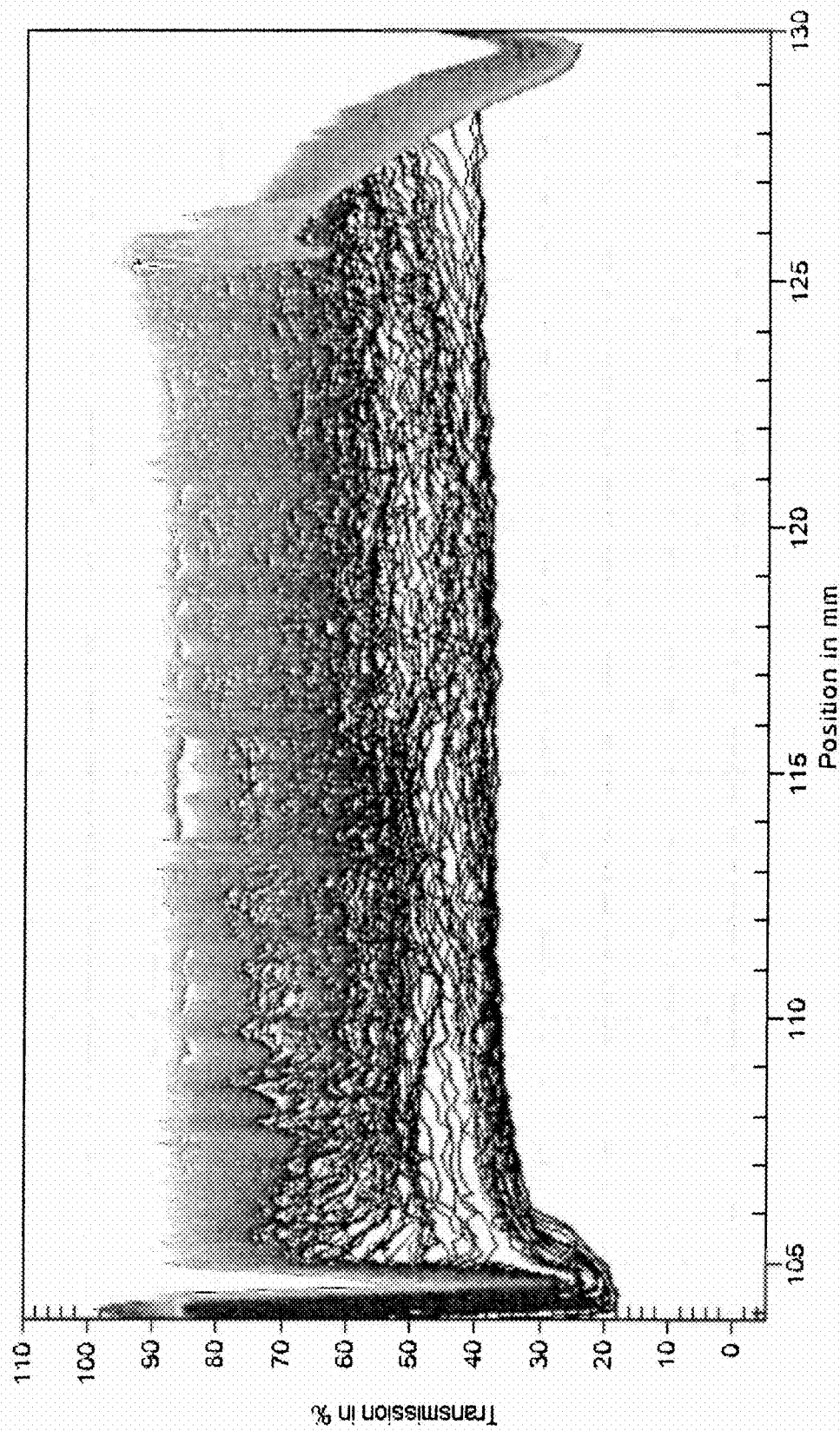
FIG. 10 shows Lumisizer™ light transmission measurement through a 1:1 mixture of Formulation F9 and HBSS.
Figure 11:
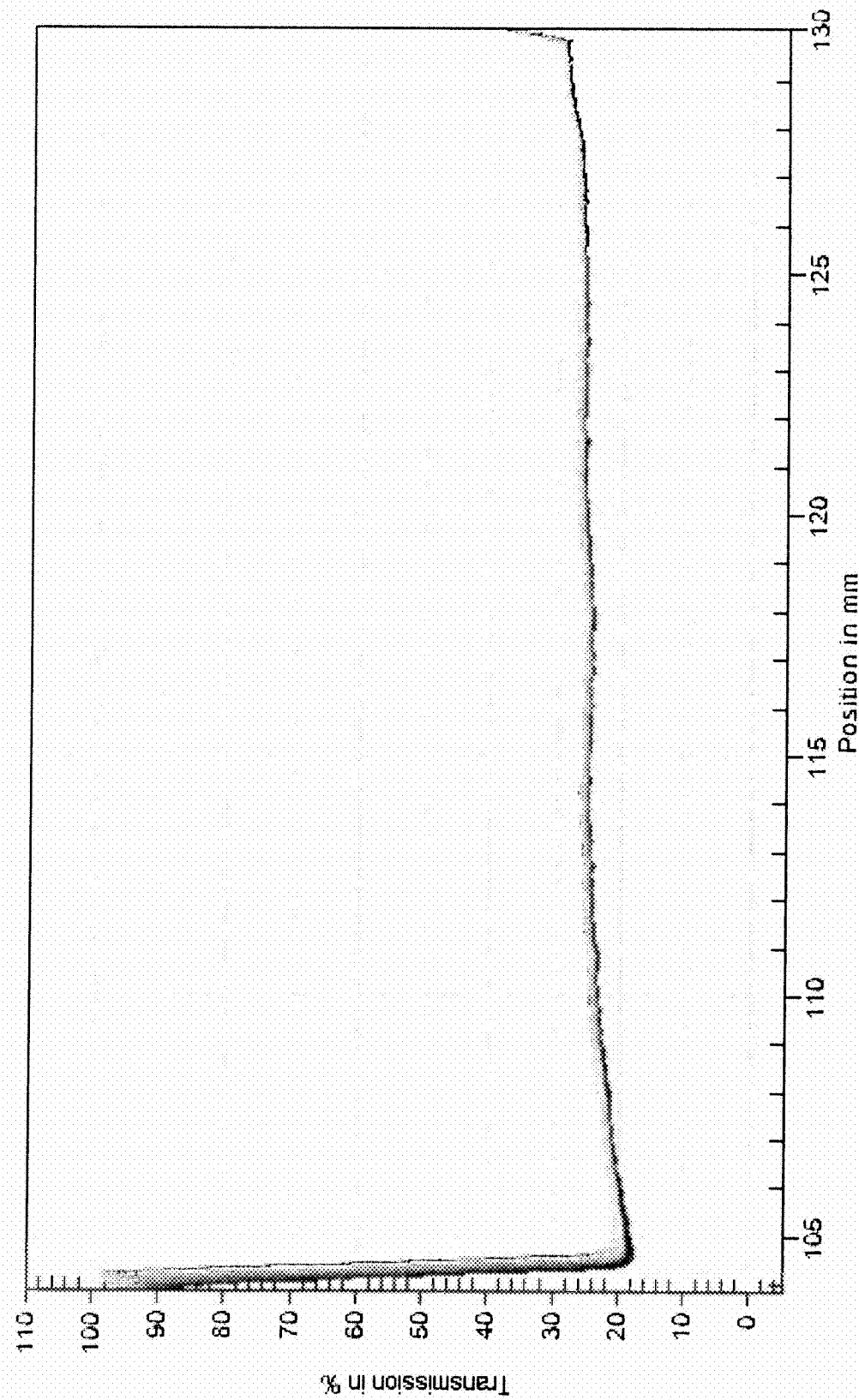
FIG. 11 shows Lumisizer™ light transmission measurement through neat Formulation F4.
Figure 12:
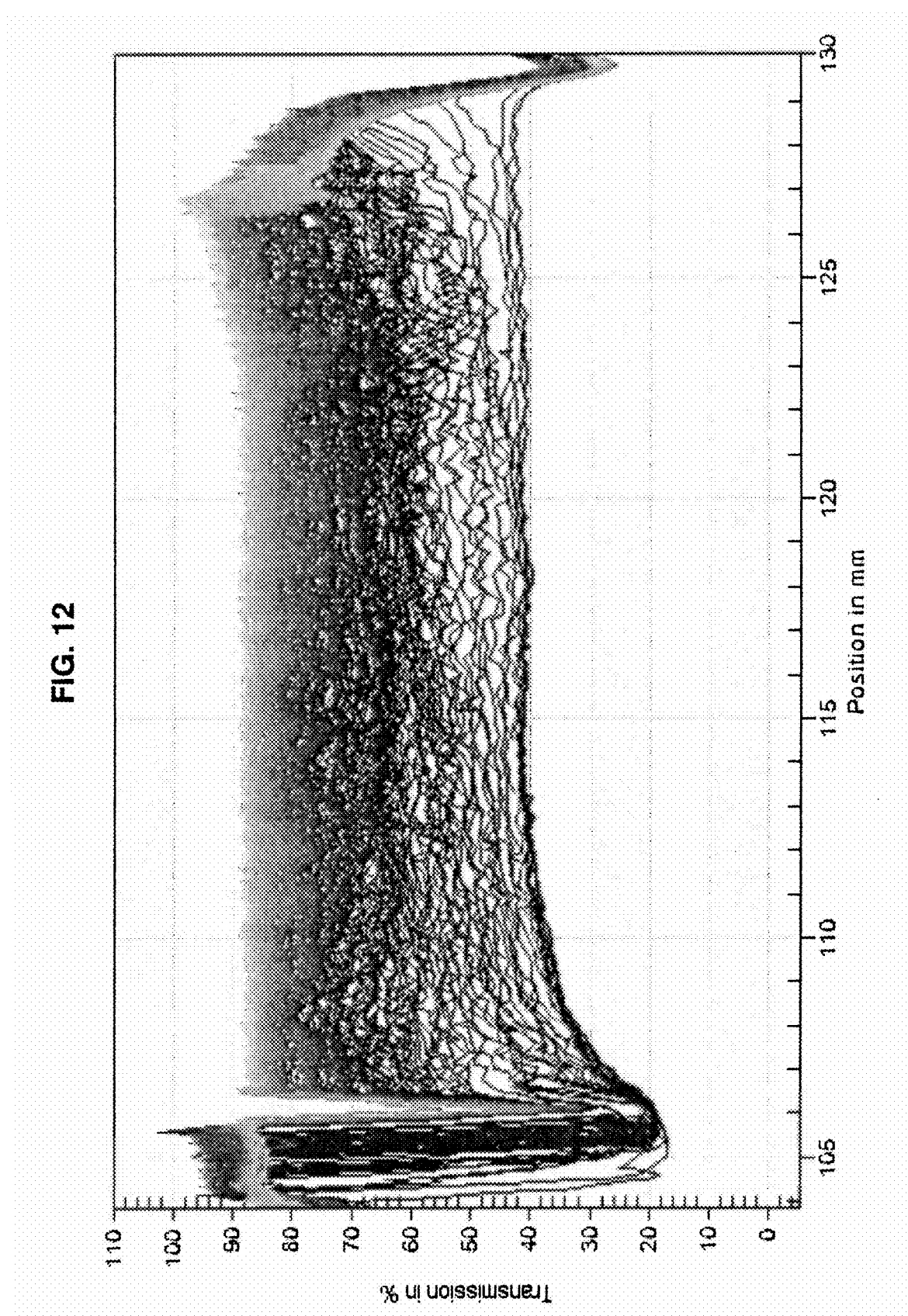
FIG. 12 shows Lumisizer™ light transmission measurement through a 1:1 mixture of Formulation F4 and HBSS.
Figure 13:
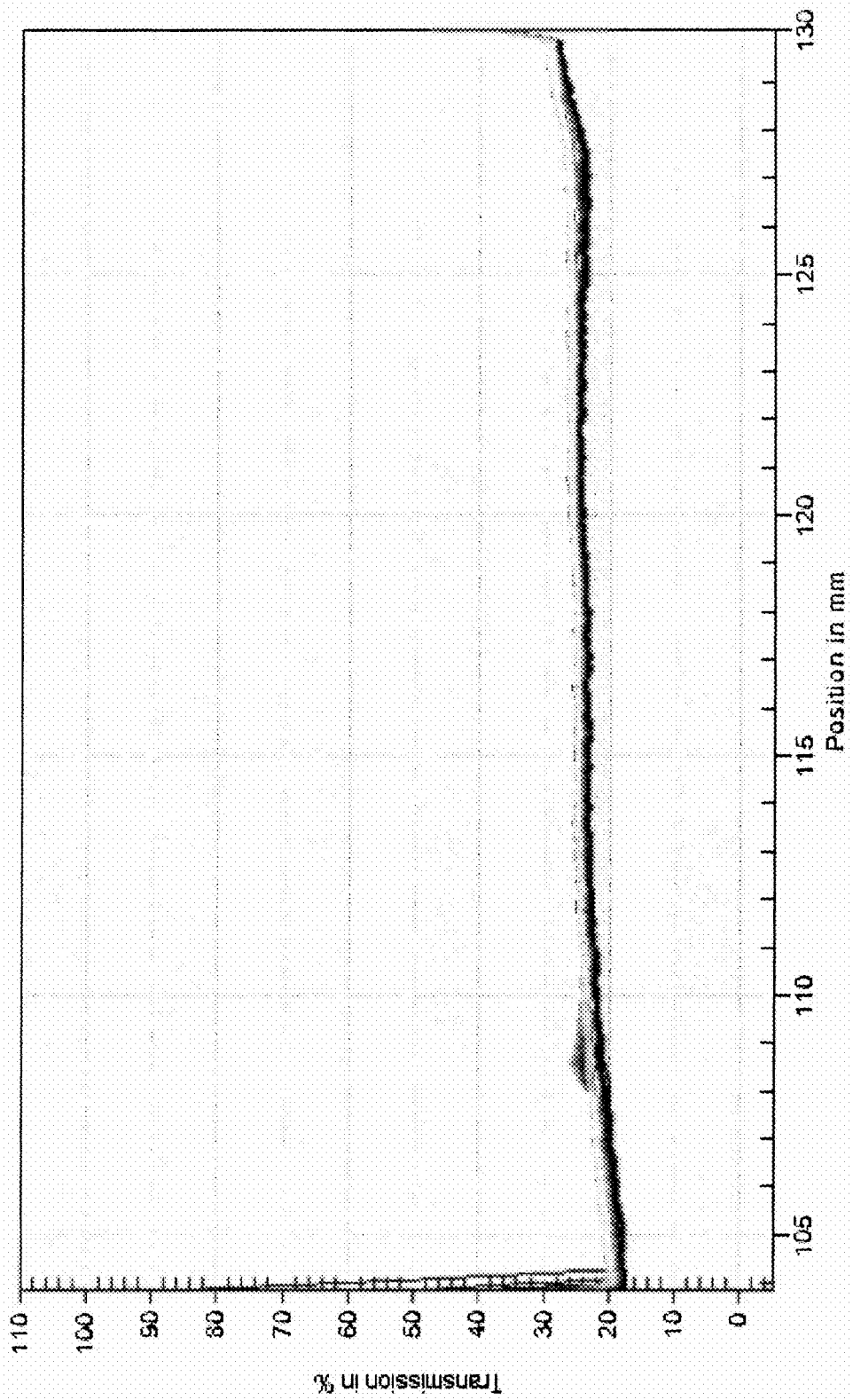
FIG. 13 shows Lumisizer™ light transmission measurement through neat Formulation F6.
Figure 14:
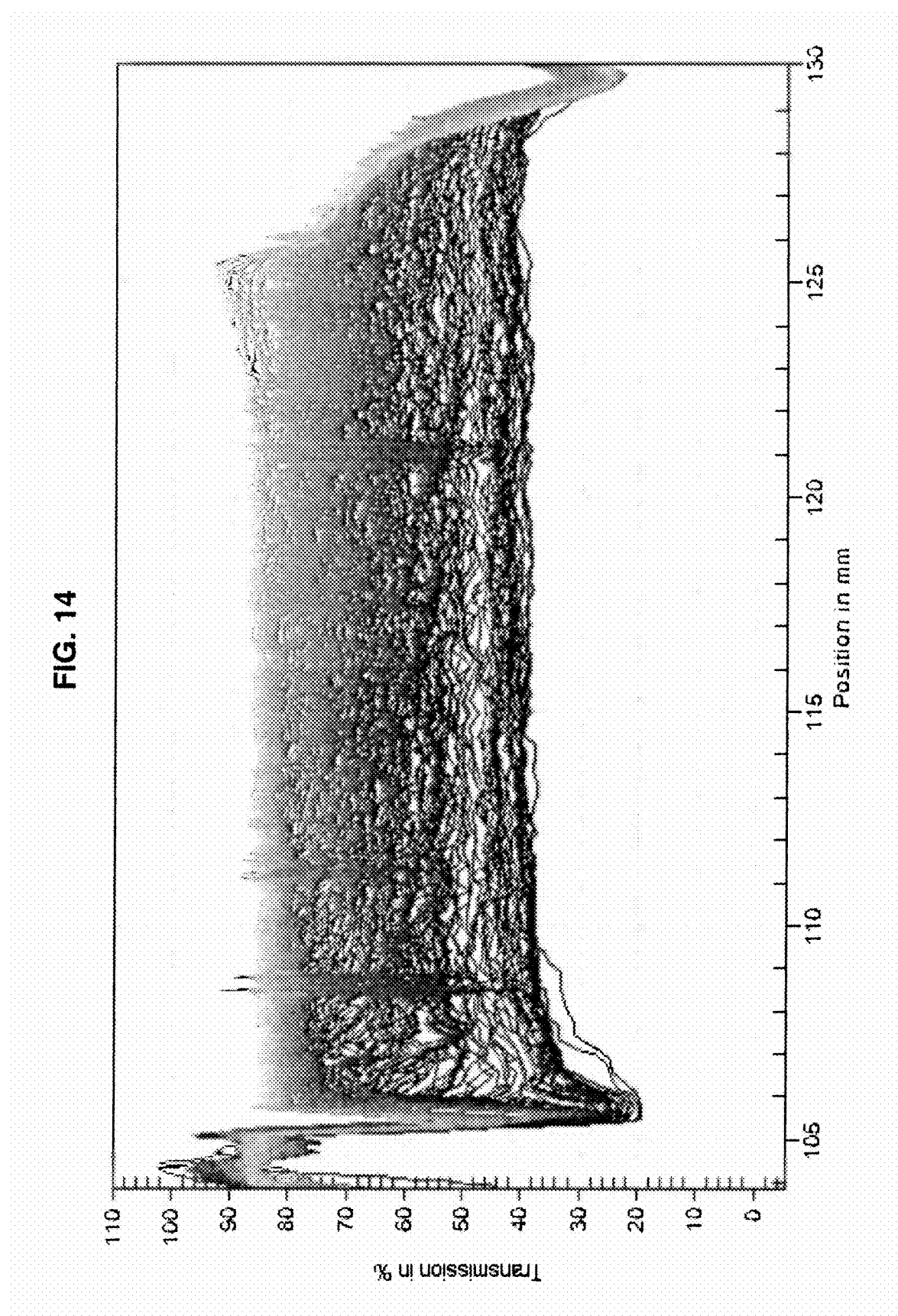
FIG. 14 shows Lumisizer™ light transmission measurement through a 1:1 mixture of Formulation F6 and HBSS.
Figure 15:
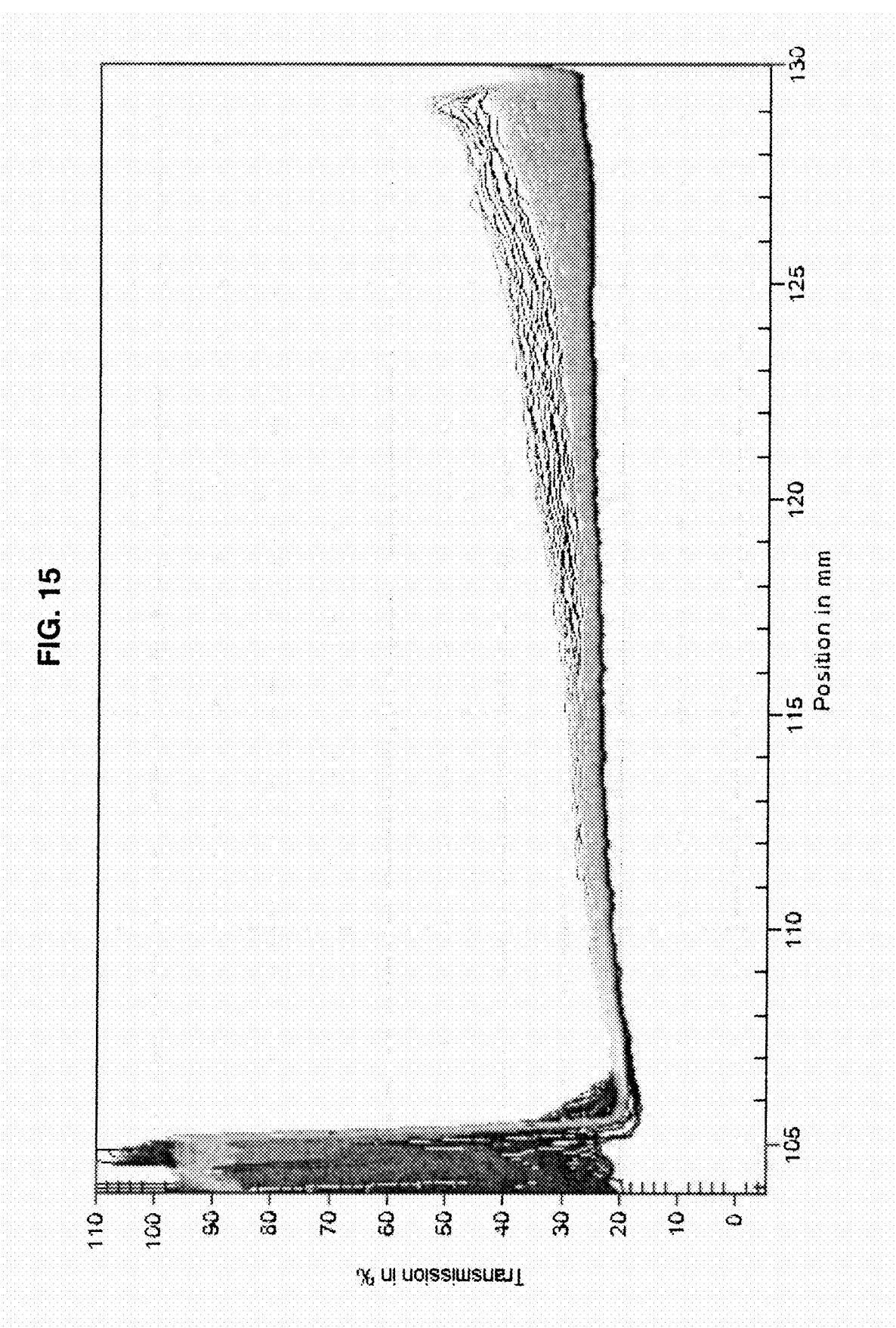
FIG. 15 shows Lumisizer™ light transmission measurement through neat Formulation F8.
Figure 16:
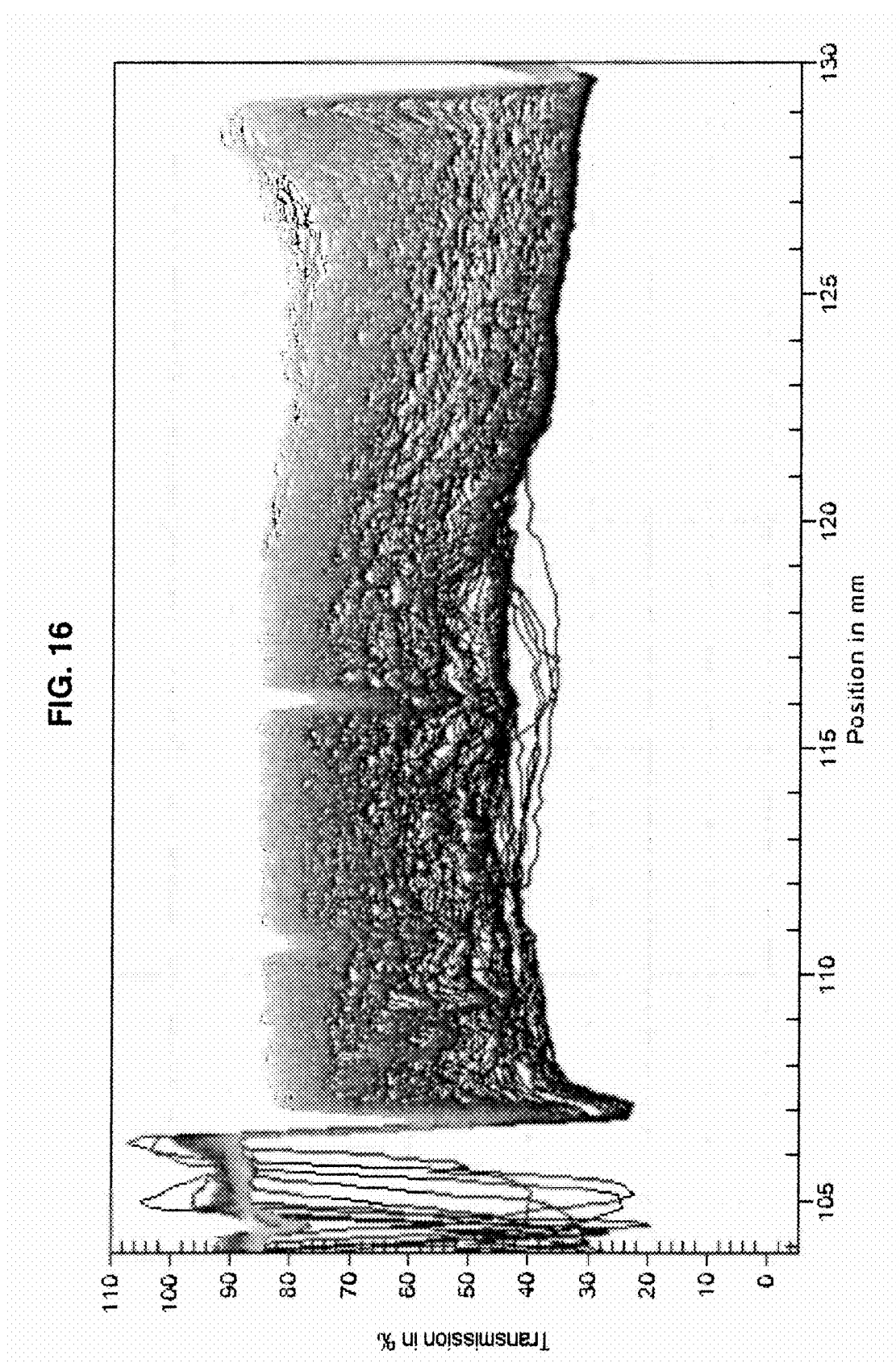
FIG. 16 shows Lumisizer™ light transmission measurement through a 1:1 mixture of Formulation F8 and HBSS.
Figure 17:
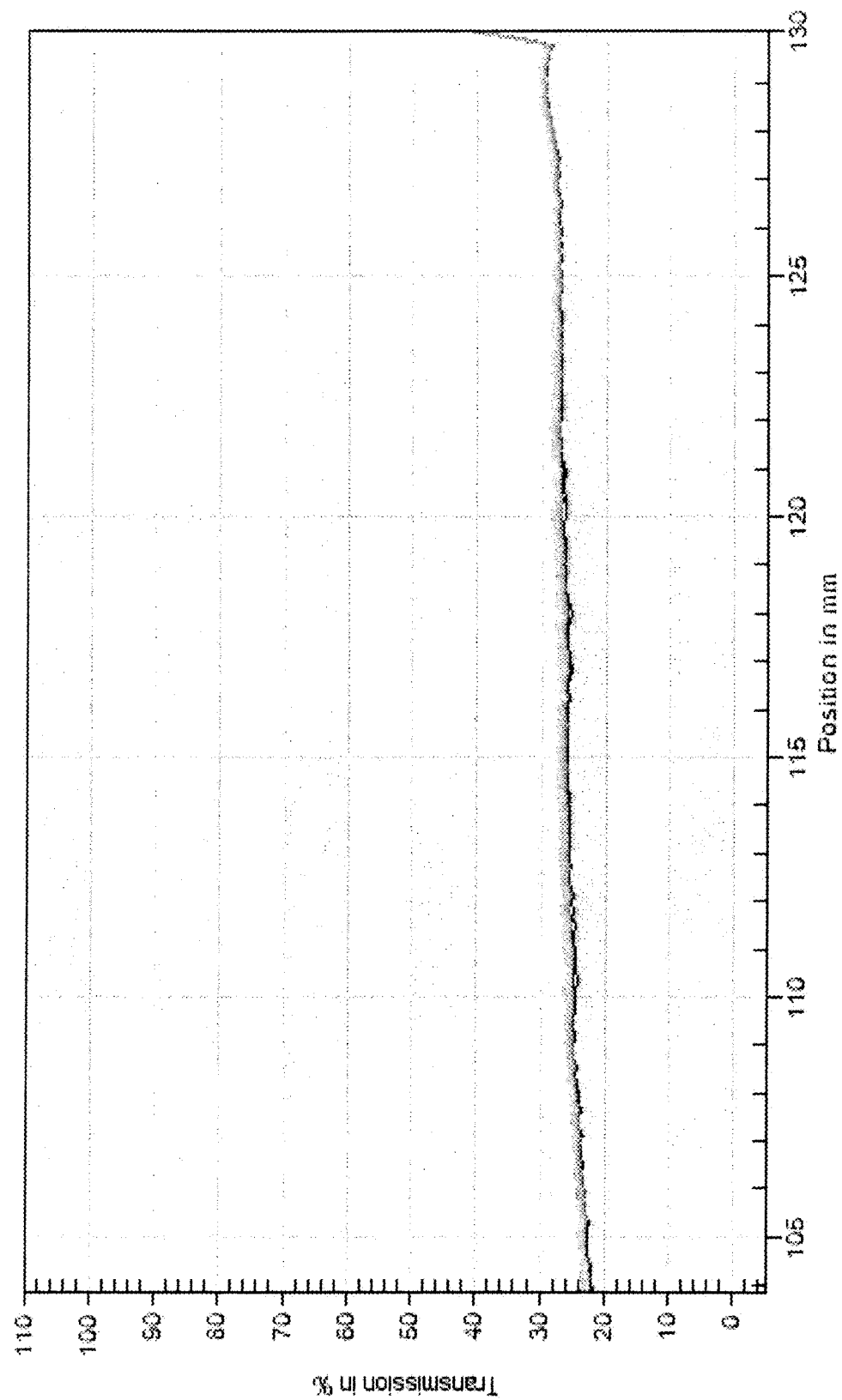
FIG. 17 shows Lumisizer™ light transmission measurement through neat Formulation F9.
Figure 18:
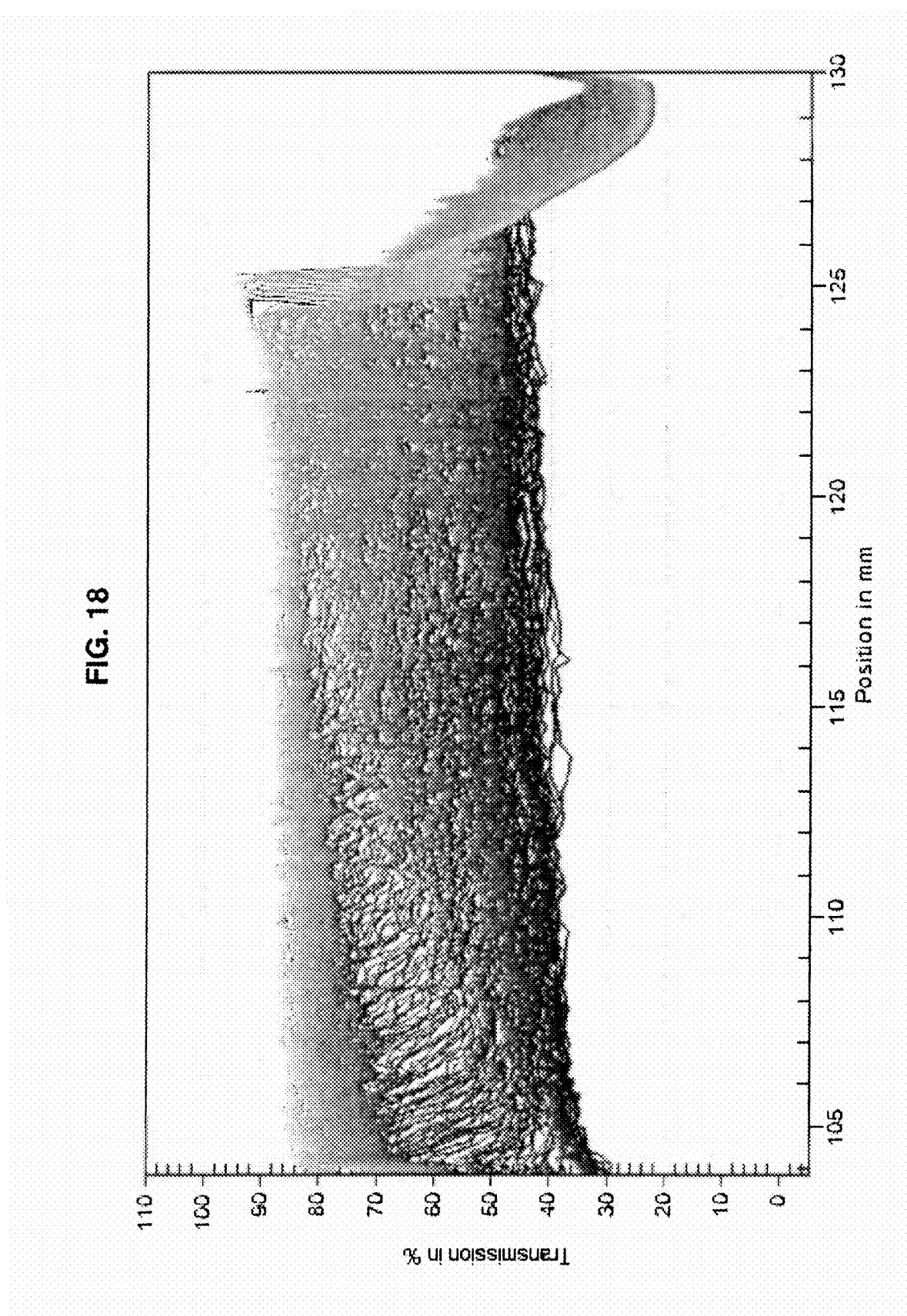
FIG. 18 shows Lumisizer™ light transmission measurement through a 1:1 mixture of Formulation F9 and HBSS.
Figure 19:
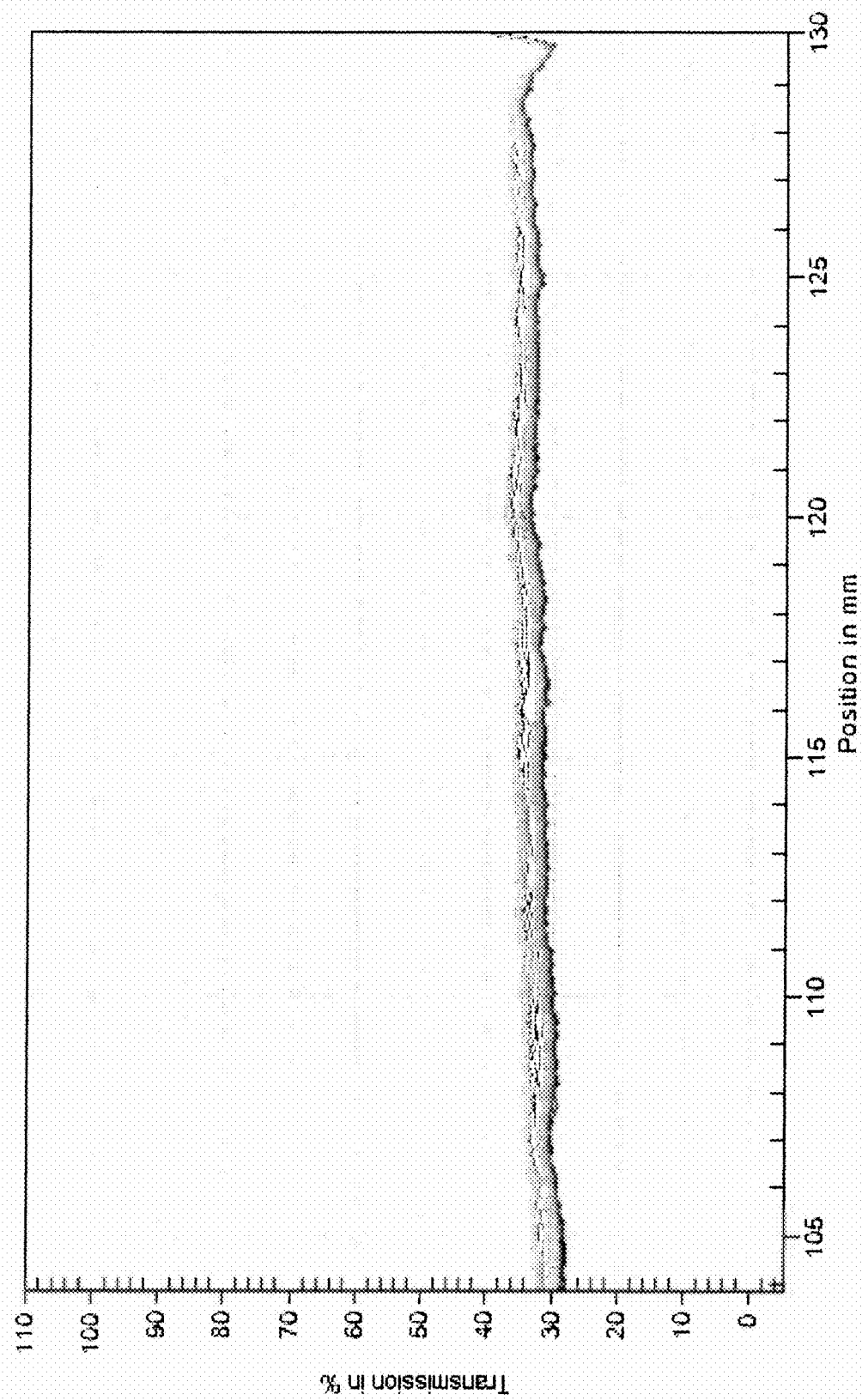
FIG. 19 shows Lumisizer™ light transmission measurement through neat Formulation F11.
Figure 20:
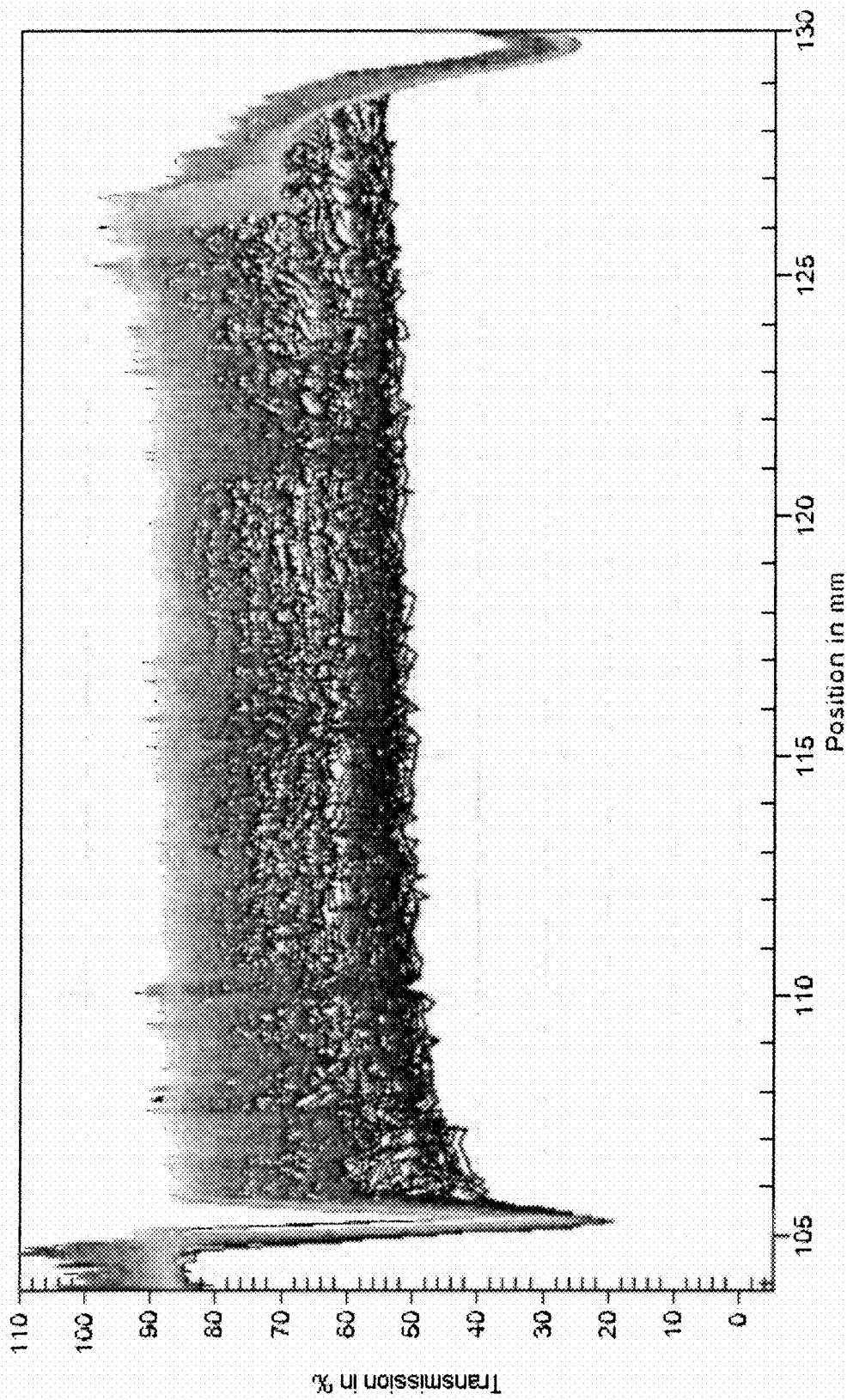
FIG. 20 shows Lumisizer™ light transmission measurement through a 1:1 mixture of Formulation F11 and HBSS.
Figure 21:
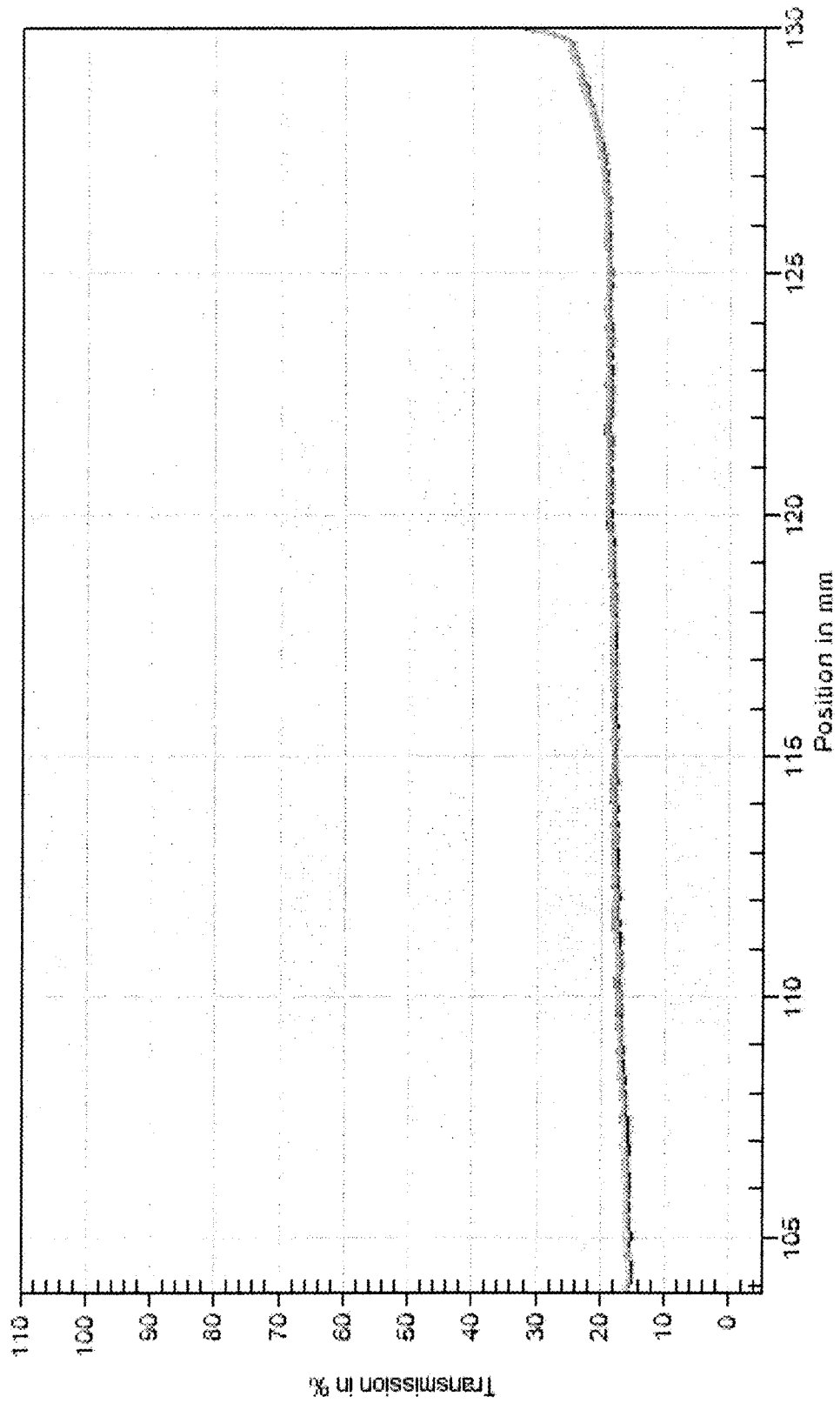
FIG. 21 shows Lumisizer™ light transmission measurement through neat Formulation F13.
Figure 22:
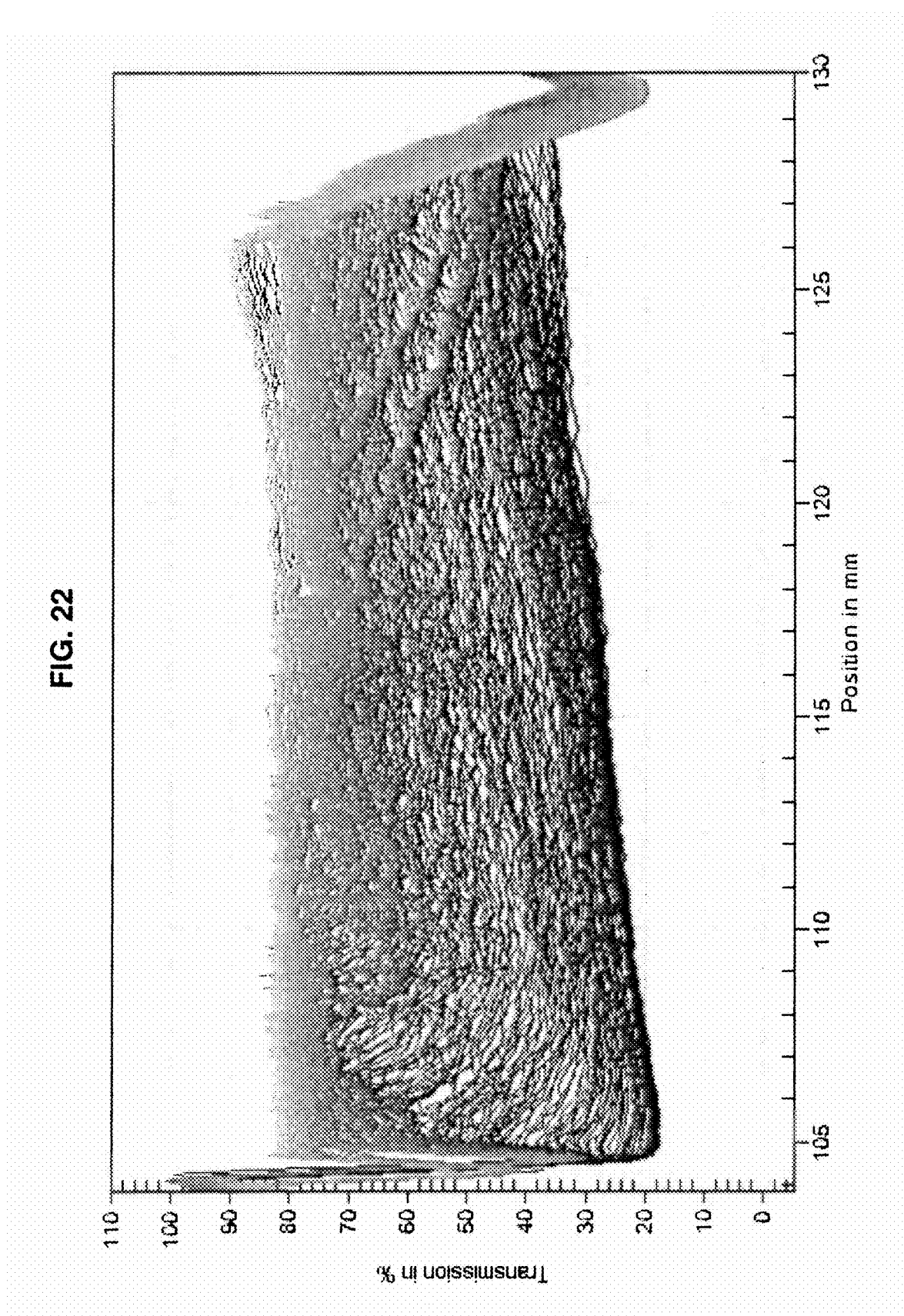
FIG. 22 shows Lumisizer™ light transmission measurement through a 1:1 mixture of Formulation F13 and HBSS.
Figure 23:
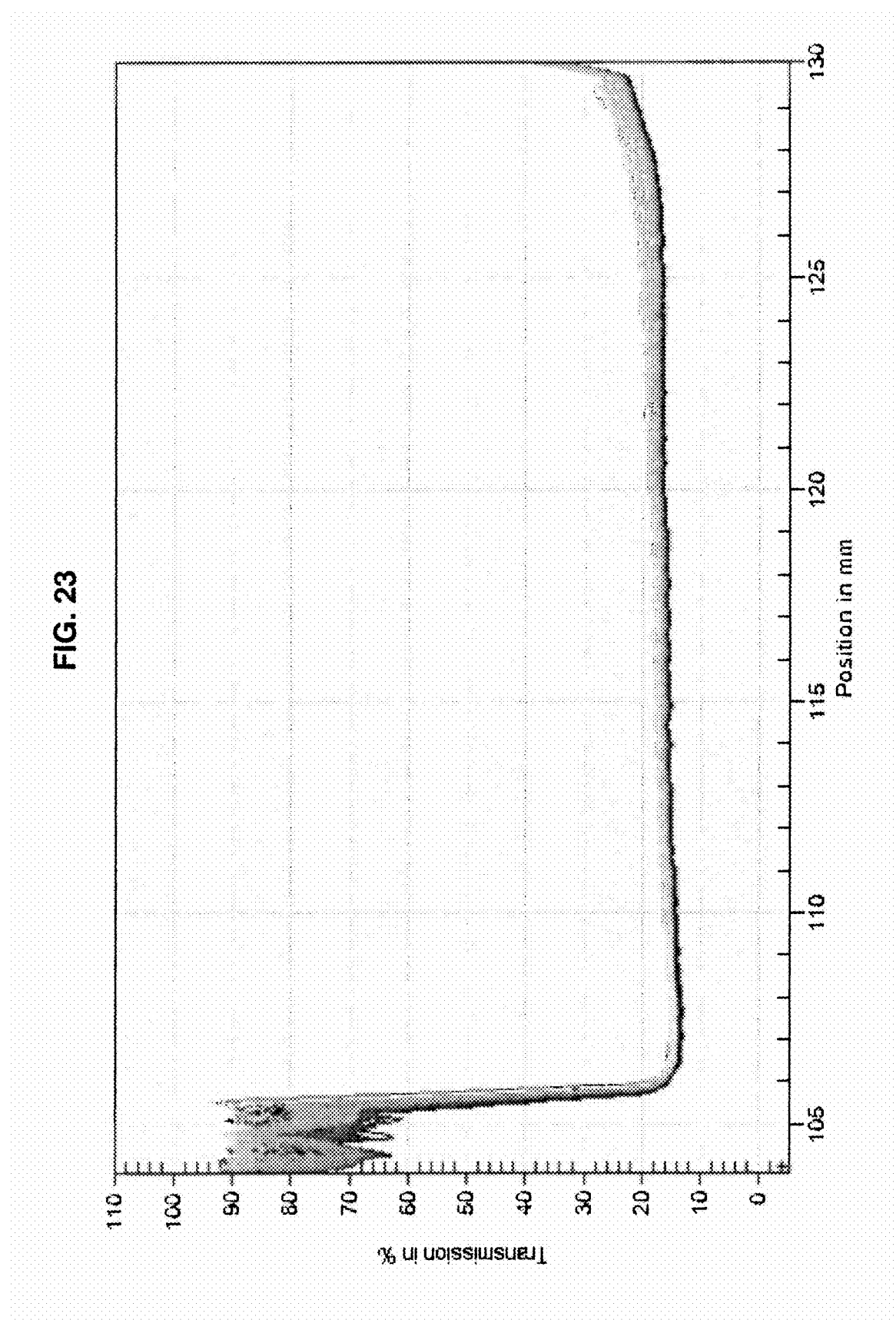
FIG. 23 shows Lumisizer™ light transmission measurement through neat Formulation F15.
Figure 24:
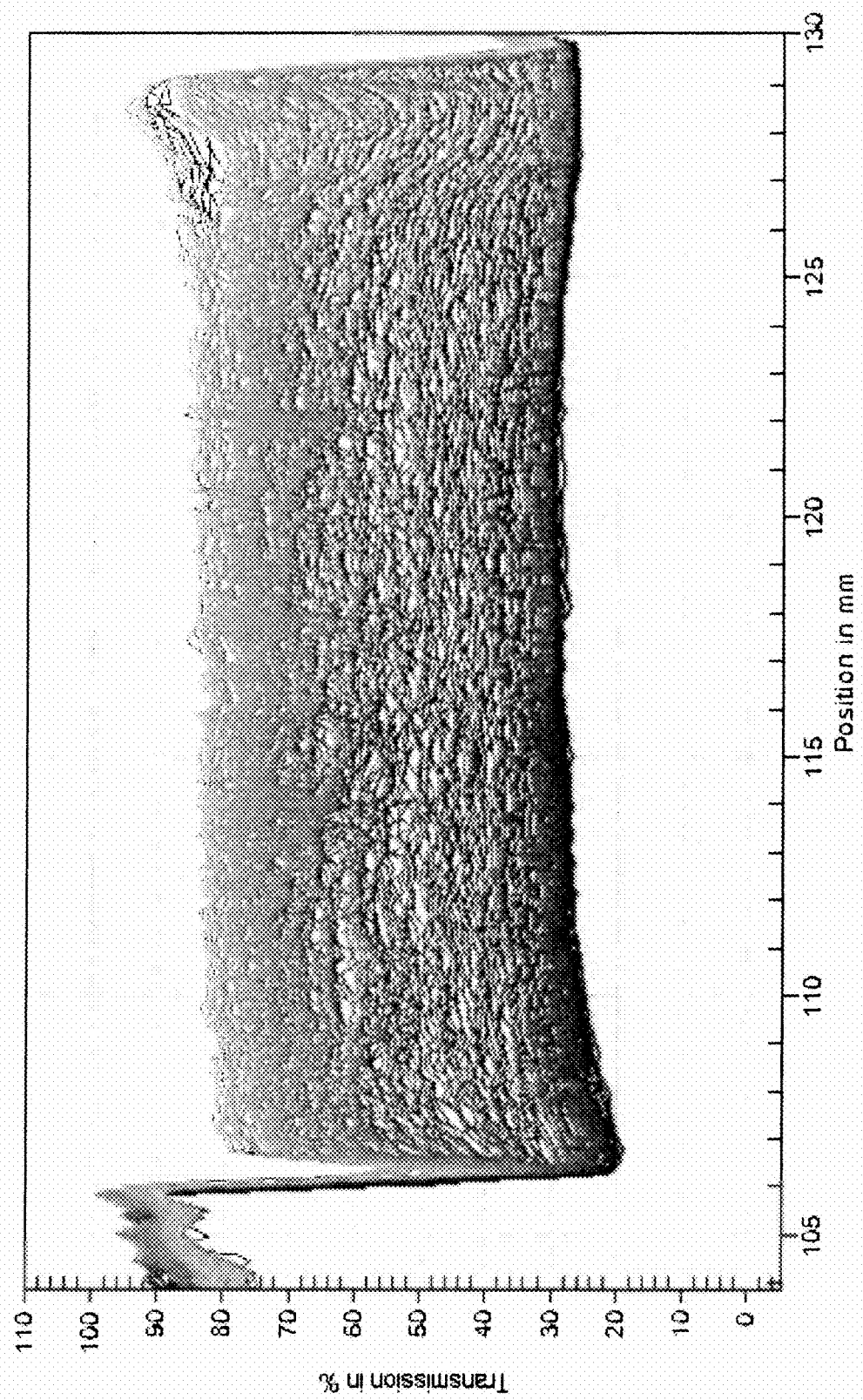
FIG. 24 shows Lumisizer™ light transmission measurement through a 1:1 mixture of Formulation F15 and HBSS.
Figure 25:
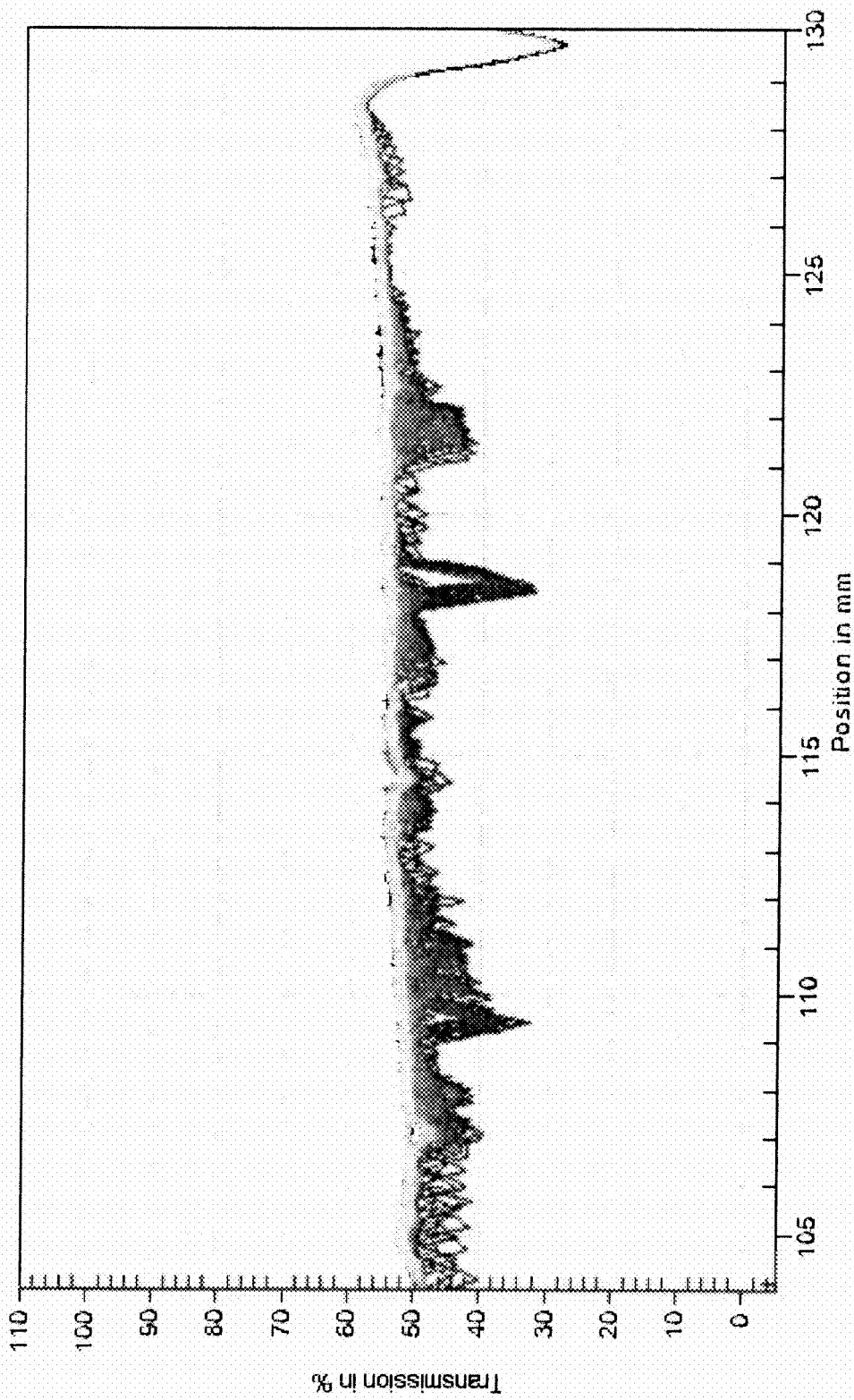
FIG. 25 shows Lumisizer™ light transmission measurement through neat Formulation F10.
Figure 26:
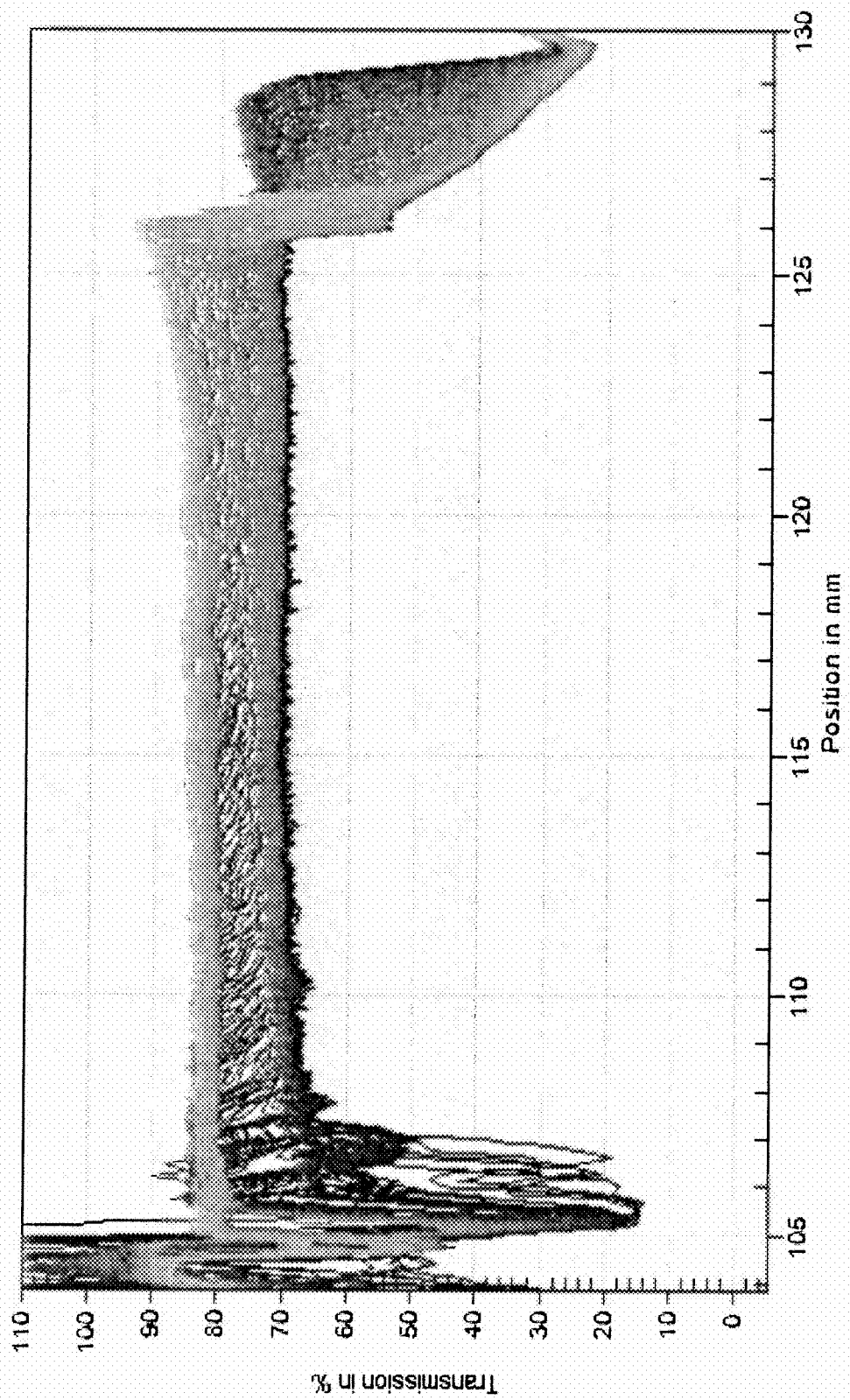
FIG. 26 shows Lumisizer™ light transmission measurement through a 1:1 mixture of Formulation F10 and HBSS.
Figure 27:
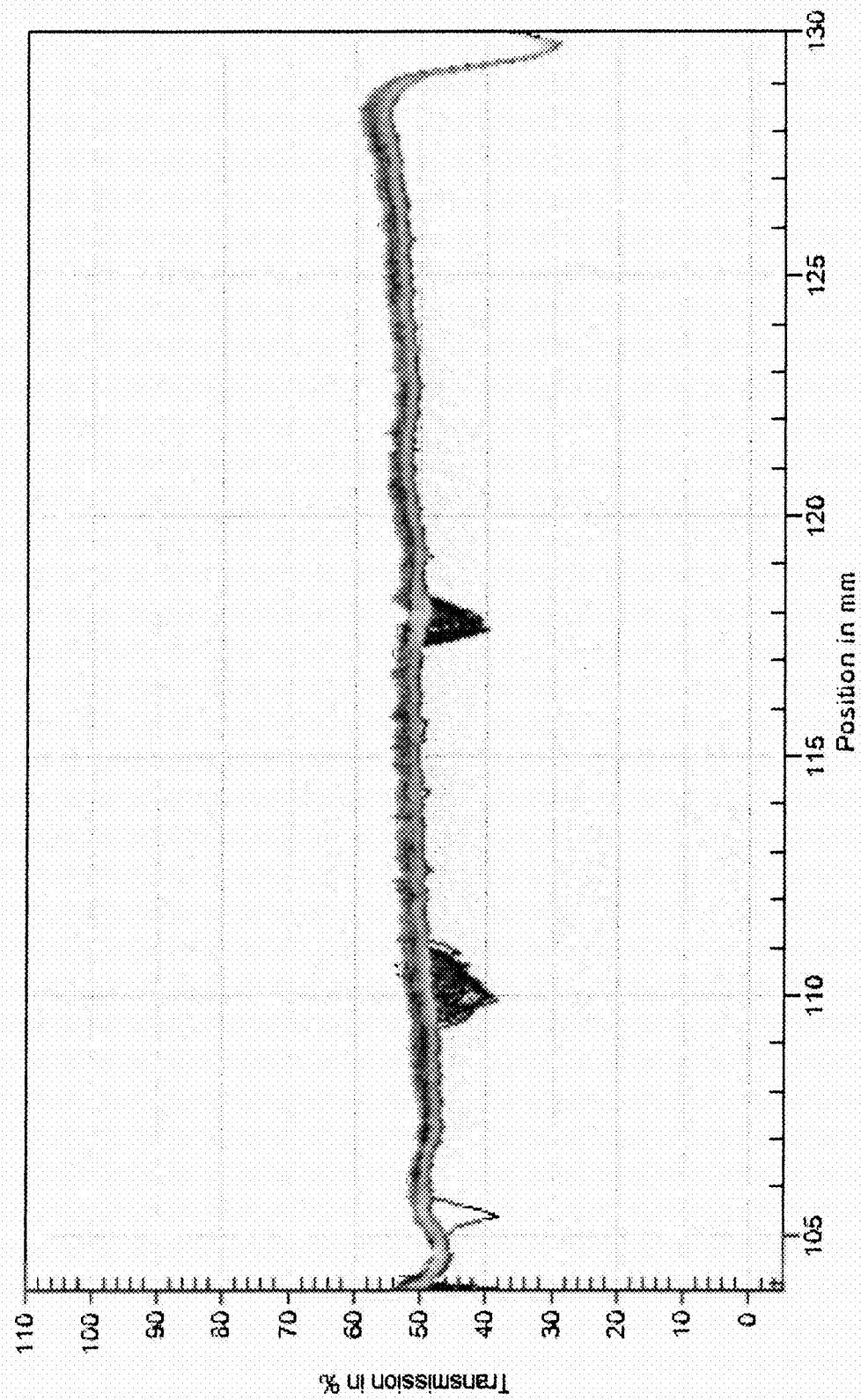
FIG. 27 shows Lumisizer™ light transmission measurement through neat Formulation F12.
Figure 28:
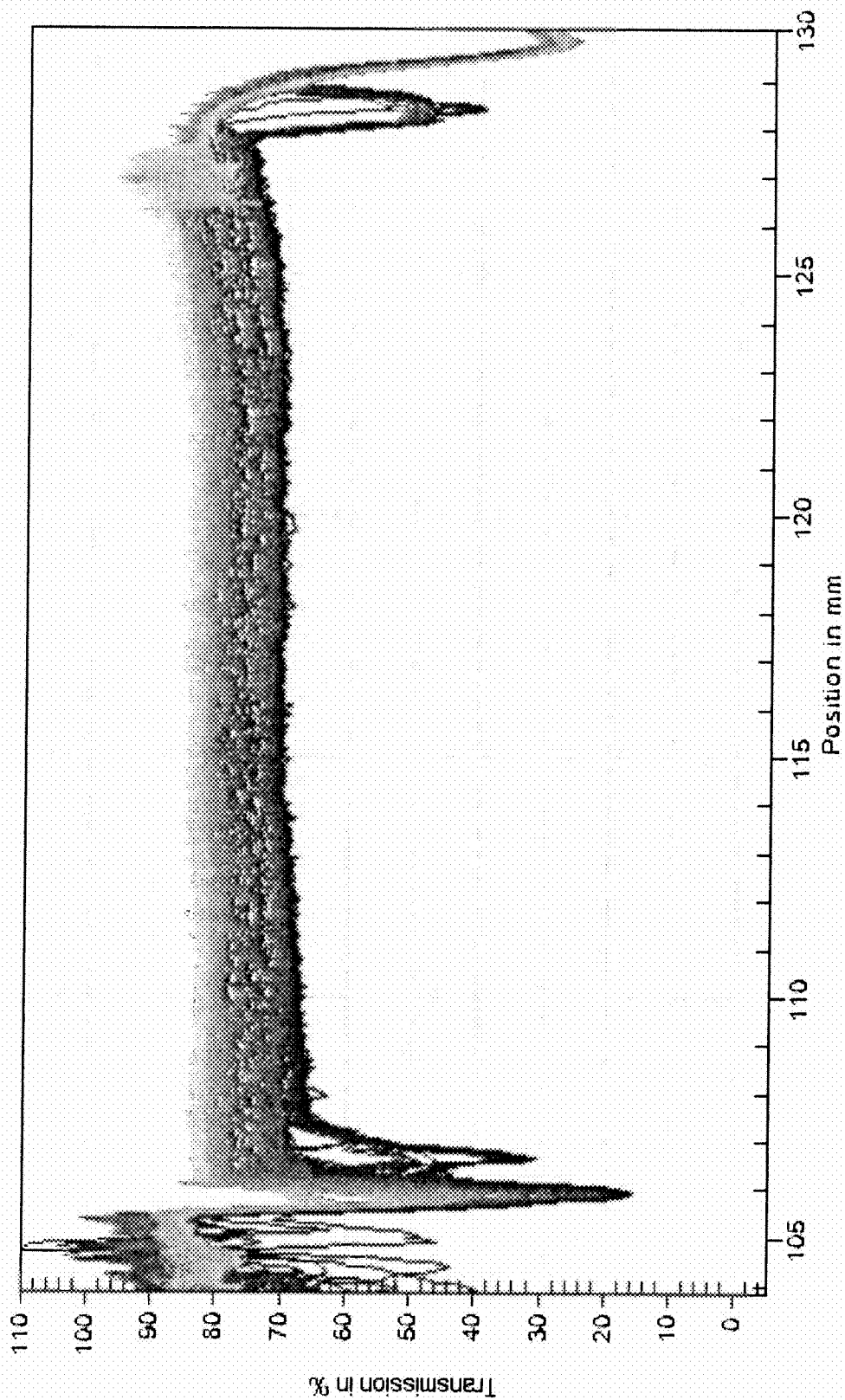
FIG. 28 shows Lumisizer™ light transmission measurement through a 1:1 mixture of Formulation F12 and HBSS.
Figure 29:
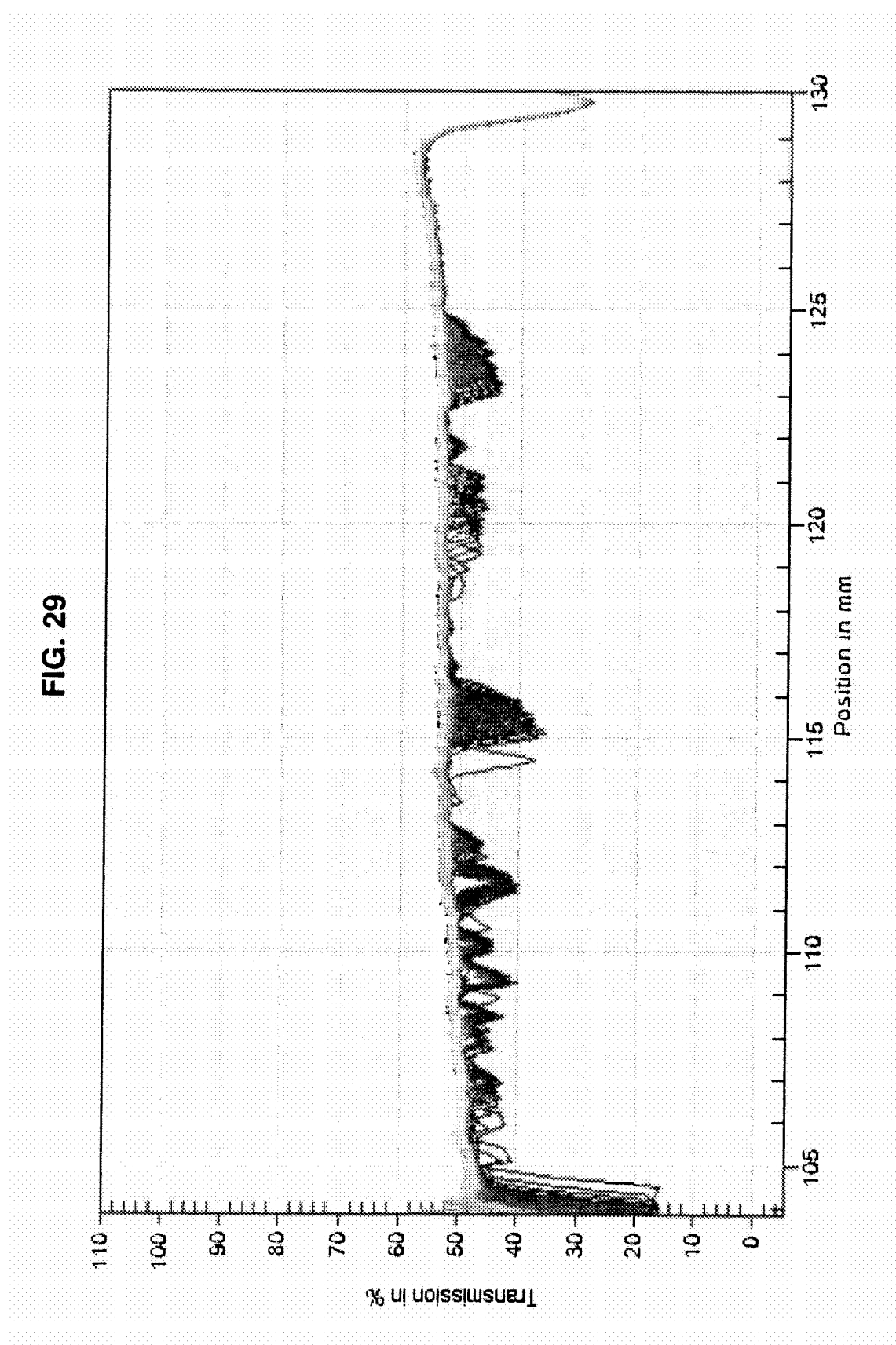
FIG. 29 shows Lumisizer™ light transmission measurement through neat Formulation F14.
Figure 30:
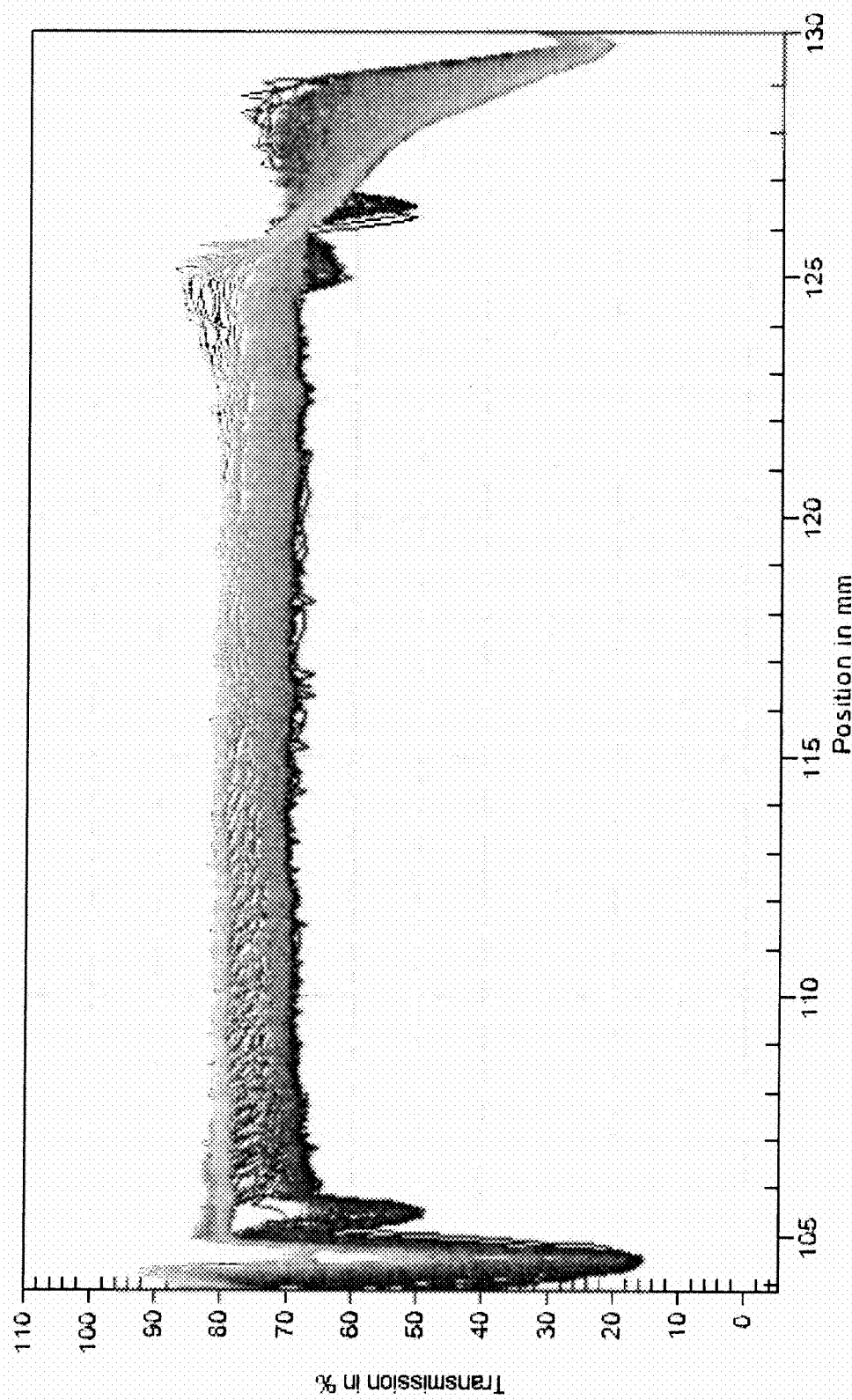
FIG. 30 shows Lumisizer™ light transmission measurement through a 1:1 mixture of Formulation F14 and HBSS.
Figure 31:
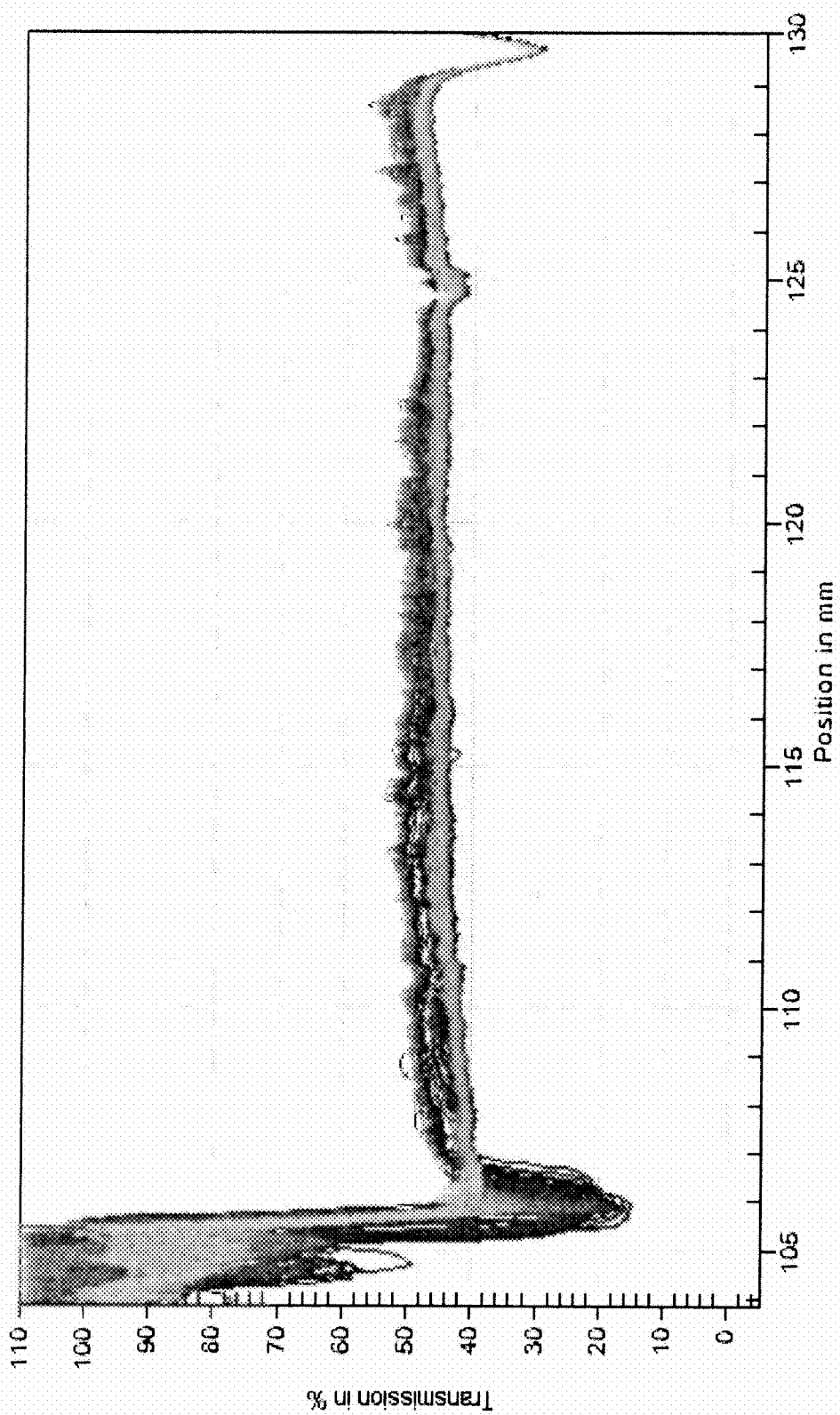
FIG. 31 shows Lumisizer™ light transmission measurement through neat Formulation F16.
Figure 32:
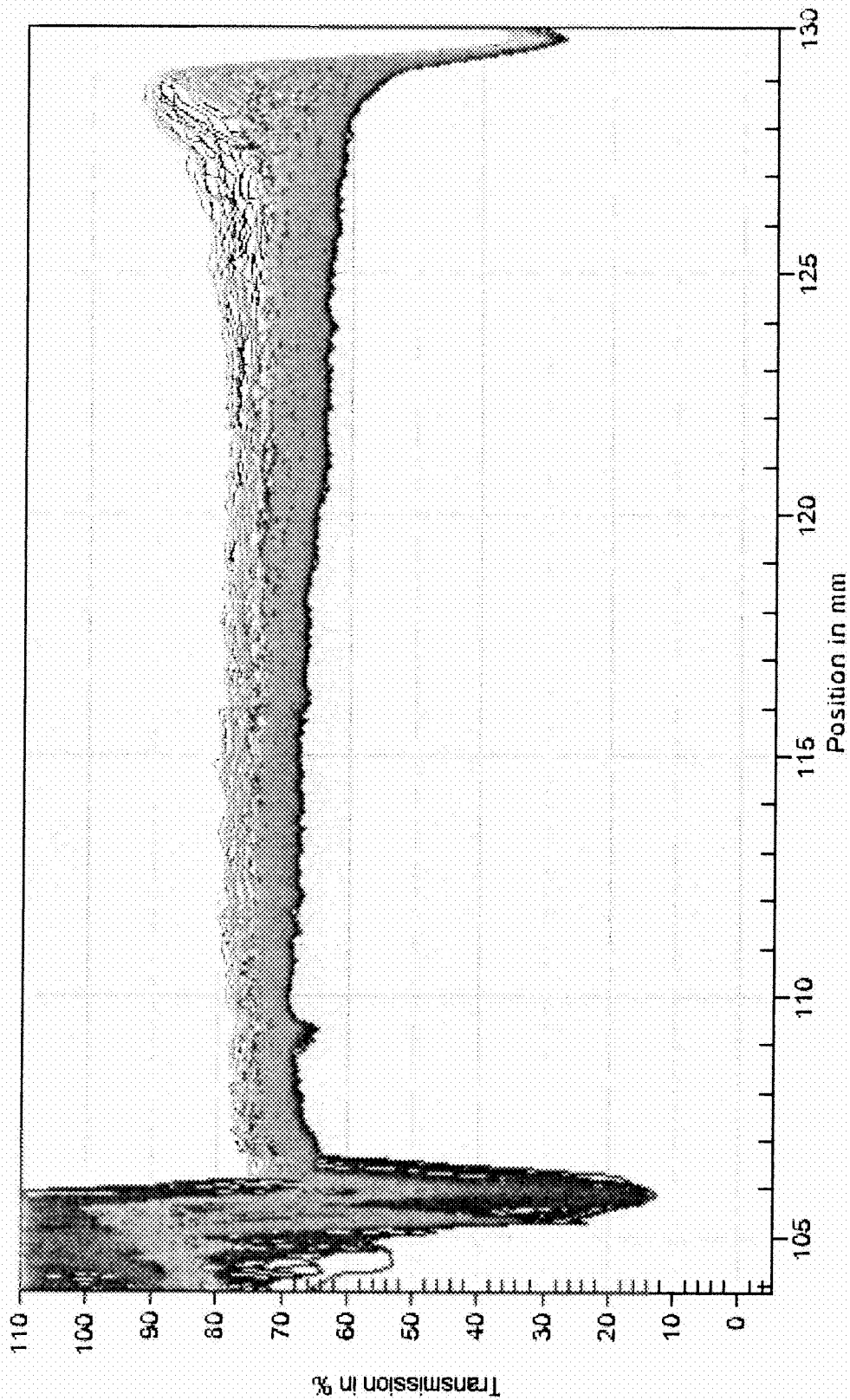
FIG. 32 shows Lumisizer™ light transmission measurement through a 1:1 mixture of Formulation F16 and HBSS.
Figure 33:
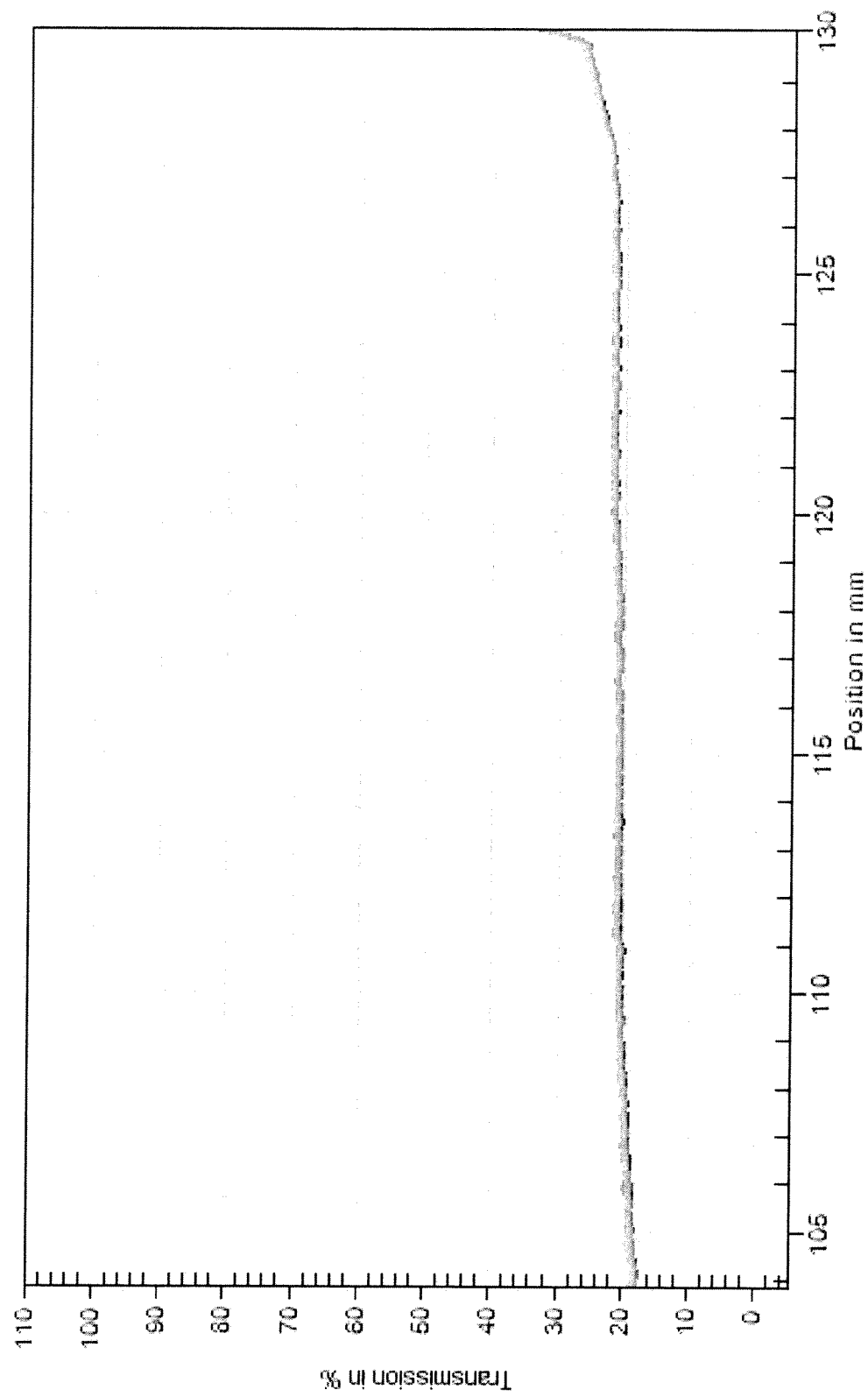
FIG. 33 shows Lumisizer™ light transmission measurement through neat Formulation F17.
Figure 34:
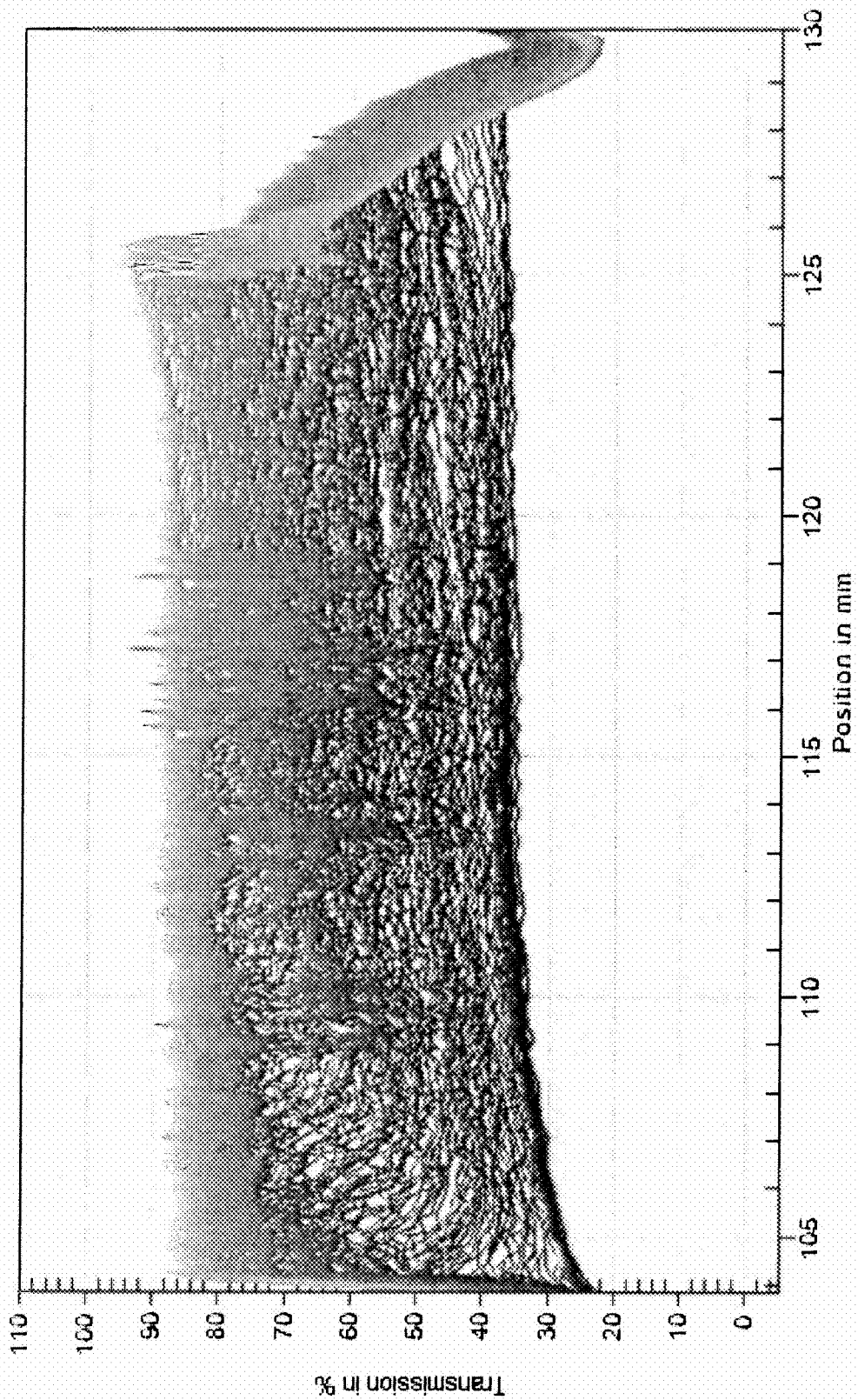
FIG. 34 shows Lumisizer™ light transmission measurement through a 1:1 mixture of Formulation F17 and HBSS.
Figure 35:
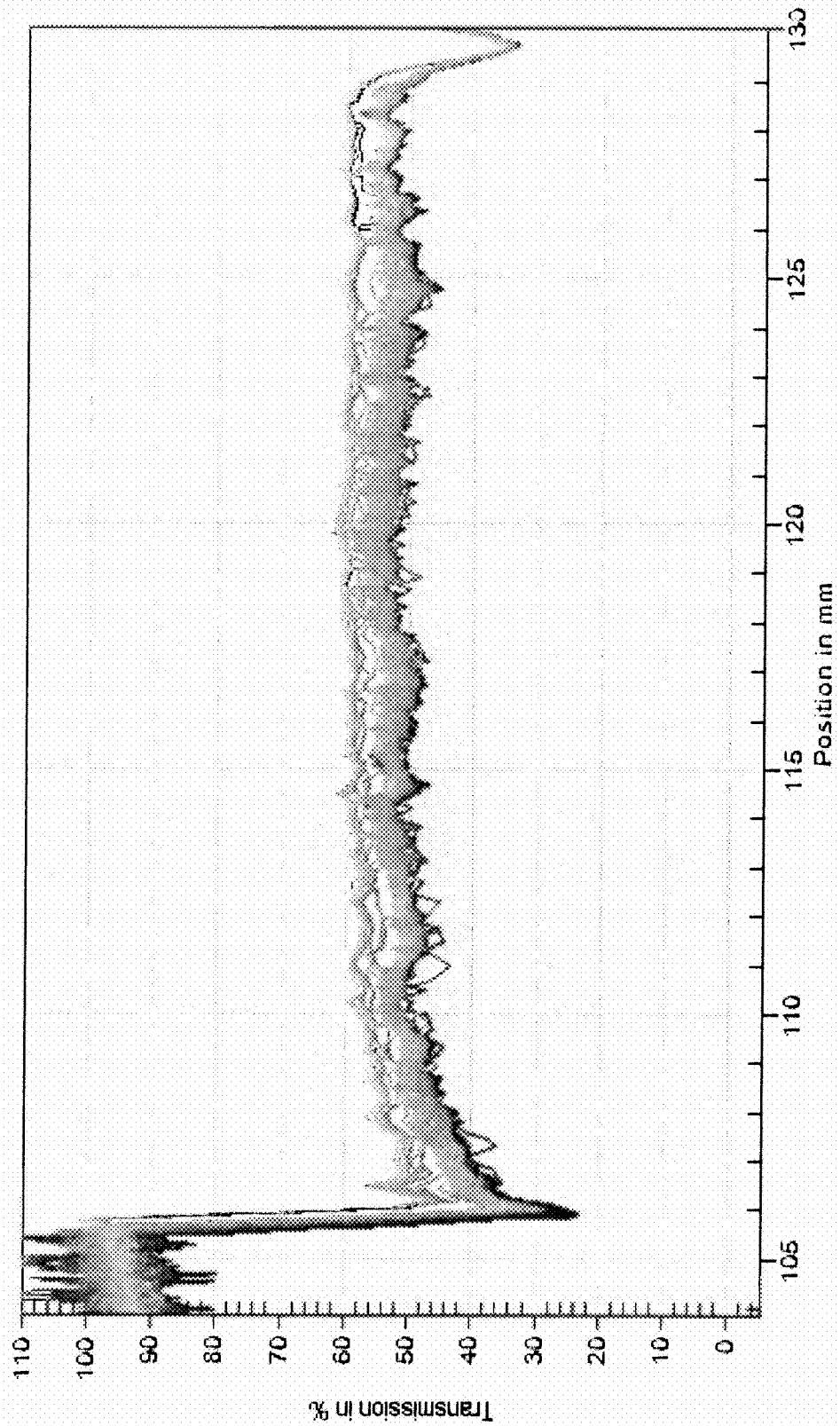
FIG. 35 shows Lumisizer™ light transmission measurement through neat Formulation F19.
Figure 36:
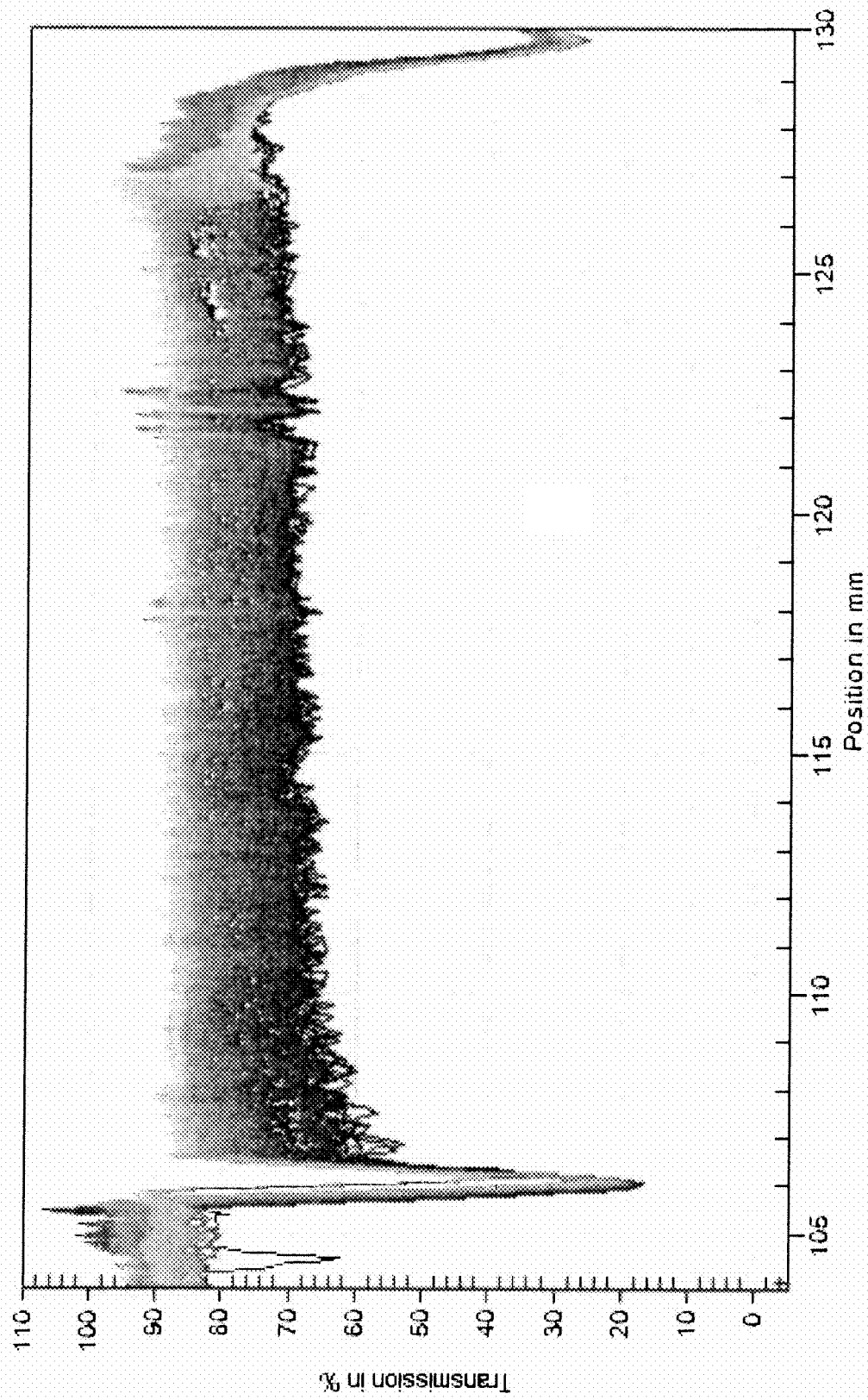
FIG. 36 shows Lumisizer™ light transmission measurement through a 1:1 mixture of Formulation F19 and HBSS.
Figure 37:
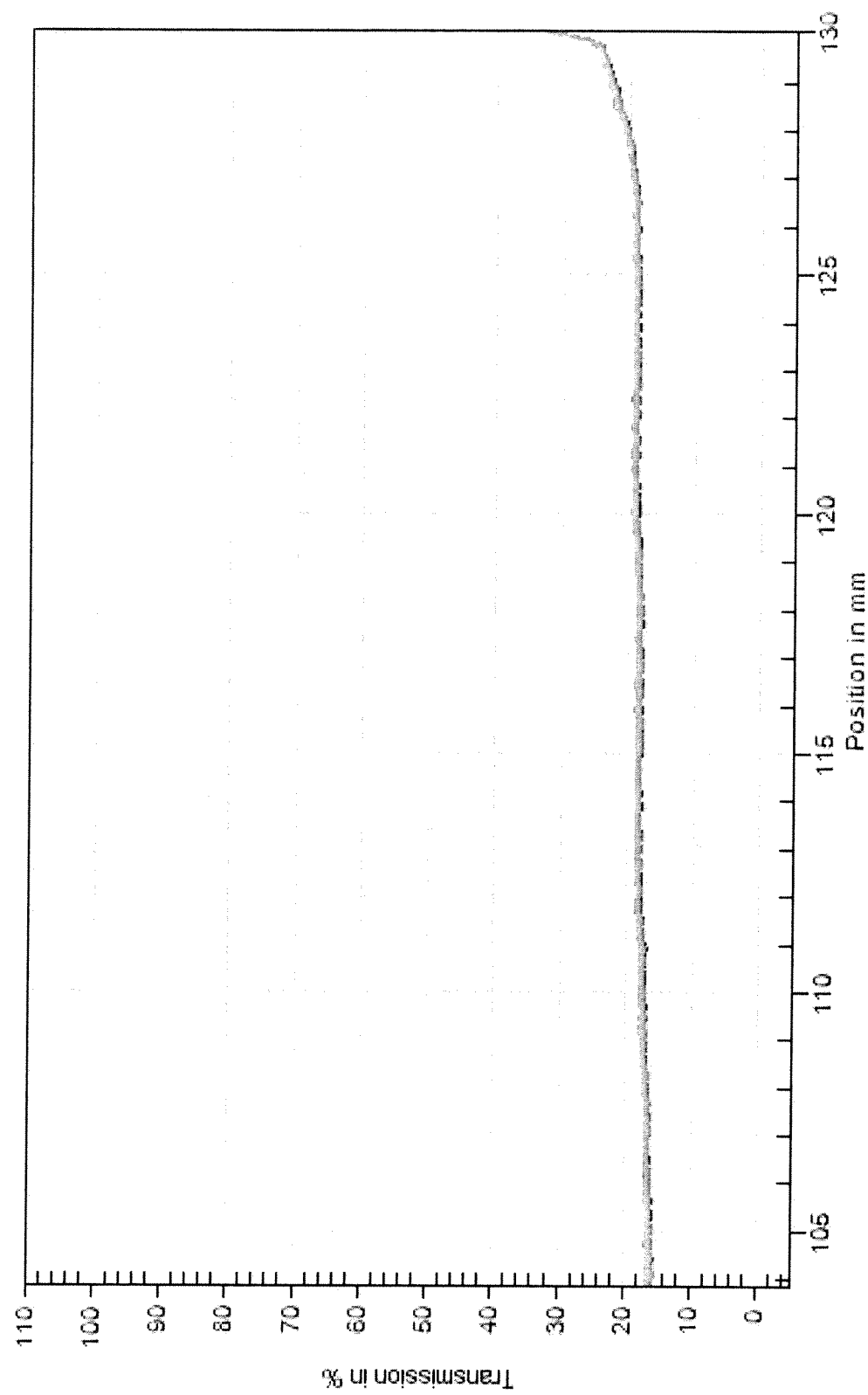
FIG. 37 shows Lumisizer™ light transmission measurement through neat Formulation F21.
Figure 38:
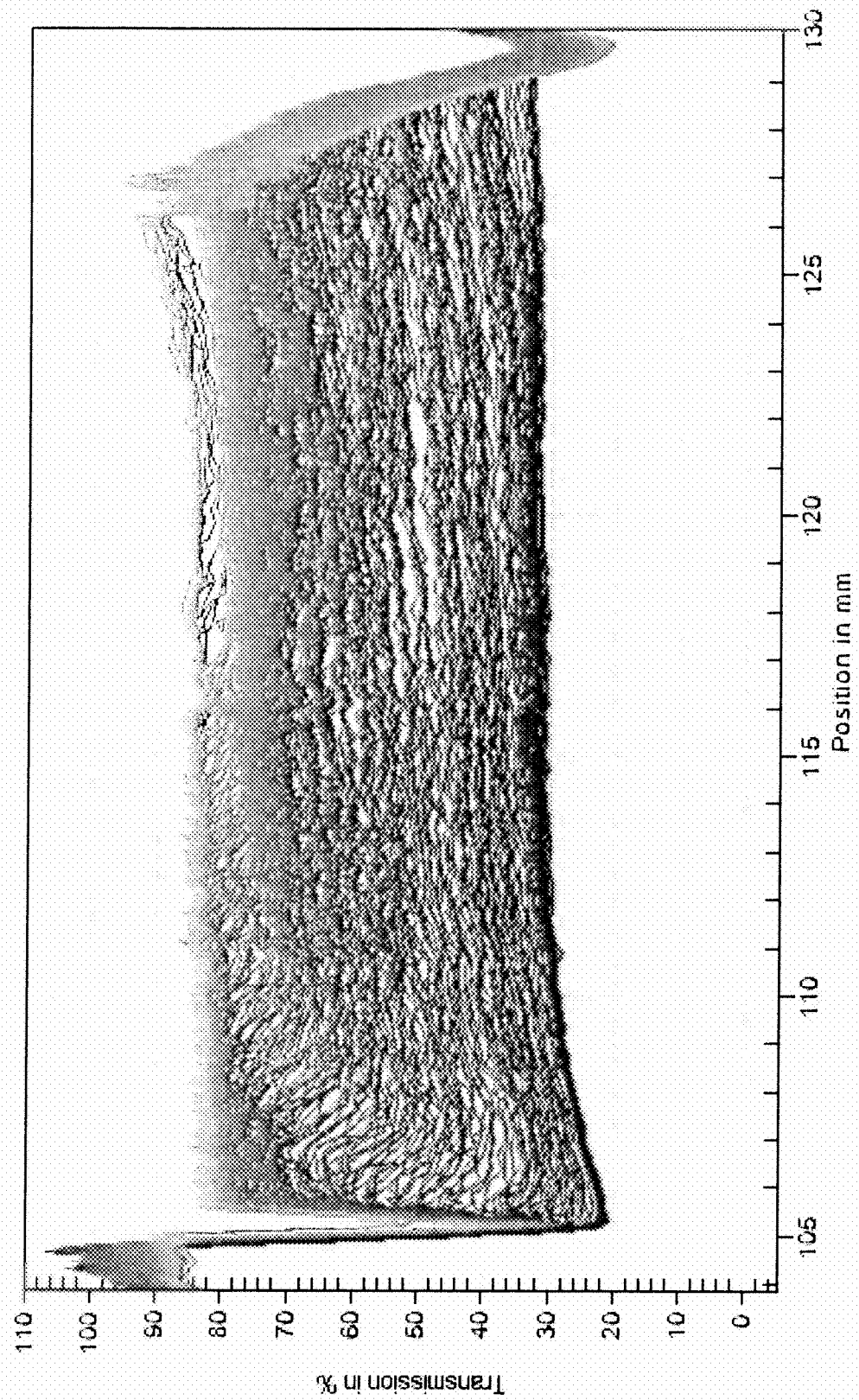
FIG. 38 shows Lumisizer™ light transmission measurement through a 1:1 mixture of Formulation F21 and HBSS.
Figure 39:
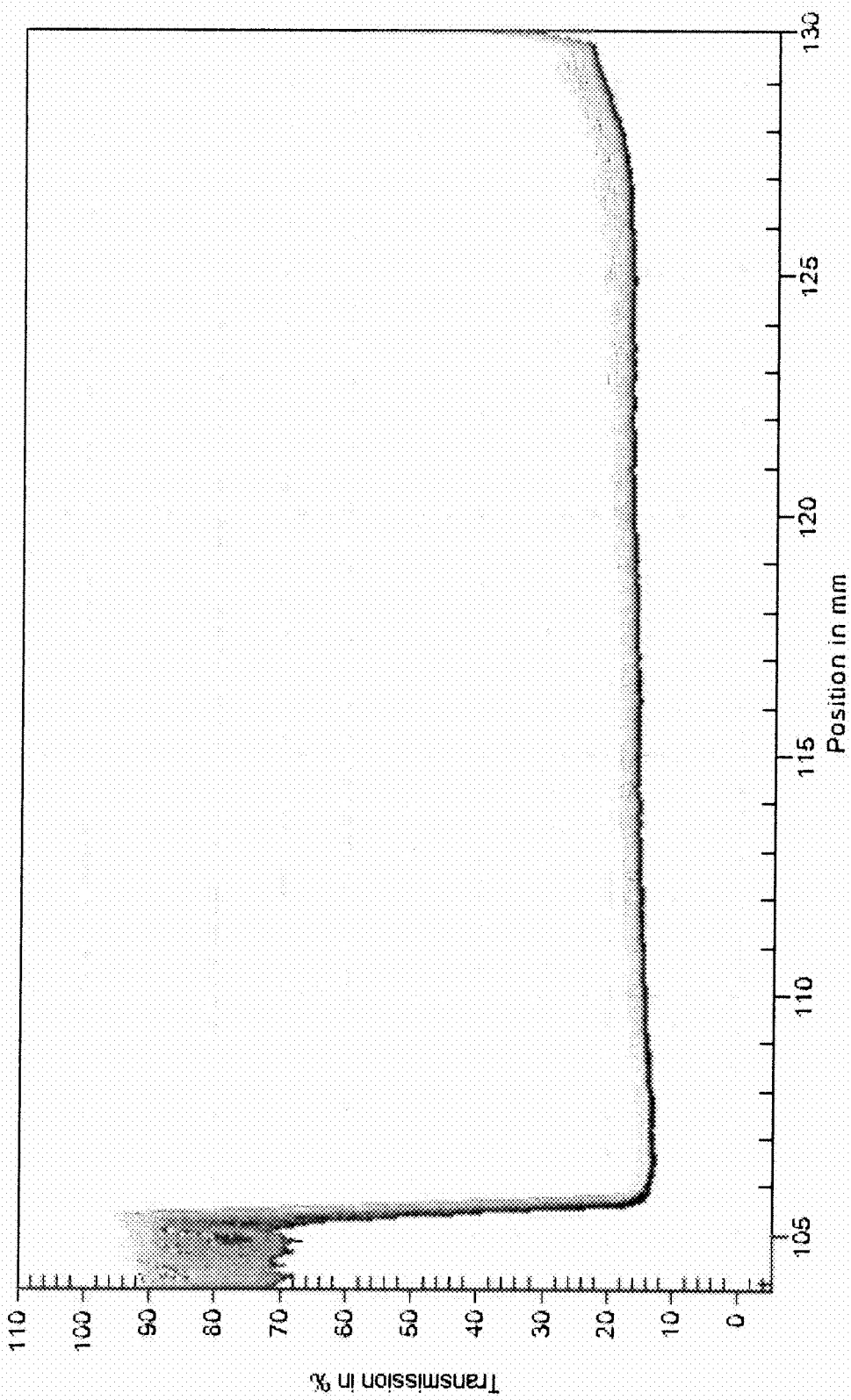
FIG. 39 shows Lumisizer™ light transmission measurement through neat Formulation F23.
Figure 40:
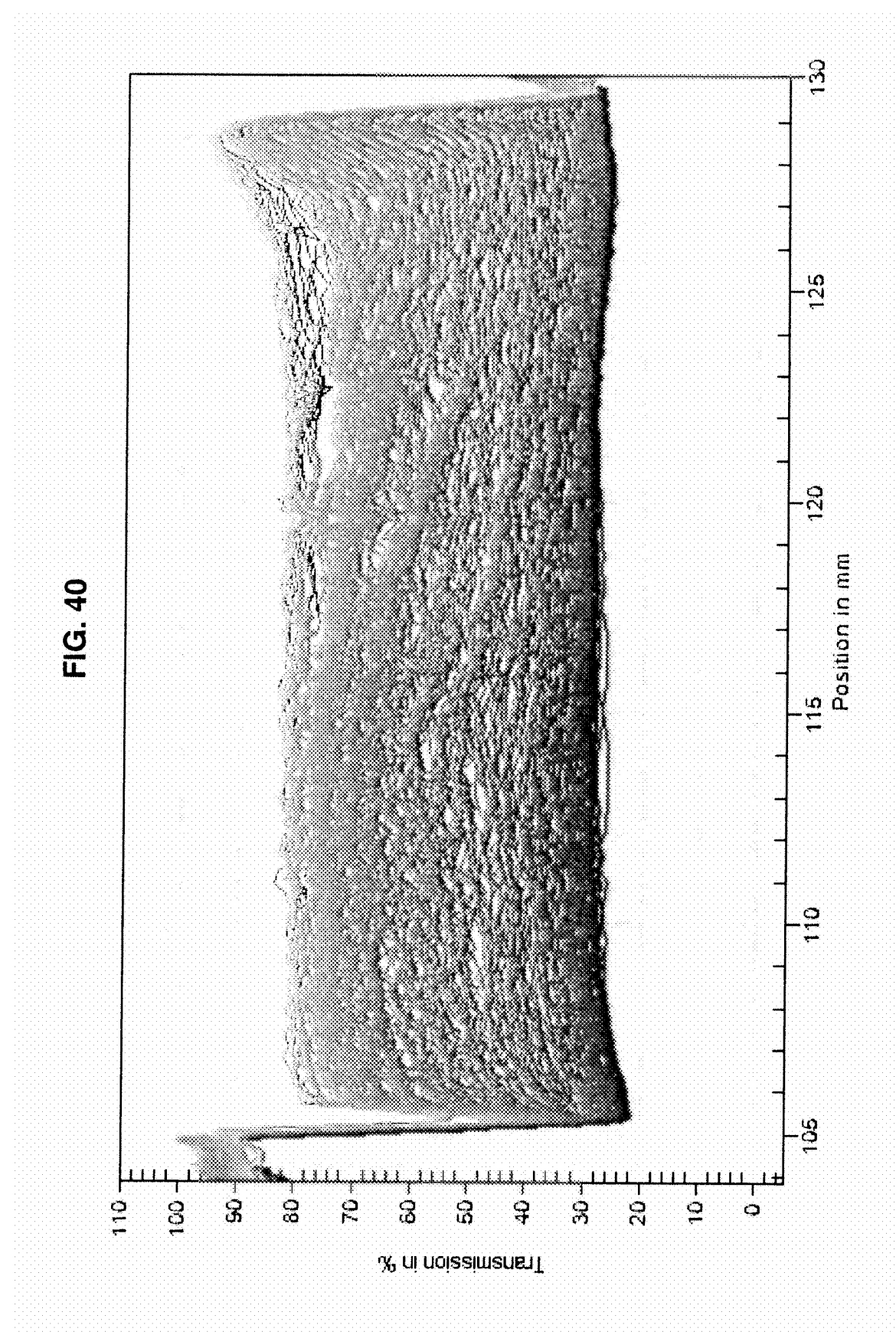
FIG. 40 shows Lumisizer™ light transmission measurement through a 1:1 mixture of Formulation F23 and HBSS.
Figure 41:
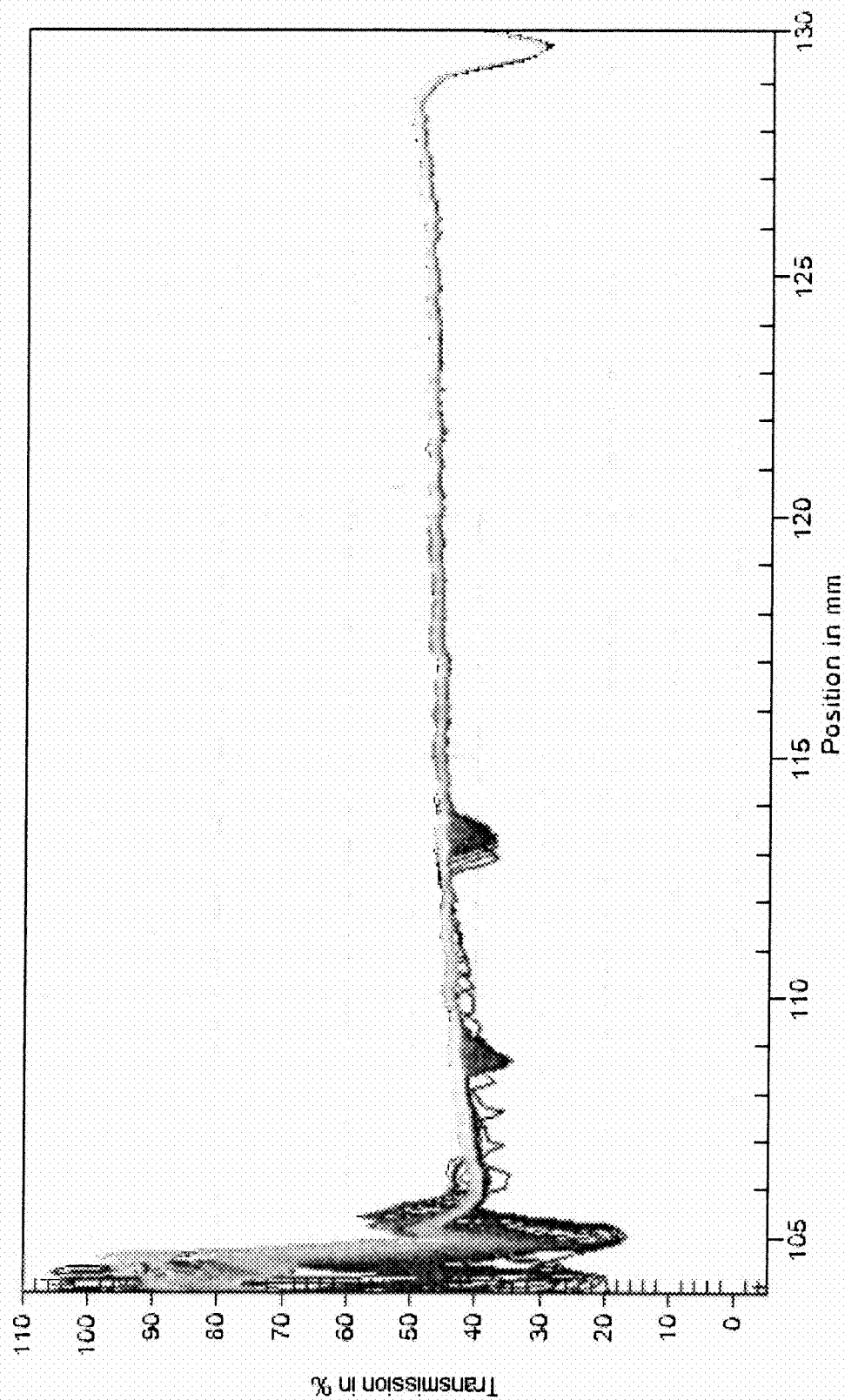
FIG. 41 shows Lumisizer™ light transmission measurement through neat Formulation F18.
Figure 42:
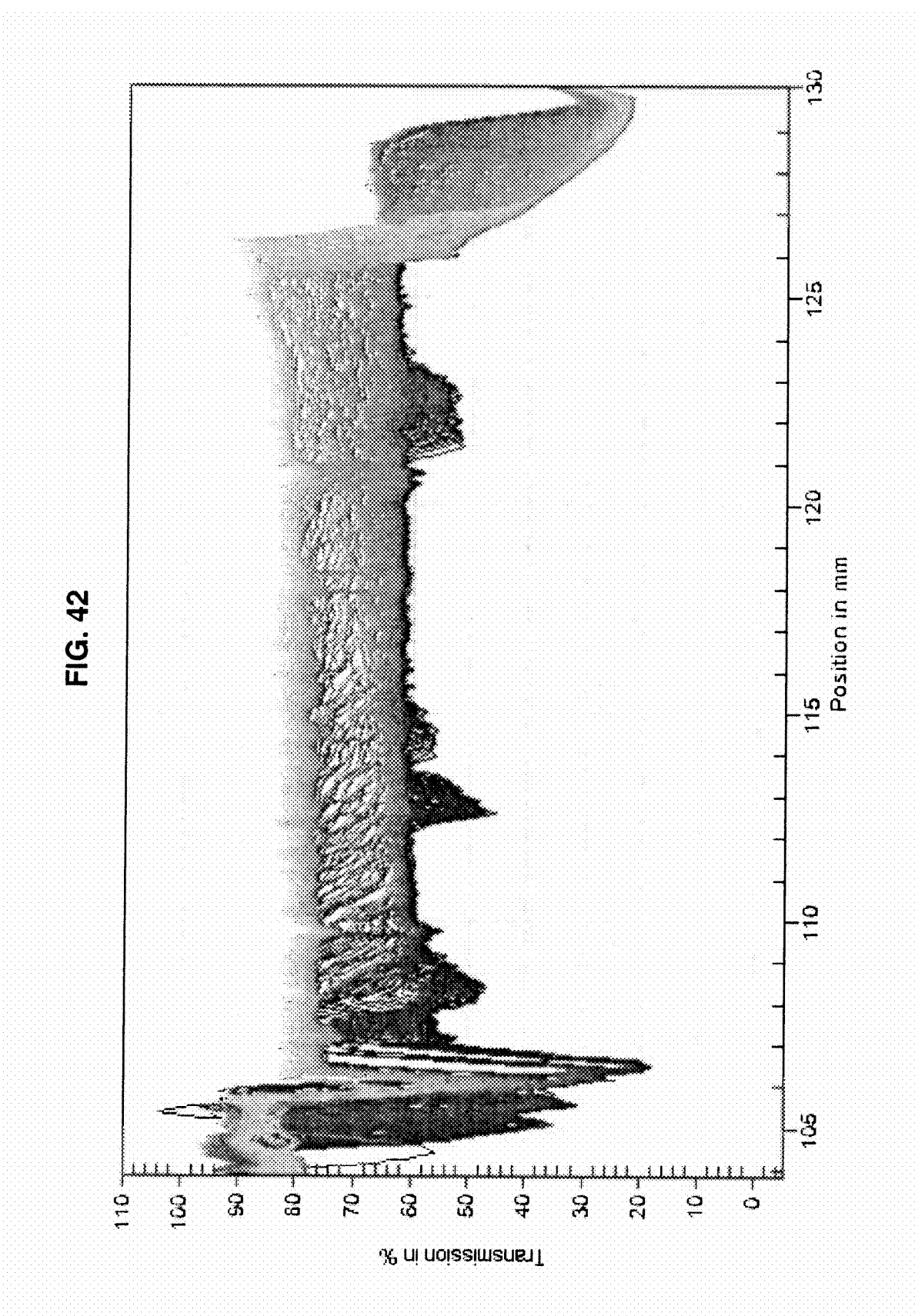
FIG. 42 shows Lumisizer™ light transmission measurement through a 1:1 mixture of Formulation F18 and HBSS.
Figure 43:
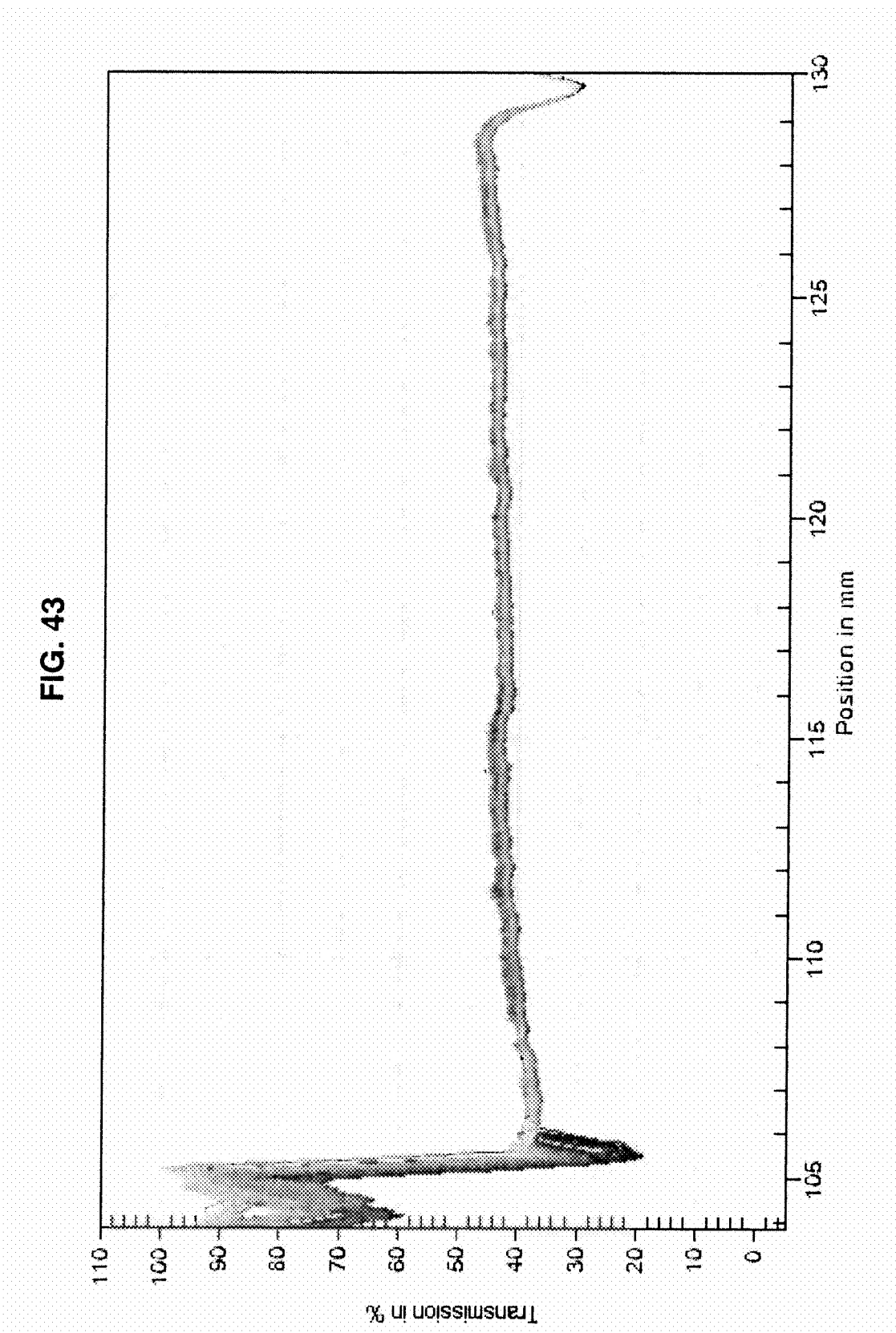
FIG. 43 shows Lumisizer™ light transmission measurement through neat Formulation F20.
Figure 44:
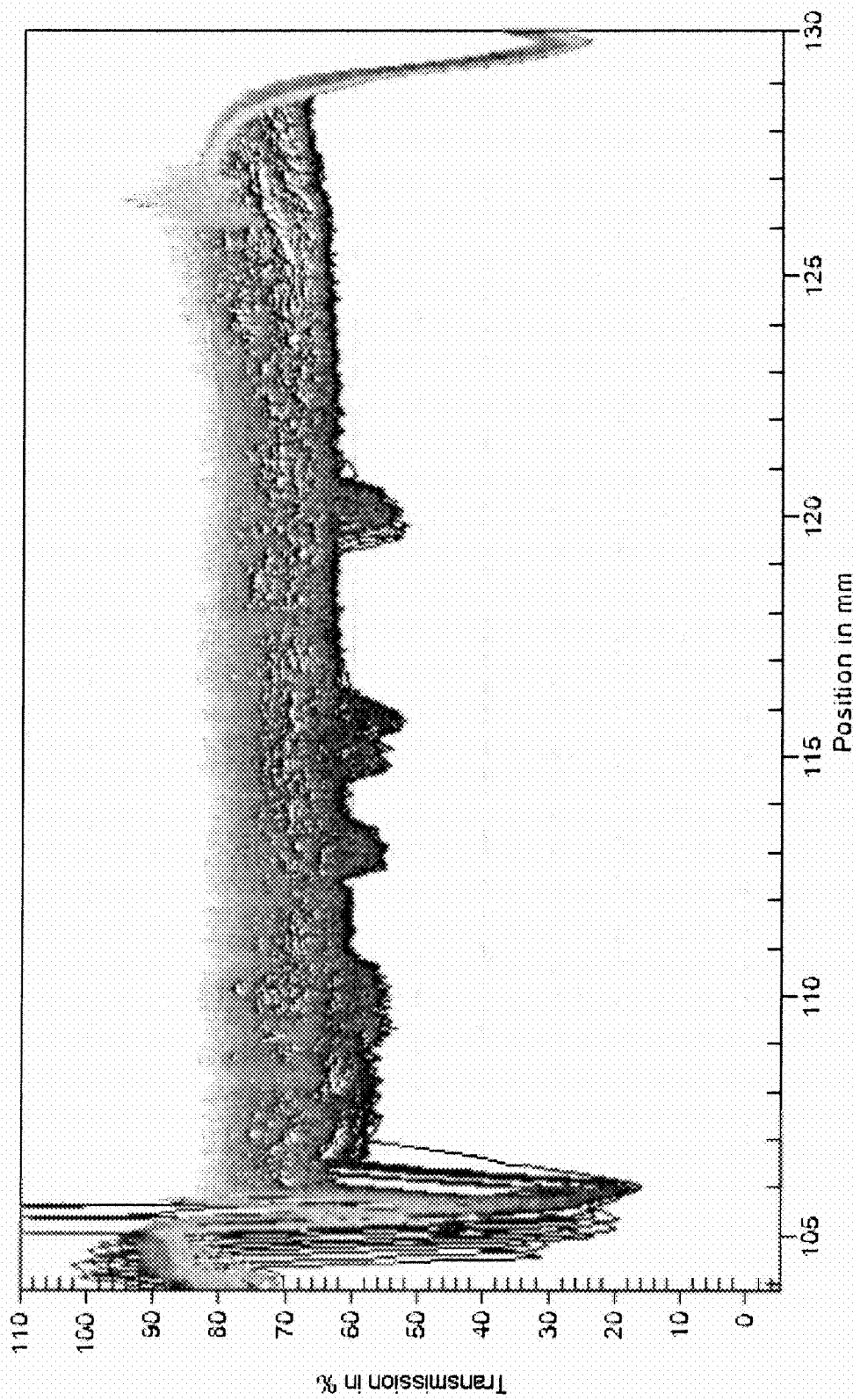
FIG. 44 shows Lumisizer™ light transmission measurement through a 1:1 mixture of Formulation F20 and HBSS.
Figure 45:
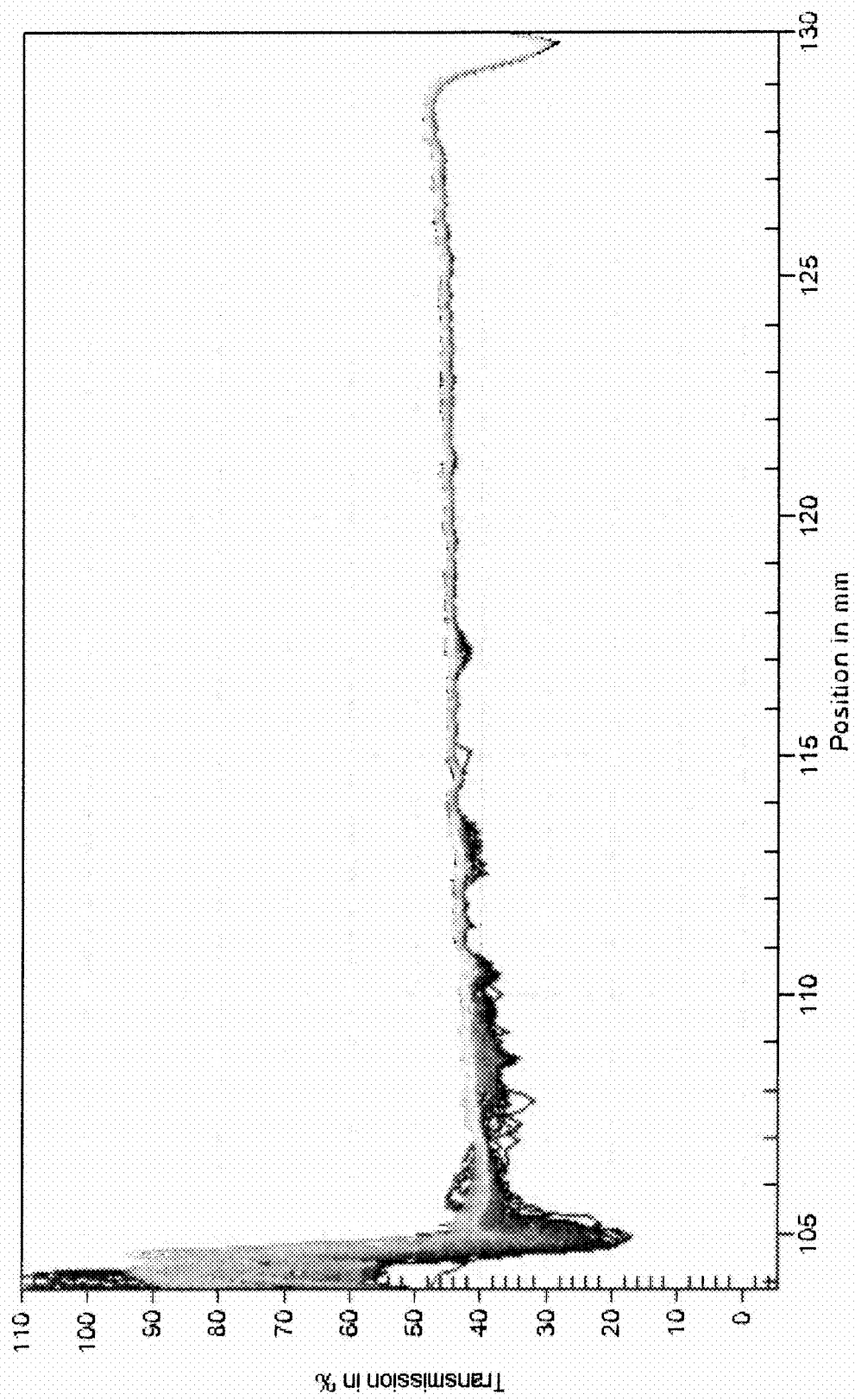
FIG. 45 shows Lumisizer™ light transmission measurement through neat Formulation F22.
Figure 46:
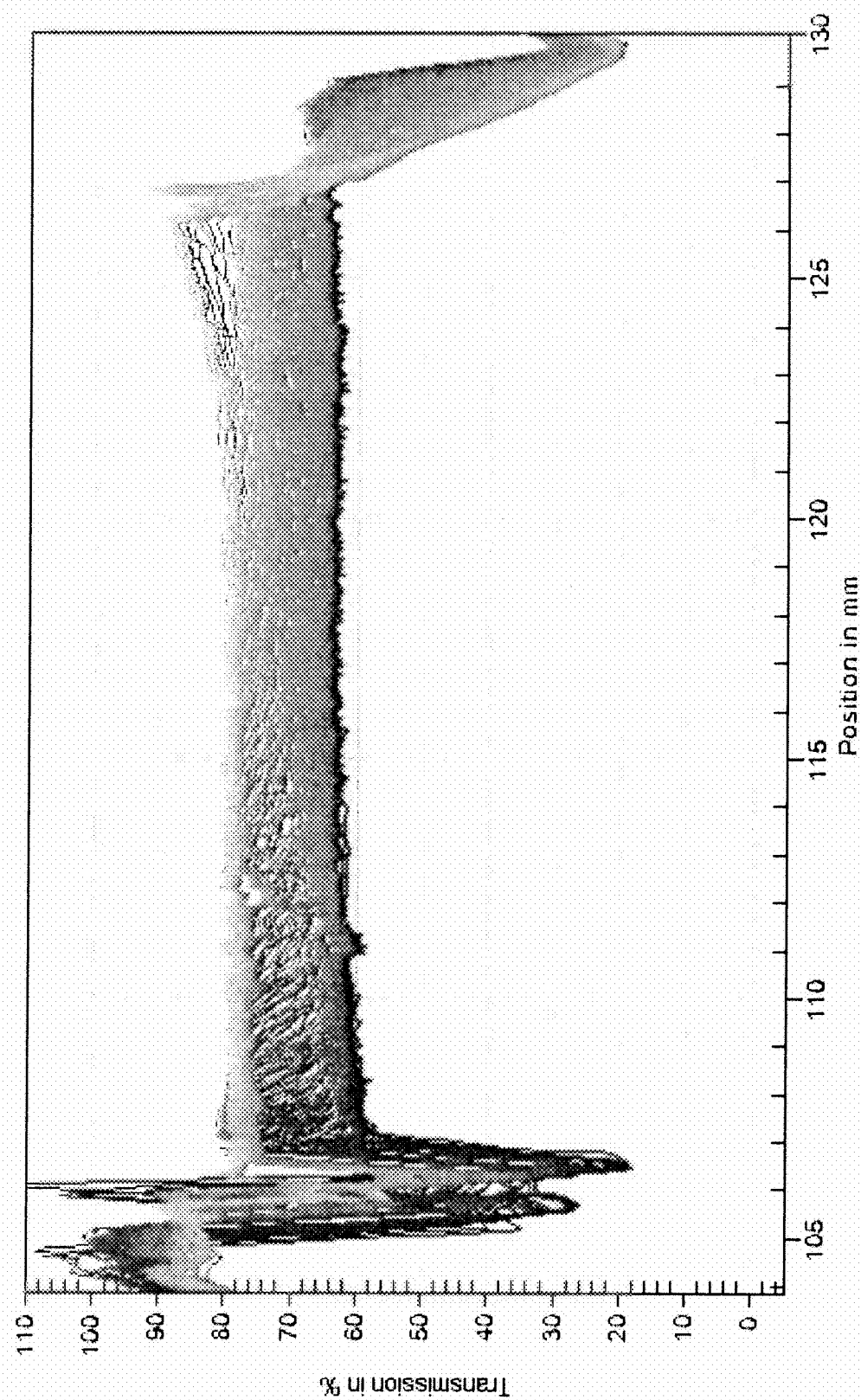
FIG. 46 shows Lumisizer™ light transmission measurement through a 1:1 mixture of Formulation F22 and HBSS.
Figure 47:
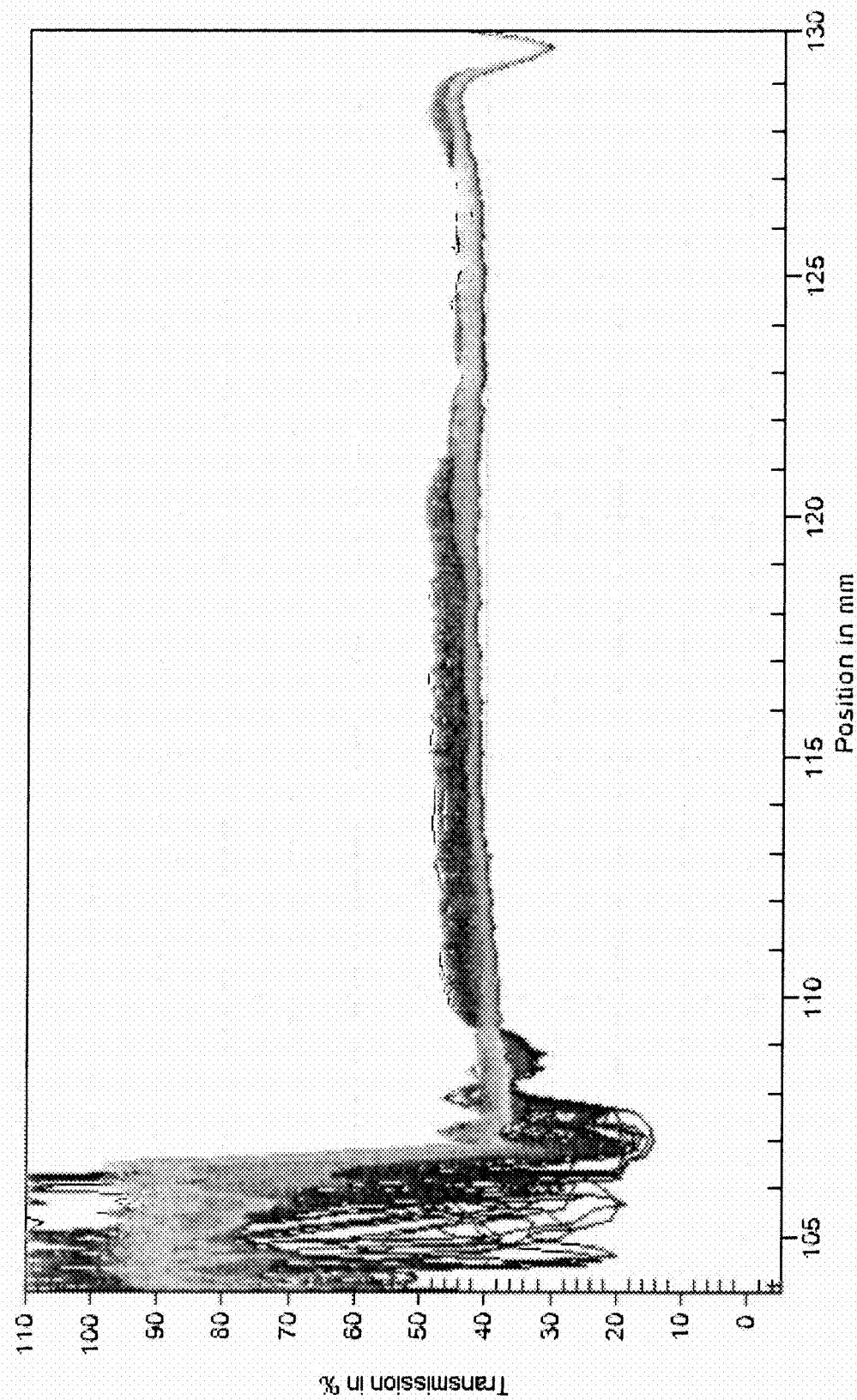
FIG. 47 shows Lumisizer™ light transmission measurement through neat Formulation F24.
Figure 48:
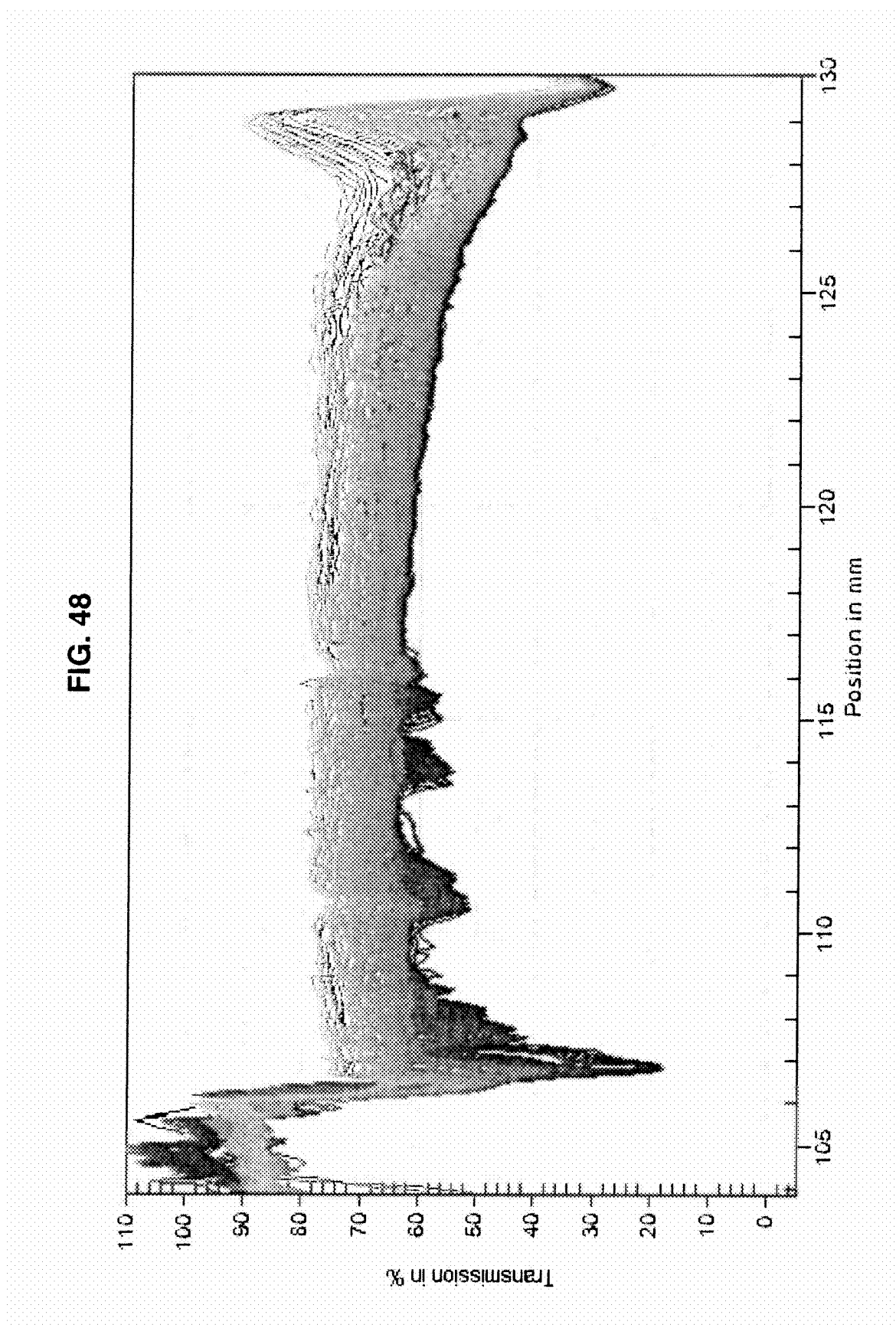
FIG. 48 shows Lumisizer™ light transmission measurement through a 1:1 mixture of Formulation F24 and HBSS.

For example, FIGS. 1 and 2 show that the neat Formulation F1 was very stable. However, when F1 was mixed with a simulated tear (HBSS) at a ratio 1:1, the resulting mixture became very unstable and separated into water and oil layers when subjected to centrifugal force. Thus, F1 can be a very effective composition in reducing evaporative loss of the tear film in dry eye patients.

Demonstration of the Ability of Selected Compositions of the Present Invention to Provide a Lipid Layer on the Surface of Water The next series of experiments demonstrates that a lipid phase can be easily separated from a composition of the present invention to provide a lipid layer on the surface of an aqueous phase, thus inhibiting evaporation of water from the tear film.

A well-known Langmuir trough was used for this series of experiments (KSV Instruments, Finland, Model 2000). A description of this Langmuir trough can be found at http://www.ksvnima.com/langmuir-and-langmuir-blodgett-troughs?gclid=CJ-Zo6WFyK0CFYuIfAodu20Big.

Briefly, the experiments use a Langmuir trough containing a water subphase, having symmetrically moving barriers to compress a thin film comprising molecules floating on the water subphase. The surface pressure ("SP") of the film is monitored by an electrobalance coupled to the liquid surface by means of a small strip of chromatography paper (Wilhelmy plate). The result is a Surface Pressure-Area ("SP-A") isotherm describing the SP response of the film to increasing lateral compression.

The test instrument was a Model 2000 Langmuir trough (KSV Instruments, Finland) equipped with an electrobalance and Wilhelmy plate to measure the SP, and symmetrically moving barriers for reducing the available surface area. The trough contained a dipping well at the center, which was modified with a magnetic stir plate and stir bar to enable the mixing of sample solutions injected into the subphase. Computer software controlled the barriers, monitored the balance, and plotted the resulting isotherm. The entire system was contained in an acrylic cabinet for dust and wind protection, and was mounted on a vibration isolation platform to minimize balance noise.

For each series of experiments, S-A isotherms were obtained for films, which spread on the surface of the trough subphase, of a synthetic meibum and the lipid component of a selected formulation of the present invention. The lipid component separated from an amount of formulation deposited, and remained, on the subphase surface.

The synthetic meibum was used as a model for the natural human meibum (a lipid-rich secretion produced by Meibomian glands located at the ocular lid margins of both upper and lower eyelids) and had the following composition: about 2 mg of lecithin (egg yolk or soy lecithin) and about 18 mg of lanolin in one mL of chloroform.

A lipid monolayer was established by carefully (via microsyringe) depositing 50 μL of the synthetic meibum solution on the surface of the subphase (deionized water at 21° C.), with the barriers in the open position. Similarly, a quantity of a selected test formulation that provided 50 μg, 100 μg, 150 μg, 200 μg, or 250 μg of the lipid component contained therein was deposited on the surface of the subphase. The solvent was allowed to evaporate for 15 minutes, or the water-miscible components of the test formulation to dissipate into the subphase. Then the compression/de-compression ("C/D") experiment was started.

The barriers moved toward the midline of the trough at a prescribed rate (compression), stopped at a preset point, then moved back to their original position (de-compression), while the SP was being monitored.

Figure 49:
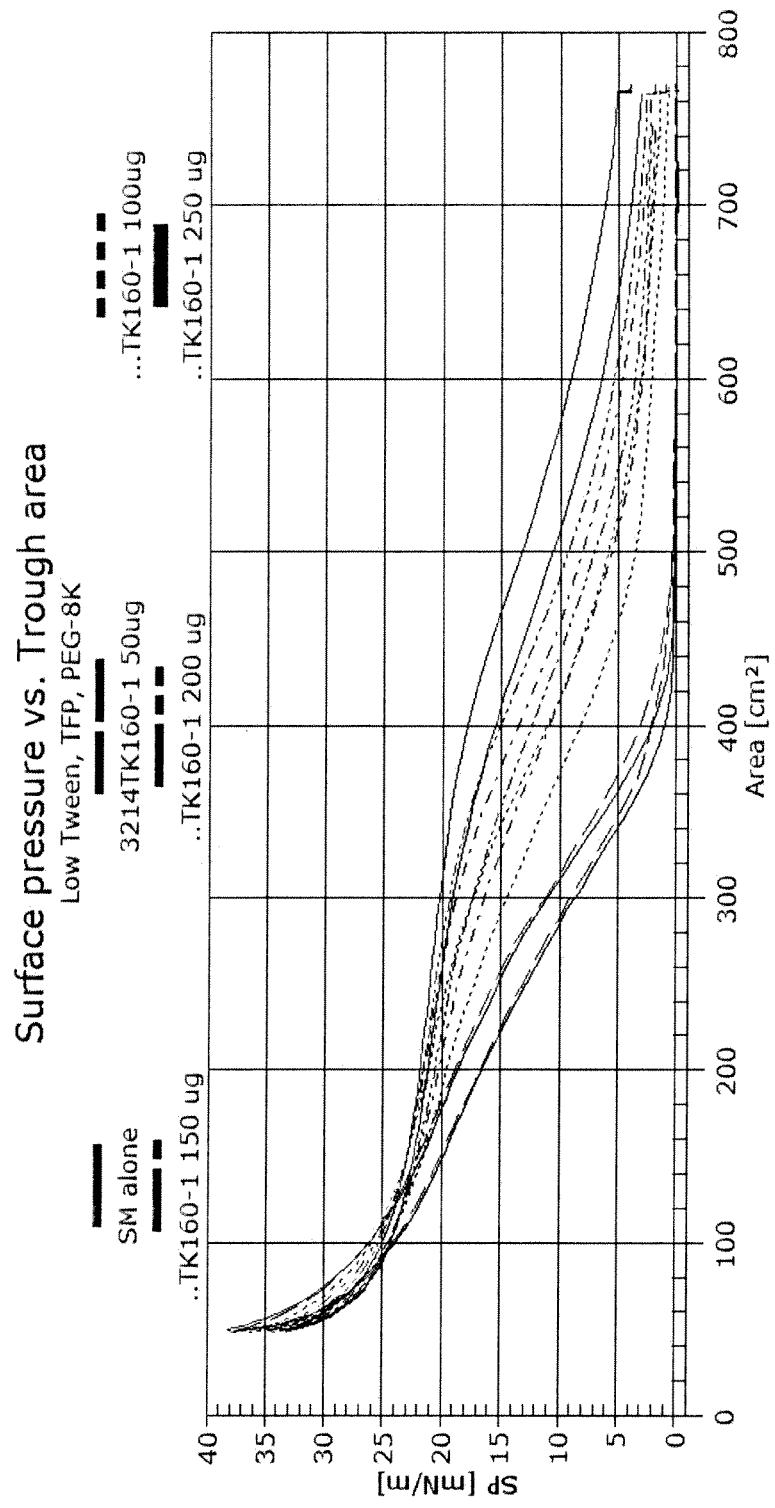
FIG. 49 shows surface pressure-versus-area isotherms of surface film comprising synthetic meibum or various amounts of oil from corresponding amounts of Formulation F15 (denoted as "3212TK160-1").

FIG. 49 shows SP-A isotherms for films comprising the synthetic meibum and 50 μg, 100 μg, 150 μg, 200 μg, and 250 μg of the medium-chain triglyceride contained in appropriate applied quantities of Formulation F15 of Table 8. As the area of the film decreases, molecules comprising the film start to be crowded together and the film becomes less compressible leading to an increase in the measured SP. Thus, an isotherm that exhibits a beginning of an increase in SP at a larger surface area has a wider surface coverage by molecules of the lipid component. Therefore, a formulation that produces such an isotherm would provide better protection to the tear film on the ocular surface. The SP-A isotherms of FIG. 49 indicate that at the same amount of a lipid component (50 μg), Formulation 15 would provide better protection to the tear film than the synthetic meibum by virtue of the fact that the measured SP begins to increase at a larger surface area.

Figure 50:
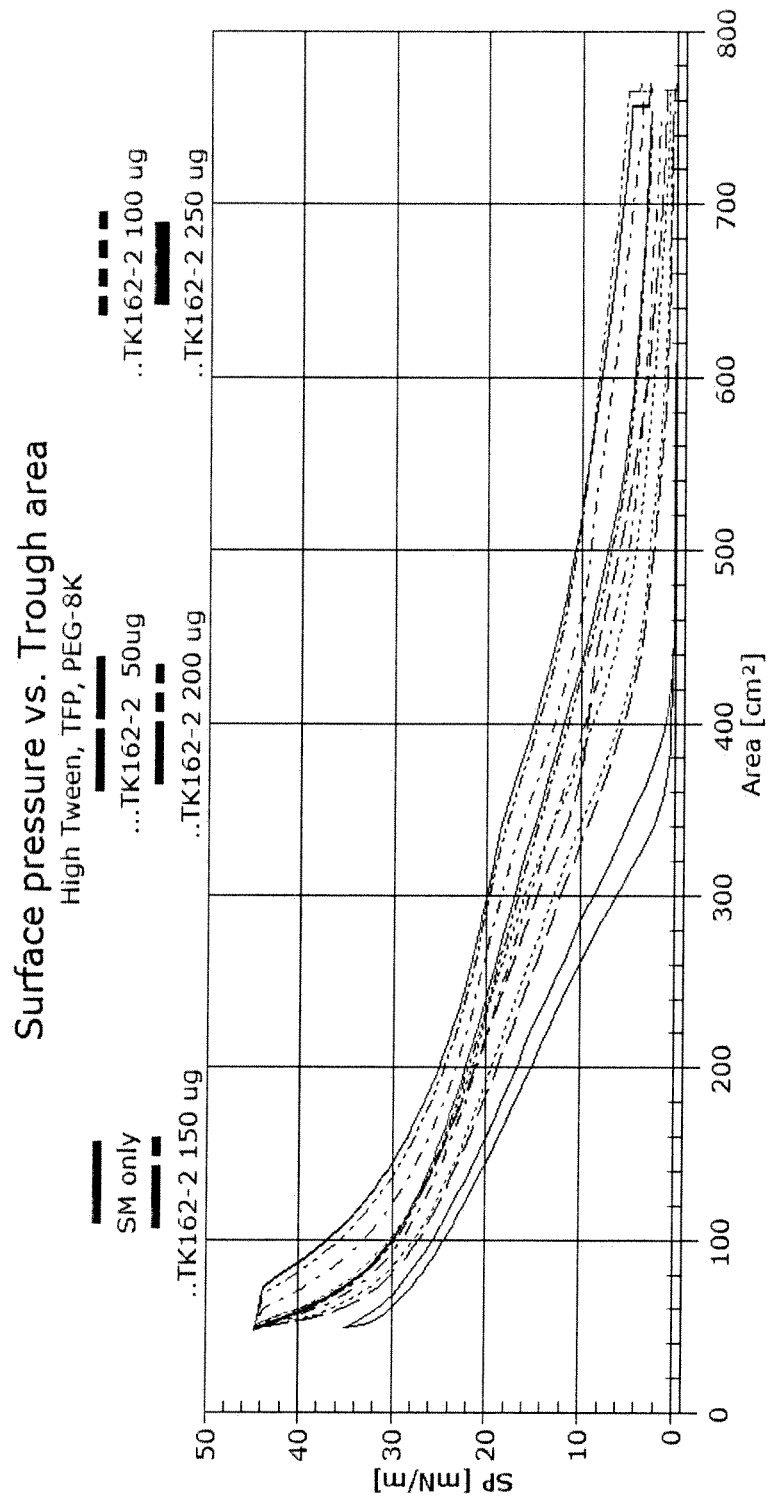
FIG. 50 shows surface pressure-versus-area isotherms of surface film comprising synthetic meibum or various amounts of oil from corresponding amounts of Formulation F16 (denoted as "TK162-2").
Figure 51:
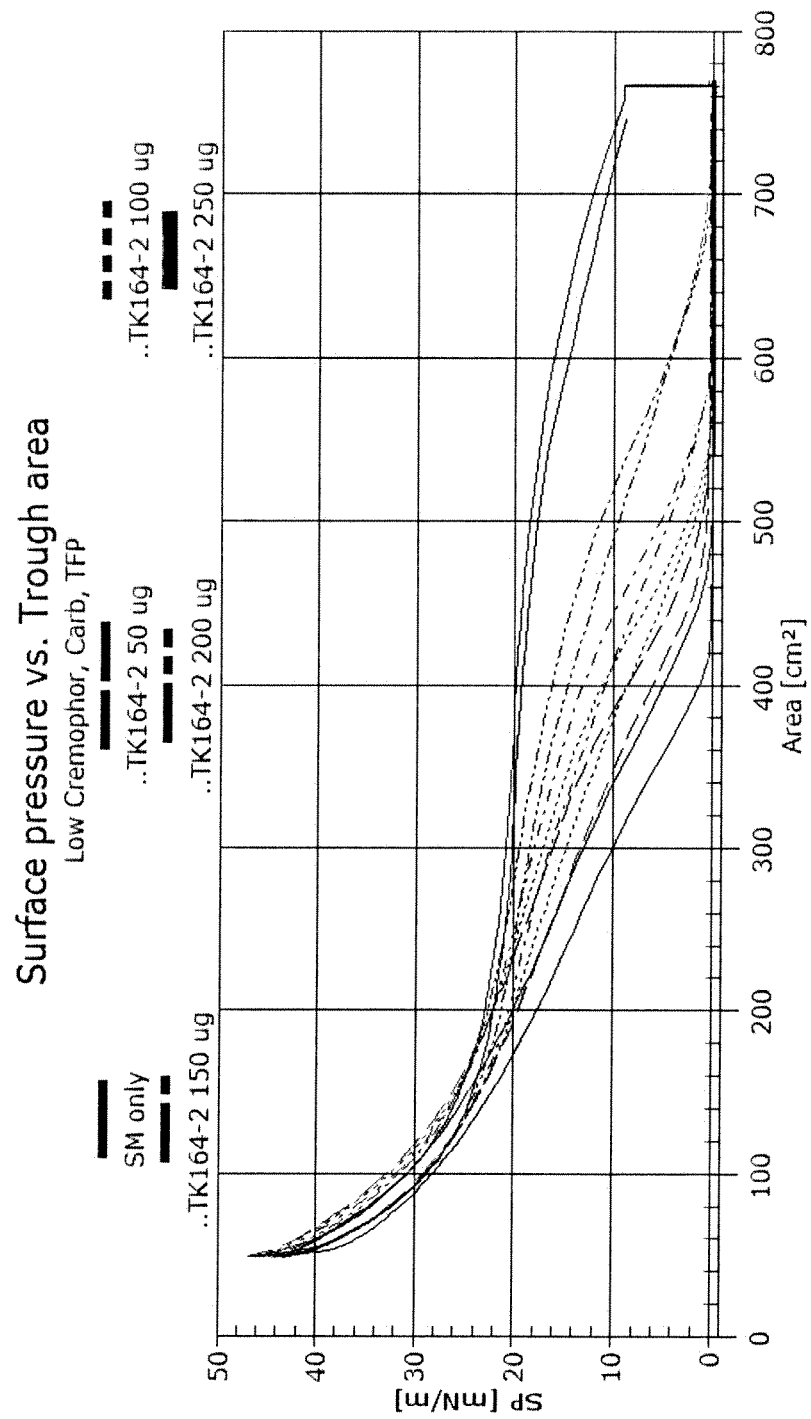
FIG. 51 shows surface pressure-versus-area isotherms of surface film comprising synthetic meibum or various amounts of oil from corresponding amounts of Formulation F21 (denoted as "TK164-2").
Figure 52:
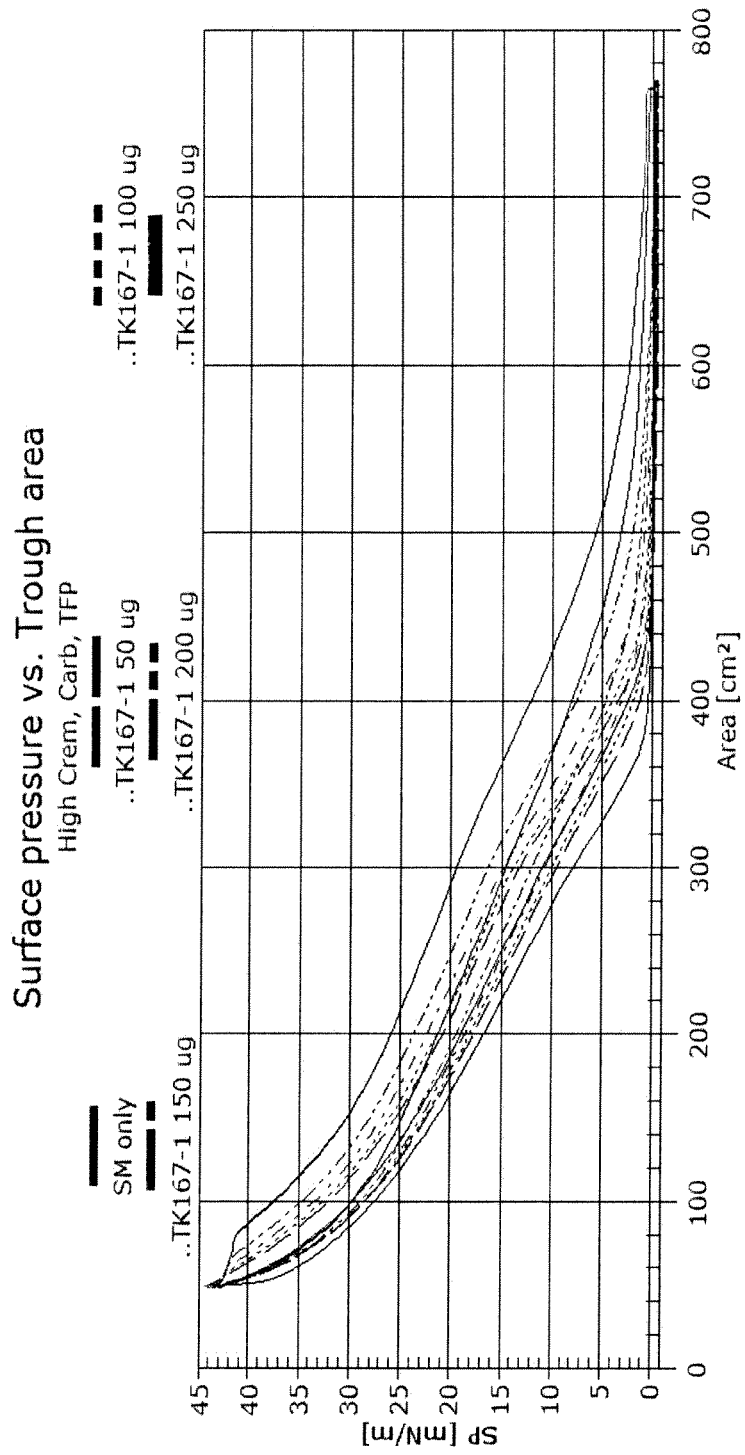
FIG. 52 shows surface pressure-versus-area isotherms of surface film comprising synthetic meibum or various amounts of oil from corresponding amounts of Formulation F22 (denoted as "TK167-1").

Similarly, FIGS. 50-52 show that Formulations F16, F21, and F22 of the present invention would also provide more effective protection to the tear film on the ocular surface.

In another aspect, any composition herein disclosed can serve as a vehicle for an ophthalmic API. Such an ophthalmic API can be dissolved in the oil phase or the aqueous phase. In one embodiment, such an ophthalmic API is dissolved in the oil phase.

For example, in one aspect, a composition of the present invention comprises an emulsion which comprises, consists of, or consists essentially of: (a) a first polymer, a viscosity of which changes in response to a change in concentration of an electrolyte, such as a salt, added to said first polymer; (b) a second polymer that is different from the first polymer and that comprises a polyanionic polysaccharide; (c) an oil; (d) an ophthalmic API dissolved in said oil; and (e) water; wherein the emulsion comprises an oil phase-in-aqueous phase emulsion, and the emulsion is stable on storage but breaks up into separate aqueous and oil phases when diluted with tear resident in the eye.

In another embodiment, a composition of the present invention comprises an emulsion which comprises, consists of, or consists essentially of: (a) a first polymer, a viscosity of which changes in response to a change in concentration of an electrolyte, such as a salt, added to said first polymer; (b) a second polymer that is different from the first polymer, can modify the viscosity of the first polymer, and comprises a polyanionic polysaccharide; (c) an oil; (d) an ophthalmic API dissolved in said oil; and (e) water; wherein the emulsion comprises an oil phase-in-aqueous phase emulsion, and the emulsion is stable on storage but breaks up into separate aqueous and oil phases when diluted with tear resident in the eye.

In still another embodiment, a composition of the present invention comprises an emulsion which comprises, consists of, or consists essentially of: (a) a first polymer, a viscosity of which changes in response to a change in concentration of an electrolyte, such as a salt, added to said first polymer; (b) a second polymer that is different from the first polymer and that can modify the viscosity of the first polymer; (c) an oil; (d) an ophthalmic API dissolved in said oil; and (e) water; wherein the emulsion comprises an oil phase-in-aqueous phase emulsion, and the emulsion is stable on storage but breaks up into separate aqueous and oil phases when diluted with tear resident in the eye.

Non-limiting examples of such oil-soluble ophthalmic APIs include prostaglandin analogs that have been used for treating ocular hypertension, oil-soluble vitamins, such as vitamins A, D, and E, and omega-3 fatty acid. Non-limiting examples of prostaglandin analogs include latanoprost, travoprost, bimatoprost, and unoprostone.

In one embodiment, a composition of the present invention comprises an emulsion which comprises, consists of, or consists essentially of: (a) a first polymer, a viscosity of which changes in response to a change in concentration of an electrolyte, such as a salt, added to said first polymer; (b) a second polymer that is different from the first polymer, can modify the viscosity of the first polymer, and comprises a polyanionic polysaccharide; (c) an oil; (d) an ophthalmic API dissolved in said oil, said ophthalmic API being selected from the group consisting of prostaglandin analogs; and (e) water; wherein the emulsion comprises an oil phase-in-aqueous phase emulsion, and the emulsion is stable on storage but breaks up into separate aqueous and oil phases when diluted with tear resident in the eye.

In another embodiment, a composition of the present invention comprises an emulsion which comprises, consists of, or consists essentially of: (a) a first polymer, a viscosity of which changes in response to a change in concentration of an electrolyte, such as a salt, added to said first polymer, said first polymer being selected from the group consisting of cross-linked polyacrylic acids, such as carbomers, polycarbophil, carbopol, Pemulen®; (b) a second polymer that is different from the first polymer and that can modify the viscosity of the first polymer; (c) an oil; (d) an ophthalmic API dissolved in said oil, said ophthalmic API being selected from the group consisting of prostaglandin analogs; and (e) water; wherein the emulsion comprises an oil phase-in-aqueous phase emulsion, and the emulsion is stable on storage but breaks up into separate aqueous and oil phases when diluted with tear resident in the eye.

In another embodiment, a composition of the present invention comprises an emulsion which comprises, consists of, or consists essentially of: (a) a first polymer, a viscosity of which changes in response to a change in concentration of an electrolyte, such as a salt, added to said first polymer, said first polymer being selected from the group consisting of cross-linked carboxyvinyl polymers, such as polyacrylic acids, carbomers, polycarbophil, carbopol, Pemulen®; (b) a second polymer that is a polyanionic polysaccharide and can modify the viscosity of the first polymer; (c) an oil; (d) an ophthalmic API dissolved in said oil, said ophthalmic API being selected from the group consisting of prostaglandin analogs; and (e) water; wherein the emulsion comprises an oil phase-in-aqueous phase emulsion, and the emulsion is stable on storage but breaks up into separate aqueous and oil phases when diluted with tear resident in the eye. Said polyanionic polysaccharide is selected from the group of polysaccharide disclosed herein above. Said prostaglandin analogs can be selected from the group consisting of latanoprost, travoprost, bimatoprost, unoprostone, and combinations thereof. A prostaglandin analog can be present in said composition at a concentration in the range from about 0.0001 to about 0.2 percent (or alternatively, from about 0.001 to about 0.1, or from about 0.005 to about 0.07, or from about 0.01 to about 0.05 percent) by weight of the total composition.

Such a composition advantageously provides an enhanced stability of the prostaglandin analog. In one aspect, such stability is exhibited by a degradation of said prostaglandin analog of less than 5 (or alternatively, less than 2) percent of the original concentration thereof after storage at room temperature for 2 weeks.

In another aspect, the present invention provides a method for enhancing a stability of a prostaglandin analog in an ophthalmic pharmaceutical composition. The method comprises dissolving said prostaglandin analog in an oil, adding an aqueous medium to said oil, and preparing an oil-in-water emulsion from said oil and said aqueous medium. In one embodiment, such a method results in a degradation of said prostaglandin analog of less than 5 (or alternatively, less than 2) percent of the original concentration thereof after storage at room temperature for 2 weeks.

In a further aspect, the present invention provides a method for treating, controlling, reducing, or ameliorating ocular hypertension. The method comprises administering any of the foregoing compositions comprising a prostaglandin analog to an affected eye of a patient in an amount and at a frequency effective to treat, control, reduce, or ameliorate said ocular hypertension. Such an amount can be, for example, one, two, three, four, or more drops of said composition. Such frequency can be, for example, once, twice, three times, four or more times per day.

While specific embodiments of the present invention have been described in the foregoing, it will be appreciated by those skilled in the art that many equivalents, modifications, substitutions, and variations may be made thereto without departing from the spirit and scope of the invention as defined in the appended claims.

What is claimed is:

1. An ophthalmic pharmaceutical composition comprising an oil-in-water emulsion that comprises: (a) a first polymer comprising a polymer or copolymer of carboxyvinyl monomers; the first polymer being present at a concentration in the range from about 0.01 to about 1 percent by weight of the composition; (b) a second polymer comprising a polyanionic polysaccharide selected from the group consisting of alginic acid, hyaluronic acid, salts of alginic acid or hyaluronic acid, and glucuronoxylomannan extracted from *Tremella fuciformis* mushroom; the second polymer being present at a concentration in the range from about 0.01 to about 1 percent by weight of the composition; (c) a caprylic acid/capric acid medium-chain triglyceride present at a concentration in the range from about 0.01 to about 1 percent by weight of the composition; (d) a non-ionic surfactant present at a concentration in the range from about 0.01 to about 1 percent by weight of the composition; and (e) water; wherein the emulsion is stable on storage but breaks up into separate aqueous and oil phases when diluted with simulated tear or subjected to shear stress; and wherein the composition has a viscosity in the range from about 2 to about 1000 cP.

2. The composition of claim 1, wherein said composition has a viscosity in the range from about 100 to about 1000 centipoises.

3. The composition of claim 1, further comprising an active pharmaceutical ingredient dissolved in said oil.

4. The composition of claim 2, further comprising an active pharmaceutical ingredient dissolved in said oil.

5. The composition of claim 4, wherein said active pharmaceutical ingredient is selected from the group consisting of prostaglandin analogs.

6. The composition of claim 5, wherein said active pharmaceutical ingredient is latanoprost.

7. A pharmaceutical composition consisting essentially of: (a) a carboxyvinyl polymer at a concentration from about 0.1 to about 0.5 percent by weight of the total composition; (b) a polysaccharide that is selected from the group consisting of alginic acid, hyaluronic acid, salts of alginic acid or hyaluronic acid, and glucuronoxylomannan extracted from *Tremella fuciformis* mushroom and that is present in the composition at a concentration from about 0.05 to about 0.5 percent by weight of the total composition; (c) a caprylic acid/capric acid medium-chain triglyceride at a concentration from about 0.2 to about 0.5 percent by weight of the total composition; (d) a single non-ionic surfactant selected from the group consisting of Octoxynol 40, polysorbate 80, and Cremopor EL, at a concentration from about 0.01 to about 0.5 percent by weight of the total composition; (e) a polyol selected from the group consisting of glycerin, propylene glycol, and mixture thereof, at a concentration from about 0.1 to about 1 percent by weight of the total composition; and (f) water; wherein the composition is a stable oil-in-water emulsion in storage but breaks up into separate aqueous phase and oil phase when diluted with simulated tear.

8. A pharmaceutical composition consisting essentially of: (a) a carboxyvinyl polymer at a concentration from about 0.1 to about 0.5 percent by weight of the total composition: (b) a polysaccharide that is selected from the group consisting of alginic acid, hyaluronic acid, salts thereof, and glucuronoxylomannan extracted from *Tremella fuciformis* mushroom and that is present in the composition at a concentration from about 0.05 to about 0.5 percent by weight of the total composition; (c) a caprylic/capric acid medium-chain triglyceride at a concentration from about 0.2 to about 0.5 percent by weight of the total composition; (d) a single non-ionic surfactant selected from the group consisting of Octoxynol 40, polysorbate 80, and Cremopor EL, at a concentration from about 0.01 to about 0.5 percent by weight of the total composition; (e) a polyol selected from the group consisting of glycerin, propylene glycol, and mixture thereof, at a concentration from about 0.1 to about 1 percent by weight of the total composition; and (f) boric acid and borate buffer; wherein the composition has a pH from about 7 to about 7.5; and wherein the composition is a stable oil-in-water emulsion in storage but breaks up into separate aqueous phase and oil phase when diluted with simulated tear.

* * * * *